US012565525B2

(12) United States Patent
Sprogøe et al.

(10) Patent No.: US 12,565,525 B2

(45) Date of Patent: Mar. 3, 2026

(54) IL-2 CONJUGATES

(71) Applicant: Ascendis Pharma Oncology Division A/S, Hellerup (DK)

(72) Inventors: Kennett Sprogøe, Hellerup (DK); Harald Rau, Heidelberg (DK); Thomas Knappe, Heidelberg (DE); Nicola Bisek, Heidelberg (DE); Burkhardt Laufer, Heidelberg (DE)

(73) Assignee: ASCENDIS PHARMA ONCOLOGY DIVISION A/S, Hellerup (DK)

( * ) Notice: Subject to any disclaimer, the term of this patent is extended or adjusted under 35 U.S.C. 154(b) by 1162 days.

(21) Appl. No.: 17/042,610

(22) PCT Filed: Mar. 27, 2019

(86) PCT No.: PCT/EP2019/057709

§ 371 (c)(1),
(2) Date: Sep. 28, 2020

(87) PCT Pub. No.: WO2019/185705

PCT Pub. Date: Oct. 3, 2019

(65) Prior Publication Data

US 2021/0024602 A1 Jan. 28, 2021

(30) Foreign Application Priority Data

Mar. 28, 2018 (EP) .................................... 18164682

(51) Int. Cl.
*C07K 14/55* (2006.01)
*A61K 47/60* (2017.01)

(52) U.S. Cl.
CPC .............. *C07K 14/55* (2013.01); *A61K 47/60* (2017.08)

(58) Field of Classification Search
CPC ...... C07K 14/55; C07K 1/1077; A61K 47/60; A61K 38/00; A61K 47/183; A61K 47/542; A61P 35/00
See application file for complete search history.

(56) References Cited

U.S. PATENT DOCUMENTS

| | | | | |
|---|---|---|---|---|
| 4,766,106 | A | 8/1988 | Katre et al. | |
| 4,902,502 | A | 2/1990 | Nitecki et al. | |
| 5,089,261 | A | 2/1992 | Nitecki et al. | |
| 5,206,344 | A | 4/1993 | Katre et al. | |
| 6,706,289 | B2 | 3/2004 | Lewis et al. | |
| 7,585,837 | B2 | 9/2009 | Schechter et al. | |
| 8,377,917 | B2 * | 2/2013 | Hersel | A61K 47/64 514/183 |
| 8,618,124 | B2 | 12/2013 | Greenwald et al. | |
| 8,754,190 | B2 | 6/2014 | Ashley et al. | |
| 8,946,405 | B2 | 2/2015 | Ashley et al. | |
| 9,266,938 | B2 * | 2/2016 | Ast | C12N 15/62 |
| 9,272,048 | B2 * | 3/2016 | Rau | A61K 38/27 |
| 9,428,567 | B2 | 8/2016 | Garcia et al. | |
| 9,511,122 | B2 * | 12/2016 | Rasmussen | A61K 47/12 |
| 9,561,285 | B2 * | 2/2017 | Rau | A61P 29/00 |
| 10,799,563 | B2 * | 10/2020 | Kurpiers | A61K 47/26 |
| 10,835,578 | B2 * | 11/2020 | Rau | A61K 47/60 |
| 11,879,001 | B2 | 1/2024 | Gunnarsson et al. | |
| 2006/0269515 | A1 | 11/2006 | Denis-Mize et al. | |
| 2011/0091413 | A1 * | 4/2011 | Epstein | A61P 31/18 424/85.2 |
| 2012/0035101 | A1 | 2/2012 | Fares et al. | |
| 2014/0328791 | A1 * | 11/2014 | Bossard | A61P 35/00 435/254.2 |
| 2017/0224777 | A1 | 8/2017 | Wittrup et al. | |
| 2021/0008168 | A1 * | 1/2021 | Knappe | C07K 1/1077 |
| 2023/0174605 | A1 | 6/2023 | Gunnarsson et al. | |
| 2023/0201355 | A1 | 6/2023 | Gunnarsson et al. | |
| 2023/0340055 | A1 | 10/2023 | Okkels et al. | |

FOREIGN PATENT DOCUMENTS

| | | | |
|---|---|---|---|
| AU | 2017359841 | B2 | 8/2020 |
| CN | 111018961 | A | 4/2020 |
| EP | 1 534 334 | B1 | 2/2004 |
| EP | 1 536 334 | | 6/2005 |
| JP | 2007-530485 | A | 11/2007 |
| JP | 2014-506793 | A | 3/2014 |
| JP | 2017-535609 | A | 11/2017 |
| WO | WO 99/60128 | | 11/1999 |
| WO | WO 02/00243 | | 1/2002 |
| WO | WO 02/089789 | | 11/2002 |
| WO | WO 03/015697 | | 2/2003 |
| WO | WO 2005/027978 | | 3/2005 |
| WO | WO 2005/086751 | A2 | 9/2005 |
| WO | WO 2005/086798 | A2 | 9/2005 |
| WO | WO 2005/099768 | A2 | 10/2005 |

(Continued)

OTHER PUBLICATIONS

Harris, K.E., Lorentsen, K.J., Malik-Chaudhry, H.K. et al. A bispecific antibody agonist of the IL-2 heterodimeric receptor preferentially promotes in vivo expansion of CD8 and NK cells. Sci Rep 11, 10592 (2021). (Year: 2021).*

Charych et al., NKTR-214, an engineered cytokine with biased IL2 receptor binding, increased tumor exposure, and marked efficacy in mouse tumor models. Clin. Cancer Res. (2016), 22:3, p. 680-690.*

Bowie et al., "Deciphering the Message in Protein Sequences: Tolerance to Amino Acid Substitutions", Science (1990), 1306-1310, vol. 247.

Charych et al., "NKTR-214 an Engineered Cytokine with Biased IL2 Receptor Binding, Increased Tumor Exposure, and Marked Efficacy in Mouse Tumor Models", Clinical Cancer Research Feb. 1, 2016, 680-690, vol. 22(3).

(Continued)

*Primary Examiner* — Joanne Hama
*Assistant Examiner* — Jami Michelle Gurley
(74) *Attorney, Agent, or Firm* — Alston & Bird LLP

(57) ABSTRACT

The present invention relates to IL-2 conjugates, a pharmaceutically acceptable salt thereof, pharmaceutical compositions comprising such IL-2 conjugate or a pharmaceutically acceptable salt thereof and their uses.

23 Claims, No Drawings

Specification includes a Sequence Listing.

(56) References Cited

FOREIGN PATENT DOCUMENTS

| | | | | |
|---|---|---|---|---|
| WO | WO 2006/069246 | | 6/2006 | |
| WO | WO 2008/034122 | | 3/2008 | |
| WO | WO 2008/155134 | | 12/2008 | |
| WO | WO 2009/009712 | | 1/2009 | |
| WO | WO 2009/095479 | | 8/2009 | |
| WO | WO 2009/133137 | A2 | 11/2009 | |
| WO | WO 2009/143412 | | 11/2009 | |
| WO | WO 2010/085495 | A1 | 7/2010 | |
| WO | WO 2010/091122 | | 8/2010 | |
| WO | WO 2011/08611 | | 2/2011 | |
| WO | WO 2011/08612 | | 2/2011 | |
| WO | WO 2011/08613 | | 2/2011 | |
| WO | WO 2011/012715 | | 2/2011 | |
| WO | WO 2011/063770 | A2 | 6/2011 | |
| WO | WO-2011073234 | A2 * | 6/2011 | ............. A61K 38/27 |
| WO | WO 2011/082368 | | 7/2011 | |
| WO | WO 2011/144756 | | 11/2011 | |
| WO | WO 2012/002047 | | 5/2012 | |
| WO | WO 2012/065086 | | 5/2012 | |
| WO | WO-2012065086 | A1 * | 5/2012 | ......... A61K 38/2013 |
| WO | WO 2012/107417 | A1 | 8/2012 | |
| WO | WO 2013/024048 | | 2/2013 | |
| WO | WO 2013/036857 | | 3/2013 | |
| WO | WO 2014/028748 | A1 | 2/2014 | |
| WO | WO 2014/056923 | | 4/2014 | |
| WO | WO 2014/056926 | | 4/2014 | |
| WO | WO 2014/060512 | | 4/2014 | |
| WO | WO 2014/100014 | A1 | 6/2014 | |
| WO | WO 2015/042707 | A1 | 4/2015 | |
| WO | WO-2015125159 | A1 * | 8/2015 | ......... A61K 38/2013 |
| WO | WO 2016/020373 | | 2/2016 | |
| WO | WO 2016/025385 | A1 | 2/2016 | |
| WO | WO 2016/079114 | | 5/2016 | |
| WO | WO-2016079114 | A1 * | 5/2016 | ............. A61K 38/27 |
| WO | WO 2017/148883 | A1 | 9/2017 | |
| WO | WO-2018060311 | A1 * | 4/2018 | ............. A61K 38/29 |
| WO | WO 2018/091003 | A1 | 5/2018 | |
| WO | WO 2018/175788 | | 9/2018 | |
| WO | WO 2019/028419 | A1 | 2/2019 | |
| WO | WO 2019/091384 | A1 | 5/2019 | |
| WO | WO 2019/131964 | A1 | 7/2019 | |
| WO | WO 2019/185705 | A1 | 10/2019 | |
| WO | WO 2020/020783 | A1 | 1/2020 | |
| WO | WO 2020/057646 | A1 | 3/2020 | |
| WO | WO 2020/0242884 | A1 | 12/2020 | |
| WO | WO 2020/254607 | A1 | 12/2020 | |
| WO | WO 2021/245130 | A1 | 12/2021 | |
| WO | WO 2022/043493 | A1 | 3/2022 | |

OTHER PUBLICATIONS

Anonymous, Supplemental data to CHARYCH et al., "NKTR-214 an Engineered Cytokine with Biased IL2 Receptor Binding, Increased Tumor Exposure, and Marked Efficacy in Mouse Tumor Models" Jan. 1, 2016, retrieved from URL: http://clincancerres.aacrjournals.org/content/suppl/2016/01/29/22.3.680.DC1.

Goodson et al., "Site-Directed Pegylation of Recombinant Interleukin-2 at its Glycosylation Site", Biotechnology. The International Monthly for Industrial Biology, Nature Publishing Group, Apr. 1990, 343-346, vol. 8(4).

Jones et al., "Polymeric Dibromomaleimides As Extremely Efficient Disulfide Bridging Bioconjugation and Pegylation Agents", J.Am. Chem, Soc., (2012), 1847-1852, vol. 134(3).

Levin et al., "Exploiting A Natural Conformational Switch To Engineer An Interleukin-2 'Superkine'", Nature Oct. 26, 2012, 529-533, vol. 484(7395).

Sato et al., "Further Studies on the Site-Specific Protein Modification by Microbial Transglutaminase", Bioconjugate Chem. 2001, 701-710, vol. 12(5).

Tystsikov et al., Identification and Characterization of Two Alternative Splice Variants of Human Interleukin-2, The Journal of Biological Chemistry, Sep. 20, 1996, 23055-23060, vol. 271(38).

Vazquez-Lombardi et al., "Molecular Engineering of Therapeutic Cytokines", Antibodies Jul. 7, 2013, 426-451, vol. 2(3).

"Human mature IL-2 protein mutant R38C.", Geneseq Aug. 22, 2019 (Aug. 22, 2019), retrieved from EBI accession No. GSP:BGM81672 Database accession No. BGM81672 XP002800682.

Beresov, B.F. Korovkin Bilogical chemistry, M., "Medicine", 1998, p. 34 third paragraph, p. 59 last paragraph), English translation.

Dyson, May p. "Chemistry of synthetic drugs" translated from English—M.: Mir, 1964, p. 12-19), English Translation.

Popular medical encyclopedia, chief editor V. I. Pokrovskij, fourth edition, "KNIGOČEJ", 1997, p. 317 (drugs), English Translation.

PCT Application No. PCT/EP2021/064781, PCT Written Opinion of the International Searching Authority mailed Aug. 5, 2021.

WIPO Application No. PCT/EP2019/057709, PCT International Preliminary Report on Patentability mailed Sep. 29, 2020.

WIPO Application No. PCT/EP2019/057709, PCT International Search Report mailed Aug. 16, 2019.

WIPO Application No. PCT/EP2021/064781, PCT International Preliminary Report on Patentability mailed Dec. 6, 2022.

U.S. Appl. No. 17/997,363, filed Oct. 27, 2022, Gunnarsson et al.

U.S. Appl. No. 18/043,319, filed Feb. 27, 2023, Okkels et al.

U.S. Appl. No. 18/052,495, filed Nov. 3, 2022, Gunnarsson et al.

Carmenate et al., "Human IL-2 mutein with higher antitumor efficacy than wild type IL-2," The Journal of Immunology, vol. 190, No. 12, pp. 630-6238, (Jun. 2013).

Grabenhorst et al., "Biosynthesis and secretion of human interleukin 2 glycoprotein variants from baculovirus-infected Sf21 Cells," European Journal of Biochemistry, vol. 215, No. 1, pp. 189-197, (Jul. 1993).

U.S. Appl. No. 18/052,495, Non-Final Office Action mailed Jun. 7, 2023.

WIPO Application No. PCT/EP2021/073735, PCT International Preliminary Report on Patentability mailed Feb. 28, 2023.

WIPO Application No. PCT/EP2021/073735, PCT International Search Report mailed Dec. 21, 2021.

U.S. Appl. No. 18/052,495, Corrected Notice of Allowance mailed Oct. 13, 2023.

U.S. Appl. No. 18/052,495, Final Office Action mailed Jul. 27, 2023.

U.S. Appl. No. 18/052,495, Notice of Allowance mailed Sep. 27, 2023.

Charych et al., "Modeling the receptor pharmacology, pharmacokinetics, and pharmacodynamics of NKTR-214, a kinetically-controlled interleukin-2 (IL2) receptor agonist for cancer immunotherapy," PLoS ONE 12(7): e0179431, (Jul. 2017).

Zhang et al., "Protein-drug conjugate programmed by pH-reversible linker for tumor hypoxia relief and enhanced cancer combination therapy," International Journal of Pharmaceutics, 582, 119321, (Apr. 2020).

U.S. Appl. No. 17/997,363, Non-Final Office Action mailed Jan. 30, 2025.

* cited by examiner

IL-2 CONJUGATES

The present invention relates to IL-2 conjugates, a pharmaceutically acceptable salt thereof, pharmaceutical compositions comprising such IL-2 conjugate or a pharmaceutically acceptable salt thereof and their uses.

In healthy humans, the immune system can often discriminate between healthy cells and cancerous cells. Upon identifying a given cell as cancerous, the immune system typically eliminates it. However, when the immune system is compromised from e.g. acute or chronic defects or is overwhelmed, cancers can develop resulting from a compromised immune system's inability to differentiate, and then eliminate, cancer cells. In a patient suffering from cancer, administration of an immunomodulatory protein to the patient may help activate that patient's immune system so that the immune system's ability to eliminate cancer cells is enhanced. In this way, the cancer may be slowed from further growth, suppressed from potential spread or even eliminated.

One such immunomodulatory protein used in the treatment of patients suffering from certain cancers is interleukin-2. Interleukin-2 (IL-2) is a naturally occurring cytokine that has activity as both a stimulator of natural killer cells (NK cells) and T-cell proliferation and functional activity. IL-2 plays a central role in the generation, differentiation, survival and homeostasis of immune effector cells. IL-2 is synthesized by activated CD4+ helper T cells, and through differential receptor interaction IL-2 can modulate the immune response towards immunity or tolerance.

IL-2 acts by binding to IL-2 receptors (IL-2R). Association of the α-(CD25), β-(CD122) and common γ- (γc, CD132) subunits results in the trimeric high-affinity IL-2R. The dimeric intermediate affinity IL-2Rβγ consists of the β- and γ-subunits and binds IL-2 with 50-fold lower affinity. CD25 is not required for IL-2 signaling, but confers the high affinity binding of the trimeric receptor, whereas the β- and γ-subunits mediate signal transduction. IL-2Rβγ is expressed on NK cells, monocytes, macrophages and resting CD4+ and CD8+ T cells, while IL-2Rαβγ is transiently induced on activated T and NK cells, and is constitutively expressed on T regulatory cells. The ability of IL-2 to expand and activate innate and adaptive effector cells is the basis of its antitumor activity.

In patients, IL-2 can stimulate antitumor efficacy, characterized by increases in cytotoxic lymphocytes, including effector T and NK cells, when given at high-doses (i.e., 600 000-720 000 IU/kg body weight three times daily for up to 14 doses per cycle in humans). Presumably during this therapy all T cells are stimulated by IL-2 after high-doses are administered and when the therapy cycle ends and IL-2 levels drop at some point IL-2 will be come limiting and and T regulatory (Treg) cells expressing IL-2Rαβγ will outcompete effector T cells expressing IL-2Rβγ for the remaining wild type IL-2.

Aldesleukin, recombinant human IL-2, was the first cancer immunotherapy approved by the FDA in 1992. With use of appropriate supportive care, aldesleukin has demonstrated complete cancer regression in about 10% of patients treated for metastatic melanoma and renal cancer. Approximately 70% of patients with complete responses have been cured, maintaining complete regression for more than 25 years after initial treatment.

Based on its antitumor efficacy, high-dose IL-2 (aldesleukin) has been approved for patients with metastatic renal cell carcinoma and malignant melanoma. However, its antitumor immunity is dose limited by severe cardiovascular, pulmonary, hepatic, gastrointestinal, neurologic and hematological side effects, such that it is only given to patients at specialized centers. Also, once administered IL-2 levels fall below the levels required for IL-2Rβγ activity, activation of Tregs expressing high affinity IL-2Rαβγ will be favored, which can limit anti-tumor immunity Preclinical experiments showed that IL-2-induced pulmonary edema (as a model of vascular leak syndrome) can be caused by interaction of IL-2 with CD25 on lung endothelial cells and that it can be abrogated by a CD25 blocking antibody, genetic disruption, or the use of IL-2-antibody complexes. Another proposed mechanism by which IL-2 induces vascular leak syndrome involves activation of Eosinophils as these cells can express IL-2Rαβγ and IL-2 therapy in patients is associated with elevated systemic Eosinophils and IL-5 levels.

CD4+ regulatory T-cells (Treg cells), which are responsible for suppressing the immune response leading to immune tolerance, preferentially express the IL-2Rαβγ form of the IL-2R. Thus, administration of compounds that bind to and are agonists for IL-2Rαβγ can be expected to suppress the immune response and hereby also interfere with anti-tumor responses in cancer patients.

Effector CD4+ T cells, CD8+ T-cells and NK cells, which significantly enhance anti-tumor immune responses, preferentially express the IL-2Rβγ form of the IL-2R. Thus, administration of compounds that are binds to and are agonists for IL-2Rβγ can be expected to enhance the immune response against tumors (by, e.g., increasing the proliferation and activity of effect of CD4+ T cells, CD8+ T-cells and NK cells).

Thus, administration of IL-2Rβγ-selective agonists (having reduced or no binding to IL-2Rα or enhanced binding to IL-2Rβγ) would be beneficial to patients suffering from certain cancers as doing so is expected to reduce systemic vascular leak side effects such as pulmonary edema, providing an improved therapeutic window. Also, IL-2Rβγ-selective agonists would have the benefit of avoiding the selective activation of immune-suppressing regulatory T-cells at low doses and would be similarly potent against Tregs and CD4+ effector T cells, cytotoxic CD8+ effector T-cells and NK cells, thereby providing more opportunity to augmenting the patient's immune system to eliminate cancer cells.

Optimally, such an IL-2Rβγ-selective agonist would also exhibit relatively long exposure following administration, thereby further improving the patient's response to the treatment. Boosting the effector arm of the immune system in the cancer patient via administration of IL-2βγ-selective agonists, can be further enhanced through the administration of antagonists of immunosuppressive pathways (e.g., antagonists of CTLA-4 and PD-1) or through administration of immune agonists such as TLR ligands, or agents which agonize immune activating receptors such as 41BB (CD137), OX40, ICOS, CD40, CD28, NKG2D, NKp30, NKp44, NKp46, LFA1, CD16, CD64, CD32A and CD3.activating receptor agonists, or Antibody Directed Cellular Cytotoxicity (ADCC) engaging antibodies.

Adoptive transfer of tumor-reactive T cells has evolved into a clinically useful therapy capable of inducing antitumor immunity in patients. However, the broad application of adoptive T cell transfer (ACT) therapies to treat cancer has several limitations, including the production of sufficient quantities of cells for infusion and the failure of transferred T cells to persist and remain functional in vivo. In the clinic, the concomitant administration of the T cell growth factor interleukin-2 (IL-2) improves the survival, function, and antitumor activity of transplanted T cells. However, the use of IL-2 to potentiate ACT is complicated by the pleiotropic nature of IL-2, which induces both immune stimulatory and suppressive T cell responses as well as potentially severe toxicities.

Attempts at addressing the toxicity concerns of IL-2 have been made. In one case, formulation approaches have been attempted, see, for example, U.S. Pat. No. 6,706,289 and international patent application publication WO 02/00243 and WO 99/60128. In other approaches, certain conjugates of IL-2 have been suggested, see, for example, U.S. Pat. Nos. 4,766,106, 5,206,344, 5,089,261 and 4,902,502. In addition, certain reversible conjugates of IL-2 have been suggested, see for example WO12065086A1.

Notwithstanding these approaches, however, there remains a need for conjugates of IL-2 that provide safer treatments for cancer patients.

It is therefore an object of the present invention to at least partially overcome the above-mentioned disadvantage.

This object is achieved with an IL-2 conjugate or a pharmaceutically acceptable salt thereof of formula (Ia) or (Ib)

$$Z\text{—}(L^2\text{—}L^1\text{—}D)_x \quad \text{(Ia)}$$

$$D\text{—}(L^1\text{—}L^2\text{—}Z)_y, \quad \text{(Ib)}$$

wherein

-D is a biased IL-2 moiety, which biased IL-2 moiety comprises an IL-2 moiety and for which biased IL-2 moiety the ratio of the $K_D$ of said biased IL-2 to IL-2Rαβ to the $K_D$ of said biased IL-2 to IL-2Rβ is larger than the ratio of the $K_D$ of aldesleukin to IL-2Rαβ to the $K_D$ of aldesleukin to IL-2Rβ;

-$L^1$- is a linker moiety covalently and reversibly attached to -D;

-$L^2$- is a chemical bond or is a spacer moiety;

—Z is a polymeric moiety or a substituted fatty acid moiety;

x is an integer selected from the group consisting of 1, 2, 3, 4, 5, 6, 7, 8, 9, 10, 11, 12, 13, 14, 15 or 16; and y is an integer selected from the group consisting of 2, 3, 4 and 5.

Within the present invention the terms are used with the meaning as follows:

The term "interleukin-2" or "IL-2" as used herein, refers to all IL-2 proteins, preferably from mammalian species, more preferably from primate species and most preferably from human, as well as their variants, analogs, orthologs, homologs, and derivatives and fragments thereof, that are characterized by playing a central role in lymphocyte generation, survival and homeostasis. The term "IL-2" also encompasses naturally occurring variants of IL-2, e.g. splice variants or allelic variants.

Human IL-2 has the sequence of SEQ ID NO:1:

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT

Unprocessed human IL-2 additionally comprises an N-terminal 20 amino acid signal peptide, which is absent in the mature IL-2 molecule.

Preferably and unless otherwise specified the term "IL-2" preferably refers to aldesleukin, i.e. to a variant of human IL-2, in which the amino acid at position 1 (alanine) present in human IL-2 of SEQ ID NO:1 has been deleted (desA1) and the cysteine present in human IL-2 of SEQ ID NO:1 at position 125 was exchanged for serine (C125S). The sequence of aldesleukin is shown in SEQ ID NO:2:

PTSSSTKKTQLQLEHLLLDLQMILNGINNYKNPKLTRMLTFKFYMPKKAT

ELKHLQCLEEELKPLEEVLNLAQSKNFHLRPRDLISNINVIVLELKGSET

TFMCEYADETATIVEFLNRWITFSQSIISTLT

As used herein, the term "IL-2 protein variant" or "IL-2 variant" refers to a protein from the same species that differs from a reference IL-2 protein. Preferably, such reference IL-2 protein sequence is the sequence of SEQ ID NO:2. Generally, differences are limited so that the amino acid sequence of the reference and the variant are closely similar overall and, in many regions, identical. Preferably, IL-2 protein variants are at least 70%, 80%, 90%, or 95% identical to a reference IL-2 protein, preferably the IL-2 protein of SEQ ID NO:2. By a protein having an amino acid sequence at least, for example, 95% "identical" to a query amino acid sequence, it is intended that the amino acid sequence of the subject protein is identical to the query sequence except that the subject protein sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Preferably, the query sequence is the sequence of SEQ ID NO:2.

Such IL-2 protein variants may be naturally occurring variants, such as naturally occurring allelic variants encoded by one of several alternate forms of an IL-2 occupying a given locus on a chromosome or an organism, or isoforms encoded by naturally occurring splice variants originating from a single primary transcript. Alternatively, an IL-2 protein variant may be a variant that is not known to occur naturally and that can be made by mutagenesis techniques known in the art.

It is known in the art that one or more amino acids may be deleted from the N-terminus or C-terminus of a bioactive peptide or protein or from internal positions, i.e. a position between the N- and the C-terminal amino acid, without substantial loss of biological function. Such N-terminal, C-terminal and/or internal deletions are also encompassed by the term IL-2 protein variant.

It is also recognized by one of ordinary skill in the art that some amino acid sequences of IL-2 proteins can be varied without significant effect of the structure or function of the peptide. Such mutants include deletions, insertions, inversions, repeats, and substitutions selected according to general rules known in the art to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

As used herein, the term “IL-2 analog” refers to IL-2 of different and unrelated organisms which perform the same functions in each organism, but which did not originate from an ancestral structure that the organisms’ ancestors had in common. Instead, analogous IL-2 arose separately and then later evolved to perform the same or similar functions. In other words, analogous IL-2 proteins are proteins with quite different amino acid sequences but that perform the same biological activity.

As used herein the term “IL-2 ortholog” refers to IL-2 within two different species which sequences are related to each other via a common homologous IL-2 in an ancestral species, but which have evolved to become different from each other.

As used herein, the term “IL-2 homolog” refers to IL-2 of different organisms which perform the same functions in each organism and which originate from an ancestral structure that the organisms’ ancestors had in common. In other words, homologous IL-2 proteins are proteins with quite similar amino acid sequences that perform the same biological activity. Preferably, IL-2 protein homologs may be defined as proteins exhibiting at least 40%, 50%, 60%, 70%, 80%, 90% or 95% identity to a reference IL-2 protein, preferably the IL-2 protein of SEQ ID NO:2.

As used herein, the term “IL-2 protein fragment” refers to any peptide comprising a contiguous span of a part of the amino acid sequence of a IL-2 protein, preferably the protein of SEQ ID NO:2. More specifically, an IL-2 protein fragment comprises at least 50, such as at least 60, at least 70 or at least 80 consecutive amino acids of an IL-2 protein, more preferably of the protein of SEQ ID NO:2.

The term “IL-2” also includes poly(amino acid) conjugates which have a sequence as described above, but having a backbone that comprises both amide and non-amide linkages, such as ester linkages, like for example depsipeptides. Depsipeptides are chains of amino acid residues in which the backbone comprises both amide (peptide) and ester bonds. Accordingly, the term “side chain” as used herein refers either to the moiety attached to the alpha-carbon of an amino acid moiety, if the amino acid moiety is connected through amine bonds such as in peptides or proteins, or to any carbon atom-comprising moiety attached to the backbone of a poly(amino acid) conjugate, such as for example in the case of depsipeptides. Preferably, the term “IL-2” refers to proteins having a backbone formed through amide (peptide) bonds.

As the term IL-2 includes the above-described variants, analogs, orthologs, homologs, derivatives and fragments of IL-2, all references to specific positions within a reference sequence also include the equivalent positions in these variants, analogs, orthologs, homologs, derivatives and fragments of a IL-2 moiety, even if not specifically mentioned.

As used herein, the term “biased IL-2” refers to a modified IL-2, in which the ratio of the $K_D$ of said biased IL-2 to IL-2Rαβ to the $K_D$ of said biased IL-2 to IL-2Rβ is larger than the ratio of the $K_D$ of aldesleukin of SEQ ID NO:2 to IL-2Rαβ to the $K_D$ of aldesleukin to IL-2Rβ. This is described by the following formula:

$$\frac{Ratio_{biased\ IL\text{-}2}}{Ratio_{aldesleukin}} > 1$$

wherein

-continued $$Ratio_{biased\ IL\text{-}2} = \frac{K_D \text{ biased } IL\text{-}2 \text{ to } IL\text{-}2R\alpha\beta}{K_D \text{ biased } IL\text{-}2 \text{ to } IL\text{-}2\beta}$$

$$Ratio_{aldesleukin} = \frac{K_D \text{ aldesleukin to } IL\text{-}2R\alpha\beta}{K_D \text{ aldesleukin to } IL\text{-}2\beta}$$

with

“$K_D$ biased IL-2 to IL-2Rαβ” being the $K_D$ of biased IL-2 to IL-2Rαβ,

“$K_D$ biased IL-2 to IL-2Rαβ” being the $K_D$ of biased IL-2 to IL-2Rβ,

“$K_D$ aldesleukin to IL-2Rαβ” being the $K_D$ of aldesleukin to IL-2Rαβ, and

“$K_D$ aldesleukin to IL-2Rβ” being the $K_D$ of aldesleukin to IL-2Rβ.

Binding affinity/kinetics needed to determine the $K_D$ of biased IL-2 to IL-2Rαβ, the $K_D$ Of biased IL-2 to IL-2Rβ, the $K_D$ of aldesleukin to IL-2Rαβ and the $K_D$ of aldesleukin to IL-2Rβ may be assessed using surface plasmon resonance (SPR), measured on a Biacore instrument (GE Healthcare) as follows: A human Fc capture surface on a CM5 (or alternatively C1 or CM4) chip is prepared by covalent coating with anti-human Fc antibody or alternatively a protein A chip is used. Next, IL-2Rβ-Fc or a suitable mixture of IL2-Rα-Fc and IL2-Rβ-Fc, such as a 1:1 mixture, is immobilized on the chip. To measure the affinity/kinetic constants, serial dilutions of the analytes are made starting at for example between 1.5 nM and 2 μM or at 100 nM and 1 μM for IL-2 compounds (ending at for example 0.03 nM to 100 nM or 0.1 nM to 1 nM). Analytes are each exposed to the receptor-modified chip for a suitable amount of time, such as for 1 to 30 minutes, which may for example be 2 minutes or may be 3 minutes and are then washed away for a suitable amount of time, such as 2 to 60 minutes, which may for example be 10 minutes. The resulting binding curves from the dilution series are fit to a 1:1 kinetic model to correlate observed response units (R) to the association and dissociation rate constants, $k_a$ and $k_d$:

$$R = \frac{k_a C R_{max}}{k_a C + k_d} \times (1 - e^{-(k_a C + k_d)t})$$

wherein t is time;

C is the concentration of the analyte; and $R_{max}$ is the maximum binding capacity of the surface.

If determined via a kinetic 1:1 model the ratio of the dissociation and association rates provides the equilibrium dissociation constant $K_D$.

Alternatively, the resulting binding curves from the dilution series are fit to a 1:1 steady state interaction model which calculates $K_D$ for a 1:1 interaction from a plot of steady-state binding levels ($R_{eq}$) against analyte concentration (C):

$$R_{eq} = \frac{C \times R_{max}}{K_D + C}$$

wherein $R_{eq}$ is the steady-state binding level;

C is the concentration of the analyte; and $R_{max}$ is the maximum binding capacity of the surface.

It is understood that not every calculation method may be possible for every biased IL-2 molecule. If, for example, the reactions are too fast, it may not be possible to use a 1:1 kinetic model and a 1:1 steady state interaction model may be used. If, for example, no equilibrium is obtained, it may not be possible to use a 1:1 interaction model and a 1:1 kinetic model may be used.

It is understood that the $K_D$ of the biased IL-2 to IL2Rαβ and IL2Rβ is measured for the biased IL-2 and not for the IL-2 conjugate of the present invention. Thus, $K_D$ measurement occurs in the absence of a moiety $-L^1-$, $-L^2-$ and —Z and preferably before the IL-2 conjugate of the present invention is synthesized, except when the IL-2 conjugate is a translational fusion protein, in which case $K_D$ is measured after the biased IL-2 is released, such as after protease cleavage or chemical cleavage.

Such biased IL-2 comprises a protein portion, which is an IL-2 moiety, preferably an IL-2 moiety having the amino acid sequence of SEQ ID NO:2, which comprises at least one amino acid mutation or at least one deletion or at least one modifying moiety $M_{mod}$, such as 1, 2, 3, 4, 5, 6, 7, 8, 9 and 10 modifying moieties $M_{mod}$, or any combination thereof. A moiety $M_{mod}$ may be a protein moiety or a non-protein moiety. If the biased IL-2 comprises more than one moiety $M_{mod}$ these may be the same or different. In certain embodiments the IL-2 moiety has the sequence of SEQ ID NO: 1.

In the IL-2 conjugates of the present invention the biased IL-2 is present in the form of the corresponding biased IL-2 moiety and the IL-2 conjugates of the present invention release biased IL-2 upon release of all moieties —Z, i.e. upon cleavage of the reversible linkage between the biased IL-2 moiety, i.e. -D, and $-L^1-$.

As used herein, the term "affinity" refers to the strength of the sum of non-covalent interactions between a single binding site of a molecule (such as a receptor) and its binding partner (such as a ligand). Unless indicated otherwise, as used herein, "affinity" refers to intrinsic binding affinity which reflects a 1:1 interaction between members of a binding pair (such as between a receptor and a ligand). The affinity of a molecule X for its partner Y can generally be represented by the equilibrium dissociation constant ($K_D$), which is the ratio of dissociation and association rate constants ($k_d$ and $k_a$, respectively) measured in a state of equilibrium. Thus, equivalent affinities may comprise different rate constants, as long as the ratio of the rate constants remains the same. Affinity can be measured by well-established methods known in the art, including those described herein.

As used herein, the terms "α-subunit of the IL-2 receptor" and "IL-2Rα" refer to human CD25.

As used herein, the terms "β-subunit of the IL-2 receptor" and "IL-2Rβ" refer to human CD122.

As used herein, the terms "α- and β-subunit of the IL-2 receptor", "α- and β-subunit of IL-2R" and "IL-2Rαβ" refer to a mixture, such as a 1:1 mixture, of IL-2Rα and "IL-2Rβ.

The IL-2 conjugates of the present invention release biased IL-2, i.e. the IL-2 conjugates of the present invention are prodrugs of biased IL-2. As used herein the term "prodrug" refers to a biologically active moiety, such as a biased IL-2 moiety, reversibly and covalently connected to a specialized protective group through a linker moiety (which may also be referred to as a "reversible prodrug linker"), which linker moiety comprises a reversible linkage with the biologically active moiety and wherein the specialized protective group alters or eliminates undesirable properties in the parent molecule of the biologically active moiety, i.e. in the corresponding drug. This also includes the enhancement of desirable properties in the drug and the suppression of undesirable properties. The specialized non-toxic protective group is referred to as "carrier". A prodrug releases the reversibly and covalently bound biologically active moiety in the form of its corresponding drug. In other words, a prodrug is a conjugate comprising a biologically active moiety, which is covalently and reversibly conjugated to a carrier moiety via a reversible prodrug linker moiety, which covalent and reversible conjugation of the carrier to the reversible prodrug linker moiety is either directly or through a spacer moiety. Another term for "biologically active moiety" is "drug moiety".

As used herein, the term "reversible", "reversibly", "degradable" or "degradably" with regard to the attachment of a first moiety to a second moiety means that the linkage that connects said first and second moiety is cleavable under physiological conditions, which are aqueous buffer at pH 7.4, 37° C., with a half-life ranging from one hour to three months, preferably from one hour to two months, even more preferably from one hour to one month. Cleavage may be enzymatically or non-enzymatically and is preferably non-enzymatically. Accordingly, the term "stable" or "permanent" with regard to the attachment of a first moiety to a second moiety means that the linkage that connects said first and second moiety is cleavable with a half-life of more than three months under physiological conditions.

As used herein, the term "modifying moiety" preferably refers to a substituent or a polymeric moiety.

As used herein, the term "disulfide bridging" refers to the insertion of a moiety between the two sulfur atoms of a disulfide bridge. This is achieved by using a reagent that has said moiety between two thiol-reactive functional groups and reacting each thiol-reactive functional group with one of the sulfur atoms of the disulfide bridge, such that the moiety is inserted between said sulfur atoms after foregone reduction of the disulfide bond. If more than one disulfide bridge is present in a peptide or protein, the disulfide bridge may either be inserted between the sulfur atoms of one disulfide bridge or may be inserted between the sulfur atoms from different disulfide bridges. Such disulfide bridge may be naturally occurring in a peptide or protein or may have been artificially introduced, for example by replacing existing amino acid moieties with or by adding cysteine moieties to a peptide or protein.

As used herein, the term "reagent" means a chemical compound, which comprises at least one functional group for reaction with the functional group of another chemical compound or drug. It is understood that a drug comprising a functional group (such as a primary or secondary amine or hydroxyl functional group) is also a reagent.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a biologically active moiety is released from a reversible linkage as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N($R^1$)—" can be attached to two moieties or interrupting a moiety either as "—C(O)N(R$^1$)—" or as "—N(R$^1$)C(O)—". Similarly, a moiety

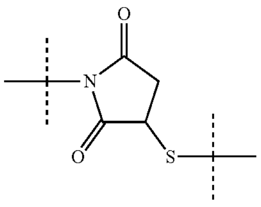

can be attached to two moieties or can interrupt a moiety either as

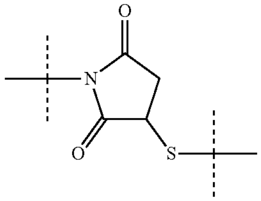 or as 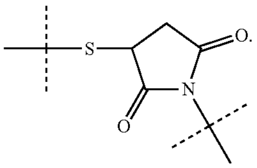

The term "substituted" as used herein means that one or more —H atom(s) of a molecule or moiety are replaced by a different atom or a group of atoms, which are referred to as "substituent".

As used herein, the term "substituent" refers preferably to a moiety selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$—OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$ and —OC(O)N(R$^{x3}$);

—R$^{x1}$, —R$^{x1a}$, —R$^{x1b}$ are independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$);

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (═O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4}$a —N(R$^{x4}$)C(O)N(R$^{x4a}$R$^{x4}$), —OC(O)N(R$^{x4}$R$^{x4a}$), and C$_{1-6}$ alkyl; wherein C$_{1-6}$ alkyl is optionally substituted with one or more halogen, which are the same or different;

each —R$^{x3}$, —R$^{x3a}$, —R$^{x4}$, —R$^{x4a}$, —R$^{x4b}$ is independently selected from the group consisting of —H and C$_{1-6}$ alkyl; wherein C$_{1-6}$ alkyl is optionally substituted with one or more halogen, which are the same or different.

Preferably, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

As used herein, the term "fatty acid" refers to a saturated or unsaturated monocarboxylic acid having an aliphatic tail, which may include from 4 to 28 carbon atoms. The fatty acid may be saturated or unsaturated, linear or branched. The term "fatty acid variant" refers to a modified fatty acid in which certain carbon atoms may be replaced by other atoms or groups of atoms and which may be substituted.

The term "peptide" as used herein refers to a chain of at least 2 and up to and including 50 amino acid monomer moieties linked by peptide (amide) linkages. The term "peptide" also includes peptidomimetics, such as D-peptides, peptoids or beta-peptides, and covers such peptidomimetic chains with up to and including 50 monomer moieties.

As used herein, the term "protein" refers to a chain of more than 50 amino acid monomer moieties, which may also be referred to as "amino acid residues", linked by peptide linkages, in which preferably no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein the term "about" in combination with a numerical value is used to indicate a range ranging from and including the numerical value plus and minus no more than 25% of said numerical value, more preferably no more than 20% of said numerical value and most preferably no more than 10% of said numerical value. For example, the phrase "about 200" is used to mean a range ranging from and including 200+/−25%, i.e. ranging from and including 150 to 250; preferably 200+/−20%, i.e. ranging from and including 160 to 240; even more preferably ranging from and including 200+/−10%, i.e. ranging from and including 180 to 220. It is understood that a percentage given as "about 50%" does not mean "50%+/−25%", i.e. ranging from and including 25 to 75%, but "about 50%" means ranging from and including 37.5 to 62.5%, i.e. plus and minus 25% of the numerical value which is 50.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical group(s) and/or moiety/moieties, such as, for example, one or more functional group(s). Likewise, it is understood that also a peptide or protein is a polymer, even though the side chains of individual amino acid residues may be different. Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferably has a molecular weight of at most 1000 kDa, such as at most 750 kDa, such as at most 500 kDa, such as at most 300 kDa, such as at most 200 kDa, such as at most 100 kDa. It is understood that for insoluble polymers, such as hydrogels, no meaningful molecular weight ranges can be provided.

As used herein, the term "polymeric" means a reagent or a moiety comprising one or more polymer(s) or polymer moiety/moieties. A polymeric reagent or moiety may optionally also comprise one or more other moiety/moieties, which are preferably selected from the group 30 consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

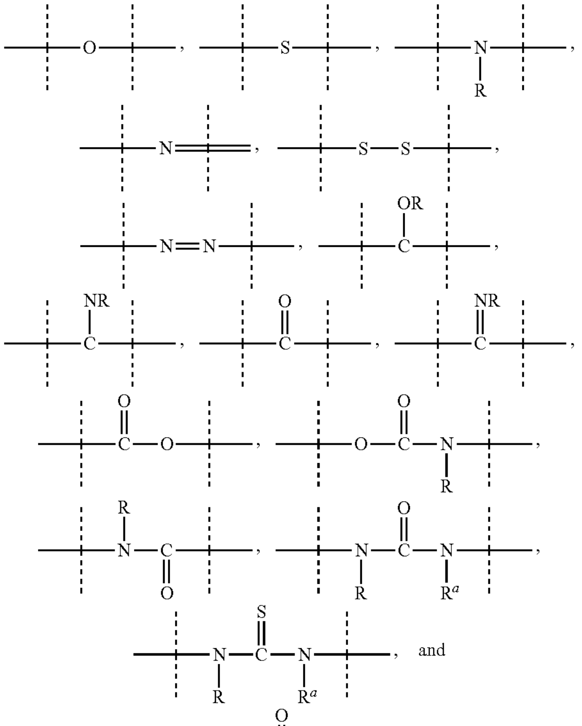

and

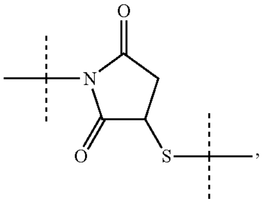

, wherein dashed lines indicate attachment to the remainder of the moiety or reagent, and —R and —$R^a$ are independently of each other selected from the group consisting of —H, methyl, ethyl, propyl, butyl, pentyl and hexyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−25%, preferably x+/−20% and more preferably x+/−10%.

As used herein, the term "number average molecular weight" means the ordinary arithmetic mean of the molecular weights of the individual polymers.

As used herein, the term "PEG-based" in relation to a moiety or reagent means that said moiety or reagent comprises PEG. Preferably, a PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60 (w/w) PEG, such as at least 70% (w/w) PEG, such as at least 80% (w/w) PEG, such as at least 90% (w/w) PEG, such as at least 95%. The remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

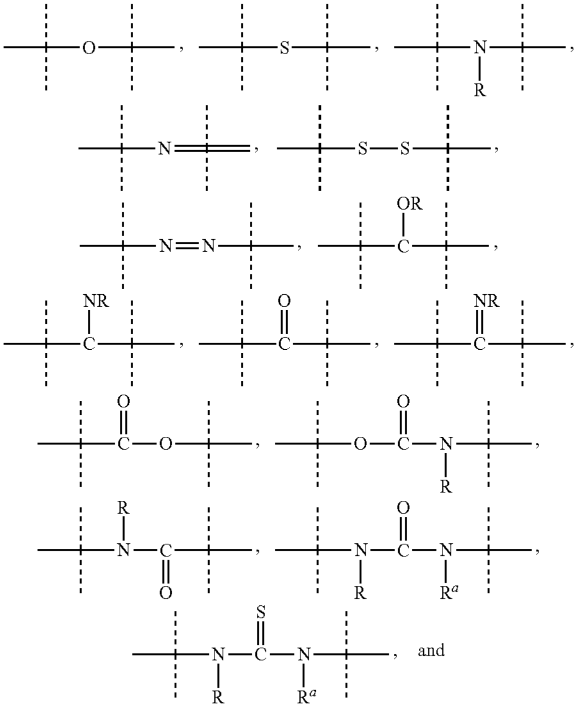

and

-continued

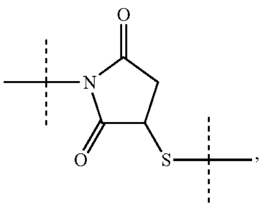

wherein dashed lines indicate attachment to the remainder of the moiety or reagent, and —R and —$R^a$ are independently of each other selected from the group consisting of —H, methyl, ethyl, propyl, butyl, pentyl and hexyl.

The term "hyaluronic acid-based" is used accordingly.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

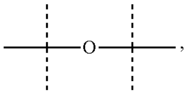, 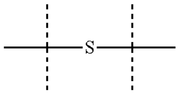, 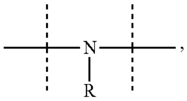,

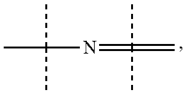, 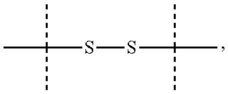,

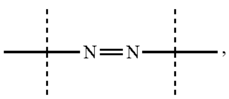, 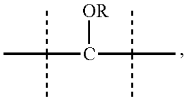,

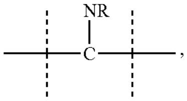, 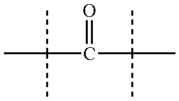, 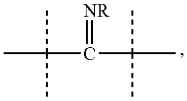,

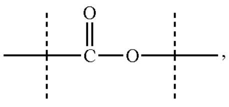, 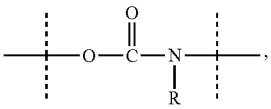,

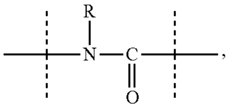, 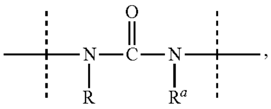,

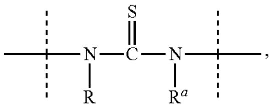, and

-continued

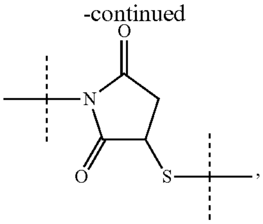

wherein dashed lines indicate attachment to the remainder of the moiety or reagent, and —R and —$R^a$ are independently of each other selected from the group consisting of —H, methyl, ethyl, propyl, butyl, pentyl and hexyl.

The term "hyaluronic acid-based comprising at least X % hyaluronic acid" is used accordingly.

As used herein, the term "hydrogel" means a hydrophilic or amphiphilic polymeric network composed of homopolymers or copolymers, which is insoluble due to the presence of hydrophobic interactions, hydrogen bonds, ionic interactions and/or covalent chemical crosslinks. The crosslinks provide the network structure and physical integrity.

The term "interrupted" means that a moiety is inserted between two carbon atoms or—if the insertion is at one of the moiety's ends—between a carbon or heteroatom and a hydrogen atom, preferably between a carbon and a hydrogen atom.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —$CH_2$—, —$CH_2$—$CH_2$—, —$CH(CH_3)$—, —$CH_2$—$CH_2$—$CH_2$—, —$CH(C_2H_5)$—, —$C(CH_3)_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, $H_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH═CH$_2$, —CH═CH—CH$_3$, —CH$_2$—CH═CH$_2$, —CH═CHCH$_2$—CH$_3$ and —CH═CH—CH═CH$_2$. When two moieties of a molecule are linked by the $C_{2-6}$ alkenyl group, then an example for such $C_{2-6}$ alkenyl is —CH═CH—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means a straight-chain or branched hydrocarbon moiety comprising at least one carbon-carbon triple bond having 2 to 6 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkenyl or $C_{2-50}$ alkynyl may optionally be interrupted by one or more moieties which are preferably selected from the group consisting of

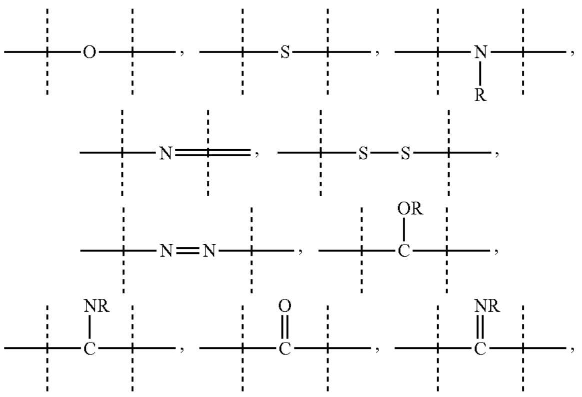

-continued

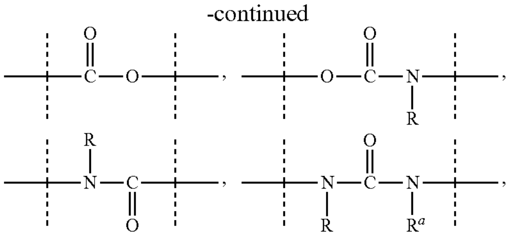

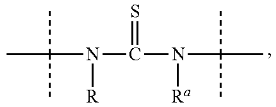

and

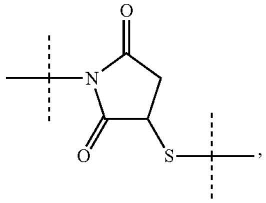

wherein dashed lines indicate attachment to the remainder of the moiety or reagent; and —R and —R$^a$ are independently of each other selected from the group consisting of —H, and methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norborane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including ═N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term “8- to 11-membered heterobicyclyl” or “8- to 11-membered heterobicycle” means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term “8- to 30-membered heteropolycyclyl” or “8- to 30-membered heteropolycycle” means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —$S(O)_2$—), oxygen and nitrogen (including =N(O)—) and wherein the ring is linked to the rest of a molecule via a carbon or nitrogen atom.

It is understood that the phrase “the pair R/$R^Y$ is joined together with the atom to which they are attached to form a $C_{3-10}$ cycloalkyl or a 3- to 10-membered heterocyclyl” in relation with a moiety of the structure

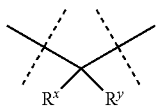

means that $R^x$ and $R^y$ form the following structure:

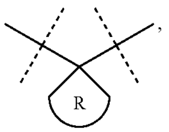

wherein R is $C_{3-10}$ cycloalkyl or 3- to 10-membered heterocyclyl.

It is also understood that the phrase “the pair $R^x$/$R^y$ is joint together with the atoms to which they are attached to form a ring A” in relation with a moiety of the structure

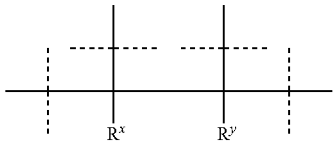

means that $R^x$ and $R^y$ form the following structure:

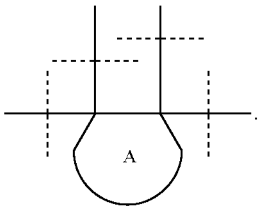

As used herein, “halogen” means fluoro, chloro, bromo or iodo. It is generally preferred that halogen is fluoro or chloro.

As used herein, the term “functional group” means a group of atoms which can react with other groups of atoms. Exemplary functional groups are, for example, carboxylic acid (—(C=O)OH), primary or secondary amine (—$NH_2$, —NH—), maleimide, thiol (—SH), sulfonic acid (—(O=S=O)OH), carbonate, carbamate (—O(C=O)N<), hydroxyl (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the IL-2 conjugates of the present invention comprise one or more acidic or basic groups, the invention also comprises their corresponding pharmaceutically or toxicologically acceptable salts, in particular their pharmaceutically utilizable salts. Thus, the IL-2 conjugates of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. IL-2 conjugates of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the IL-2 conjugates of the present invention simultaneously comprise acidic and basic groups, the invention also includes, in addition to the salt forms mentioned, inner salts or betaines (zwitterions). The respective salts can be obtained by customary methods, which are known to the person skilled in the art like, for example by contacting these prodrugs with an organic or inorganic acid or base in a solvent or dispersant, or by anion exchange or cation exchange with other salts. The present invention also includes all salts of the IL-2 conjugates of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does not cause harm when administered to a patient and preferably means approved by a regulatory agency, such as the EMA (Europe) and/or the FDA (US) and/or any other national regulatory agency for use in animals, preferably for use in humans.

As used herein, the term "excipient" refers to a diluent, adjuvant, or vehicle with which the therapeutic, such as a drug or prodrug, is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or biologically active moiety, together with a suitable amount of excipient so as to provide the form for proper administration to the patient. The formulation should suit the mode of administration.

In general, the term "comprise" or "comprising" also encompasses "consist of" or "consisting of".

The ratio of $Ratio_{base\ IL\text{-}2}$ to $Ratio_{aldesleukin}$ is larger than 1, preferably larger than 2, preferably larger then 3, preferably larger than 4 and even more preferably larger than 5. In certain embodiments the ratio of $Ratio_{biased\ IL\text{-}2}$ to $Ratio_{aldesleukin}$ is larger than 10, larger than 20, larger than 50, larger than 70, larger than 100 or larger than 150.

The biased IL-2 moiety -D is an IL-2 moiety, preferably aldesleukin, comprising (a) at least one stable attachment of a modifying moiety $M_{mod}$, which may be the same or different; or (b) at least one amino acid mutation; or (c) at least one deletion; or any combination of (a), (b) and (c).

At least one of the modifications listed under (a), (b) and (c) is present in -D and ensures that the $Ratio_{base\ IL\text{-}2}$ is larger than the $Ratio_{aldesleukin}$ in the biased IL-2 moiety. However, it is understood that the IL-2 moiety may also comprise one or more of the modifications listed under (a), (b) and (c), which when viewed in isolation do not ensure that the $Ratio_{biased}$ IL-2 is larger than the $Ratio_{aldesleukin}$. Such additional modifications may for example provide improved production or storage characteristics of -D.

In one embodiment the biased IL-2 moiety comprises at least one stable attachment of a modifying moiety $M_{mod}$ to the IL-2 moiety. In another embodiment the biased IL-2 moiety comprises at least one amino acid mutation in the IL-2 moiety. In another embodiment the biased IL-2 moiety comprises at least one deletion in the IL-2 moiety. In another embodiment the biased IL-2 moiety comprises at least one stable attachment of a modifying moiety $M_{mod}$ to the IL-2 moiety and at least one amino acid mutation in the IL-2 moiety. In another embodiment the biased IL-2 moiety comprises at least one stable attachment of a modifying moiety $M_{mod}$ to the IL-2 moiety and at least one deletion in the IL-2 moiety. In another embodiment the biased IL-2 moiety comprises at least one amino acid mutation and at least one deletion in the IL-2 moiety. In another embodiment the biased IL-2 moiety comprises at least one stable attachment of a modifying moiety $M_{mod}$ to the IL-2 moiety, at least one amino acid mutation and at least one deletion in the IL-2 moiety.

The biased IL-2 moiety may comprise at least one stable attachment of a modifying moiety $M_{mod}$ to the IL-2 moiety. Attachment of $M_{mod}$ may be at the N-terminus, C-terminus, at an amino acid side chain or at an internal site of the IL-2 moiety. Such moiety $M_{mod}$ may preferably be a substituent or a polymeric moiety. In certain embodiments attachment of $M_{mod}$ is at the N-terminus of the IL-2 moiety. In certain embodiments attachment of $M_{mod}$ is at the C-terminus of the IL-2 moiety. In certain embodiments attachment of $M_{mod}$ is at an amino acid side chain of the IL-2 moiety. In certain embodiments attachment of $M_{mod}$ is at an internal site of the IL-2 moiety. If more than one moiety $M_{mod}$ is attached to the IL-2 moiety, attachment may occur at any combination of attachment sites selected from the group consisting of the N-terminus, C-terminus, a side chain of an amino acid residue and an internal site.

In one embodiment $M_{mod}$ is a substituent. Preferably, such substituent has a molecular weight ranging from 15 Da to 1 kDa.

Such moiety $M_{mod}$ may in one embodiment be introduced in the form of a disulfide bridging. Preferably, such disulfide bridging is formed between the thiol groups of two cysteine residues. Such disulfide bridging is one example for attachment of a modifying moiety at an internal site. In one embodiment these cysteine residues may be naturally occurring cysteine residues. In another embodiment, one or both of the cysteine residues do not naturally occur, but were added to or inserted into the IL-2 moiety, preferably the IL-2 moiety of SEQ ID NO:2, or replaced a naturally occurring amino acid residue of the IL-2 moiety, preferably the IL-2 moiety of SEQ ID NO:2.

Preferred ways of obtaining such disulfide bridging are disclosed in Jones et al. (J. Am. Chem. Soc., 2012, 134 (3), pp 1847-1852), WO2011/018611, WO2011/018612 and WO2011/018613.

Preferably such disulfide bridging occurs at a position that is involved in binding to IL-2Rα. Thus, preferably, the disulfide bridging results in a reduced affinity of the biased IL-2 moiety to IL-2Rαβ compared to aldesleukin.

In one embodiment the disulfide bridging is formed between C57 and C104, if the IL-2 moiety has the sequence of SEQ ID NO:2.

In another embodiment $M_{mod}$ is a polymeric moiety. Such polymeric moiety may comprise a linear, branched or multi-arm polymer. In one embodiment the polymer is a linear polymer. In another embodiment the polymer is a branched polymer. Such branched polymer preferably has one, two, three, four or five branching points. From each branching point preferably two, three or four polymer arms extend. In another embodiment the polymer is a multi-arm polymer. Such multi-arm polymer preferably has 3, 4, 5, 6, 7 or 8 polymeric arms.

If $M_{mod}$ is a polymeric moiety, such polymeric moiety preferably has a molecular weight ranging from 0.5 kDa to 1000 kDa, such as from 1 kDa to 1000 kDa, more preferably from 2 kDa to 500 kDa, even more preferably from 3 kDa to 200 kDa, most preferably from 5 kDa to 120 kDa or has a molecular weight ranging from 7 to 40 kDa. In one embodiment such polymer has a molecular weight of about 0.5 kDa. In one embodiment such polymer has a molecular weight of about 1 kDa. In one embodiment such polymer has a molecular weight of about 2 kDa. In one embodiment such polymer has a molecular weight of about 3 kDa. In one embodiment such polymer has a molecular weight of about 4 kDa. In one embodiment such polymer has a molecular weight of about 5 kDa. In one embodiment such polymer has a molecular weight of about 7.5 kDa. In another embodiment such polymeric moiety has a molecular weight of about 10 kDa. In another embodiment such polymeric moiety has a molecular weight of about 15 kDa. In another embodiment such polymeric moiety has a molecular weight of about 20 kDa. In another embodiment such polymeric moiety has a molecular weight of about 30 kDa. In another embodiment such polymeric moiety has a molecular weight of about 40 kDa. In another embodiment such polymeric moiety has a molecular weight of about 0 kDa. about In another embodiment such polymeric moiety has a molecular weight of about 70 kDa. In another embodiment such polymeric moiety has a molecular weight of about 80 kDa. In another embodiment such polymeric moiety has a molecular weight of about 90 kDa. In another embodiment such polymeric moiety has a molecular weight of about 100 kDa. In one embodiment such polymer has a molecular weight of 0.5 kDa. In one embodiment such polymer has a molecular weight of 1 kDa. In one embodiment such polymer has a molecular weight of 2 kDa. In one embodiment such polymer has a molecular weight of 3 kDa. In one embodiment such polymer has a molecular weight of 4 kDa. In one embodiment such polymer has a molecular weight of 5 kDa. In one embodiment such polymer has a molecular weight of 7.5 kDa. In another embodiment such polymeric moiety has a molecular weight of 10 kDa. In another embodiment such polymeric moiety has a molecular weight of 15 kDa. In another embodiment such polymeric moiety has a molecular weight of 20 kDa. In another embodiment such polymeric moiety has a molecular weight of 30 kDa. In another embodiment such polymeric moiety has a molecular weight of 40 kDa. In another embodiment such polymeric moiety has a molecular weight of 50 kDa. In another embodiment such polymeric moiety has a molecular weight of 70 kDa. In another embodiment such polymeric moiety has a molecular weight of 80 kDa. In another embodiment such polymeric moiety has a molecular weight of 90 kDa. In another embodiment such polymeric moiety has a molecular weight of 100 kDa.

If $M_{mod}$ is a polymeric moiety, such polymeric moiety preferably comprises a polymer selected from the group consisting of 2-methacryloyl-oxyethyl phosphoyl cholins, poly(acrylic acids), poly(acrylates), poly(acrylamides), poly (alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly (ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, alginate, mannans, pectins, rhamnogalacturonans, starches, hydroxyalkyl starches, hydroxyethyl starches and other carbohydrate-based polymers, xylans, and copolymers thereof.

In one embodiment $M_{mod}$ is a PEG-based polymer.

In another embodiment $M_{mod}$ is a hyaluronic acid-based polymer.

In another embodiment $M_{mod}$ comprises a peptide or protein moiety. In one embodiment such peptide or protein moiety $M_{mod}$ may be a translational fusion with the IL-2 moiety comprised in the biased IL-2. In another embodiment such peptide or protein moiety $M_{mod}$ may be chemically conjugated to the IL-2 moiety comprised in the biased IL-2. Preferably, this peptide or protein moiety $M_{mod}$ is not a fragment of IL-2 or an IL-2-moiety.

$M_{mod}$ in the form of a peptide or protein moiety may be a synthetic or natural protein moiety or a portion or variant thereof. Exemplary non-IL-2 moieties include albumin; antibody domains, such as Fc domains or antigen binding domains of immunoglobulins; CTP, and CD25; each either in their naturally occurring form or as a variant or fragment thereof.

A peptide or protein moiety $M_{mod}$ fused to the IL-2 moiety may be attached at the N-terminus or the C-terminus or may be inserted at an internal position of the IL-2 moiety. It is understood that more than one peptide or protein moiety $M_{mod}$ may be translationally fused or chemically conjugated to and/or inserted into the IL-2 moiety. Said more than one peptide or protein moiety $M_{mod}$ may have the same or a different sequence. For example, the biased IL-2 moiety may have a first peptide or protein moiety $M_{mod}$ translationally fused or chemically conjugated to the N-terminus of the IL-2 moiety and a second peptide or protein moiety $M_{mod}$ translationally fused or chemically conjugated to the C-terminus of the IL-2 moiety. In another example, the biased IL-2 moiety may comprise a first peptide or protein moiety $M_{mod}$ translationally fused or chemically conjugated to the N-terminus of the IL-2 moiety and a second peptide or protein moiety $M_{mod}$ translationally inserted into or chemically conjugated to an internal position of the IL-2 moiety. In another example, the biased IL-2 moiety may comprise a first peptide or protein moiety $M_{mod}$ translationally fused or chemically conjugated to the C-terminus of the IL-2 moiety and a second peptide or protein moiety $M_{mod}$ translationally inserted into or chemically conjugated to an internal position of the IL-2 moiety. In an even further example the biased IL-2 moiety may comprise a first peptide or protein moiety $M_{mod}$ translationally fused or chemically conjugated to the N-terminus of the IL-2 moiety, a second peptide or protein moiety $M_{mod}$ translationally fused or chemically conjugated to the C-terminus of the IL-2 moiety and a third peptide or protein moiety $M_{mo}$a translationally inserted into or chemically conjugated an internal position of the IL-2 moiety.

Attachment of $M_{mod}$ may be at a proteinogenic or non-proteinogenic amino acid residue of the IL-2 moiety. In certain embodiments attachment of $M_{mod}$ occurs to a proteinogenic amino acid. Such proteinogenic amino acid residue is preferably selected from the group consisting of cysteine, methionine, histidine, lysine, tryptophan, serine, threonine, tyrosine, aspartic acid, glutamic acid, glutamine and arginine. In certain embodiments attachment of $M_{mod}$ occurs to a non-proteinogenic amino acid. If the modifying moiety is attached to a non-proteinogenic amino acid residue, it is understood that such non-proteinogenic amino acid residue is artificially introduced into the IL-2 moiety. Such non-proteinogenic amino acid residue may be any non-proteinogenic amino acid residue having a functional group available for conjugating $M_{mod}$ to the IL-2 moiety. In certain embodiments such non-proteinogenic amino acids comprise a functional group in their side chains selected from the group consisting of carbonyl; carbonyl derivatives, such as carbonyl-like, marked carbonyl and protected carbonyl groups; azide; oxime; and hydroxylamine.

In certain embodiments such non-proteinogenic amino acid is a non-proteinogenic amino acid as described in WO2006/069246A2, which non-proteinogenic amino acids are incorporated by reference herewith. In certain embodiments the non-proteinogenic amino acid has a structure as described in formula (I) in [00265] to [00283], of formula (XXX) in [00284], of formula (XXX-A) in [00285], of formula (XXX-B) in [00286], of formula (XXXI) in [00287], of formula (XXXI-A) in [00288], of formula (XXXI-B) in [00289], of formula (XXXII) in [00290], of formula (XXXII-A) in [00291], of formula (XXXII-B) in [00292], of formula (XXXX) in [00293], of formula (XXXXI) in [00294], of formula (XXXXII) in erroneously labelled paragraph [0100], i.e. the paragraph between [00294] and [00295], of formula (XXXXIII) in [00295] and [00296], of formula (XIV) in [00302] to [00305], of formula (XV) in [00306] and [00307], of formula (XI) in [00310] to [00312], of formula (XII) in [00313], of formula (XII) in [00314] and [00315], of formula (XIV) in [00316], of formula (XVI) in [00317], of formula (XVI) in [00318] and [00319], of formula (XVIII) in [00320] and [00321], or of formula (XXIX) in [00530] of WO2006/069246A2, which non-proteinogenic amino acids are incorporated by reference herewith.

In one embodiment attachment of $M_{mod}$ occurs at a lysine residue of the IL-2 moiety, such as at a lysine residue selected from the group consisting of K7, K8, K31, K34, K42, K47, K48, K53, K63, K75 and K96 based on SEQ ID NO: 2 or at the corresponding positions of homologs or variants of SEQ ID NO:2. In case the homologs or variants of IL-2 comprise one or more additional lysine residues compared to SEQ ID NO:2 attachment may also occur at such additional lysine residues. It is understood that 1, 2, 3, 4, 5, 6, 7, 8, 9, 10 or 11 of the lysine residues of SEQ ID NO:2 may be used for attachment of $M_{mod}$. If the IL-2 moiety is a homolog or variant of SEQ ID NO:2 and comprises more lysine residues than the IL-2 moiety of SEQ ID NO:2, more than 11 lysine residues may be used for attachment of $M_{mod}$, i.e. up to the maximum number of lysine residues present in such homolog or variant of SEQ ID NO:2 may be used for attachment of $M_{mod}$. In one embodiment one moiety $M_{mod}$ is attached to one lysine residue of SEQ ID NO:2 or to a homolog or variant thereof. In another embodiment two moieties $M_{mod}$, which may be the same or different, are attached to two lysine residues of SEQ ID NO:2 or to a homolog or variant thereof. In another embodiment three moieties $M_{mod}$, which may be the same or different, are attached to three lysine residues of SEQ ID NO:2 or to a homolog or variant thereof. In another embodiment four moieties $M_{mod}$, which may be the same or different, are attached to four lysine residues of SEQ ID NO:2 or to a homolog or variant thereof. In another embodiment five moieties $M_{mod}$, which may be the same or different, are attached to five lysine residues of SEQ ID NO:2 or to a homolog or variant thereof. In another embodiment six moieties $M_{mod}$, which may be the same or different, are attached to six lysine residues of SEQ ID NO:2 or to a homolog or variant thereof.

In another embodiment attachment of $M_{mod}$ occurs at a threonine residue of the IL-2 moiety, such as at a threonine residue selected from the group consisting of T2, T6, T9, T36, T40, T50, T100, T101, T110, T112, T122, T130 and T132 based on SEQ ID NO: 2 or at the corresponding positions of homologs or variants of SEQ ID NO:2. In case the homologs or variants of IL-2 comprise one or more additional threonine residues compared to SEQ ID NO:2 attachment may also occur at such additional threonine residues. It is understood that 1, 2, 3, 4, 5, 6, 7, 8, 9, 10, 11, 12 or 13 of the threonine residues of SEQ ID NO:2 may be used for attachment of $M_{mod}$. If the IL-2 moiety is a homolog or variant of SEQ ID NO:2 and comprises more threonine residues than the IL-2 moiety of SEQ ID NO:2, more than 13 threonine residues may be used for attachment of $M_{mod}$, i.e. up to the maximum number of threonine residues present in such homolog or variant may be used for attachment of $M_{mod}$. In one embodiment one moiety $M_{mod}$ is attached to one threonine residue of SEQ ID NO:2 or to a homolog or variant thereof. In another embodiment two moieties $M_{mod}$, which may be the same or different, are attached to two threonine residues of SEQ ID NO:2 or to a homolog or variant thereof. In another embodiment three moieties $M_{mod}$, which may be the same or different, are attached to three threonine residues of SEQ ID NO:2 or to a homolog or variant thereof. In another embodiment four moieties $M_{mod}$, which may be the same or different, are attached to four threonine residues of SEQ ID NO:2 or to a homolog or variant thereof. In another embodiment five moieties $M_{mod}$, which may be the same or different, are attached to five threonine residues of SEQ ID NO:1 or to a homolog or variant thereof. In another embodiment six moieties $M_{mod}$, which may be the same or different, are attached to six threonine residues of SEQ ID NO:2 or to a homolog or variant thereof.

In another embodiment attachment of $M_{mod}$ occurs at a serine residue of the IL-2 moiety, such as at a serine residue selected from the group consisting of S3, S4, S5, S74, S86, S98, S124, S126 and S129 based on SEQ ID NO: 2 or at the corresponding positions of homologs or variants of SEQ ID NO:2. In case the homologs or variants of IL-2 comprise one or more additional serine residues compared to SEQ ID NO:2 attachment may also occur at such additional serine residues. It is understood that 1, 2, 3, 4, 5, 6, 7, 8 or 9 of the serine residues of SEQ ID NO:2 may be used for attachment of $M_{mod}$ s. If the IL-2 moiety is a homolog or variant of SEQ ID NO:2 and comprises more serine residues than the IL-2 moiety of SEQ ID NO:2, more than 9 serine residues may be used for attachment of $M_{mod}$, i.e. up to the maximum number of serine residues present in such homolog or variant may be used for attachment of $M_{mod}$. In one embodiment one moiety $M_{mod}$ is attached to one serine residue of SEQ ID NO:2 or to a homolog or variant thereof. In another embodiment two moieties $M_{mod}$, which may be the same or different, are attached to two serine residues of SEQ ID NO:2 or to a homolog or variant thereof. In another embodiment three moieties $M_{mod}$, which may be the same or different, are attached to three serine residues of SEQ ID NO:2 or to a homolog or variant thereof. In another embodiment four moieties $M_{mod}$, which may be the same or different, are attached to four serine residues of SEQ ID NO:2 or to a homolog or variant thereof. In another embodiment five moieties $M_{mod}$, which may be the same or different, are attached to five serine residues of SEQ ID NO:1 or to a homolog or variant thereof. In another embodiment six moieties $M_{mod}$, which may be the same or different, are attached to six serine residues of SEQ ID NO:2 or to a homolog or variant thereof.

In another embodiment attachment of $M_{mod}$ occurs at a tyrosine residue of the IL-2 moiety, such as at a tyrosine residue selected from the group consisting of Y30, Y44 and Y106 based on SEQ ID NO: 2 or at the corresponding positions of homologs or variants of SEQ ID NO:2. In case the homologs or variants of IL-2 comprise one or more additional tyrosine residues compared to SEQ ID NO:2 attachment may also occur at such additional tyrosine residues. It is understood that 1, 2 or 3 of the tyrosine residues of SEQ ID NO:2 may be used for attachment of $M_{mod}$. If the IL-2 moiety is a homolog or variant of SEQ ID NO:2 and comprises more tyrosine residues than the IL-2 moiety of SEQ ID NO:2, more than 3 tyrosine residues may be used for attachment of $M_{mod}$, i.e. up to the maximum number of tyrosine residues present in such homolog or variant may be used for attachment of $M_{mod}$. In one embodiment one moiety $M_{mod}$ is attached to one tyrosine residue of SEQ ID NO:2 or to a homolog or variant thereof. In another embodiment two moieties $M_{mod}$, which may be the same or different, are attached to two tyrosine residues of SEQ ID NO:2 or to a homolog or variant thereof. In another embodiment three moieties $M_{mod}$, which may be the same or different, are attached to three tyrosine residues of SEQ ID NO:2 or to a homolog or variant thereof.

In another embodiment attachment of $M_{mod}$ occurs at a histidine residue of the IL-2 moiety, such as at a histidine residue selected from the group consisting of H15, H54 and H78 based on SEQ ID NO: 2 or at the corresponding positions of homologs or variants of SEQ ID NO:2. In case the homologs or variants of IL-2 comprise one or more additional histidine residues compared to SEQ ID NO:2 attachment may also occur at such additional histidine residues. It is understood that 1, 2 or 3 of the histidine residues of SEQ ID NO:2 may be used for attachment of $M_{mod}$. If the IL-2 moiety is a homolog or variant of SEQ ID NO:2 and comprises more histidine residues than the IL-2 moiety of SEQ ID NO:2, more than 3 histidine residues may be used for attachment of $M_{mod}$, i.e. up to the maximum number of histidine residues present in such homolog or variant may be used for attachment of $M_{mod}$. In one embodiment one moiety $M_{mod}$ is attached to one histidine residue of SEQ ID NO:2 or to a homolog or variant thereof. In another embodiment two moieties $M_{mod}$, which may be the same or different, are attached to two histidine residues of SEQ ID NO:2 or to a homolog or variant thereof. In another embodiment three moieties $M_{mod}$, which may be the same or different, are attached to three histidine residues of SEQ ID NO:2 or to a homolog or variant thereof.

In another embodiment attachment of $M_{mod}$ occurs at a tryptophan residue of the IL-2 moiety, such as at the tryptophan residue at position W120 based on SEQ ID NO: 2 or at the corresponding position of homologs or variants of SEQ ID NO:2. In case the homologs or variants of IL-2 comprise one or more additional tryptophan residues compared to SEQ ID NO:2 attachment may also occur at such additional tryptophan residues. If the IL-2 moiety is a homolog or variant of SEQ ID NO:2 and comprises more tryptophan residues than the IL-2 moiety of SEQ ID NO:2, more than one tryptophan residue may be used for attachment of $M_{mod}$, i.e. up to the maximum number of tryptophan residues present in such homolog or variant may be used for attachment of $M_{mod}$. In one embodiment one moiety $M_{mod}$ is attached to one tryptophan residue of SEQ ID NO:2 or to a homolog or variant thereof.

In another embodiment attachment of $M_{mod}$ occurs at an aspartic acid residue of the IL-2 moiety, such as at an aspartic acid residue selected from the group consisting of D19, D83 and D108 based on SEQ ID NO: 2 or at the corresponding positions of homologs or variants of SEQ ID NO:2. In case the homologs or variants of IL-2 comprise one or more additional aspartic acid residues compared to SEQ ID NO:2 attachment may also occur at such additional aspartic acid residues. It is understood that 1, 2 or 3 of the aspartic acid residues of SEQ ID NO:2 may be used for attachment of $M_{mod}$. If the IL-2 moiety is a homolog or variant of SEQ ID NO:2 and comprises more aspartic acid residues than the IL-2 moiety of SEQ ID NO:2, more than 3 aspartic acid residues may be used for attachment of $M_{mod}$, i.e. up to the maximum number of aspartic acid residues present in such homolog or variant may be used for attachment of $M_{mod}$. In one embodiment one moiety $M_{mod}$ is attached to one aspartic acid residue of SEQ ID NO:2 or to a homolog or variant thereof. In another embodiment two moieties $M_{mod}$, which may be the same or different, are attached to two aspartic acid residues of SEQ ID NO:2 or to a homolog or variant thereof. In another embodiment three moieties $M_{mod}$, which may be the same or different, are attached to three aspartic acid residues of SEQ ID NO:2 or to a homolog or variant thereof.

In one embodiment attachment of $M_{mod}$ occurs at a glutamic acid residue of the IL-2 moiety, such as at a glutamic acid residue selected from the group consisting of E14, E51, E59, E60, E61, E66, E67, E94, E99, E105, E109 and E115 based on SEQ ID NO: 2 or at the corresponding positions of homologs or variants of SEQ ID NO:2. In case the homologs or variants of IL-2 comprise one or more additional glutamic acid residues compared to SEQ ID NO:2 attachment may also occur at such additional glutamic acid residues. It is understood that 1, 2, 3, 4, 5, 6, 7, 8, 9, 10, 11 or 12 of the glutamic acid residues of SEQ ID NO:2 may be used for attachment of $M_{mod}$. If the IL-2 moiety is a homolog or variant of SEQ ID NO:2 and comprises more glutamic acid residues than the IL-2 moiety of SEQ ID NO:2, more than 12 glutamic acid residues may be used for attachment of $M_{mod}$, i.e. up to the maximum number of glutamic acid residues present in such homolog or variant of SEQ ID NO:2 may be used for attachment of the one or more modifying moieties. In one embodiment one moiety $M_{mod}$ is attached to one glutamic acid residue of SEQ ID NO:2 or to a homolog or variant thereof. In another embodiment two moieties $M_{mod}$, which may be the same or different, are attached to two glutamic acid residues of SEQ ID NO:2 or to a homolog or variant thereof. In another embodiment three moieties $M_{mod}$, which may be the same or different, are attached to three glutamic acid residues of SEQ ID NO:2 or to a homolog or variant thereof. In another embodiment four moieties $M_{mod}$, which may be the same or different, are attached to four glutamic acid residues of SEQ ID NO:2 or to a homolog or variant thereof. In another embodiment five moieties $M_{mod}$, which may be the same or different, are attached to five glutamic acid residues of SEQ ID NO:2 or to a homolog or variant thereof. In another embodiment six moieties $M_{mod}$, which may be the same or different, are attached to six glutamic acid residues of SEQ ID NO:2 or to a homolog or variant thereof.

In another embodiment attachment of $M_{mod}$ occurs at an arginine residue of the IL-2 moiety, such as at an arginine residue selected from the group consisting of R37, R80, R82 and R119 based on SEQ ID NO:2 or at the corresponding positions of homologs or variants of SEQ ID NO:2. In case the homologs or variants of IL-2 comprise one or more additional arginine residues compared to SEQ ID NO:2 attachment may also occur at such additional arginine residues. It is understood that 1, 2, 3 or 4 of the arginine residues of SEQ ID NO:2 may be used for attachment of $M_{mod}$. If the IL-2 moiety is a homolog or variant of SEQ ID NO:2 and comprises more arginine residues than the IL-2 moiety of SEQ ID NO:2, more than 4 arginine residues may be used for attachment of $M_{mod}$, i.e. up to the maximum number of arginine residues present in such homolog or variant may be used for attachment of $M_{mod}$. In one embodiment one moiety $M_{mod}$ is attached to one arginine residue of SEQ ID NO:2 or to a homolog or variant thereof. In another embodiment two moieties $M_{mod}$, which may be the same or different, are attached to two arginine residues of SEQ ID NO:2 or to a homolog or variant thereof. In another embodiment three moieties $M_{mod}$, which may be the same or different, are attached to three arginine residues of SEQ ID NO:2 or to a homolog or variant thereof. In another embodiment four moieties $M_{mod}$, which may be the same or different, are attached to four arginine residues of SEQ ID NO:2 or to a homolog or variant thereof.

In another embodiment attachment of $M_{mod}$ occurs at a cysteine residue of the IL-2 moiety, such as at a cysteine residue selected from the group consisting of C57 and C104 based on SEQ ID NO:2 or at the corresponding positions of homologs or variants of SEQ ID NO:2. In case the homologs or variants of IL-2 comprise one or more additional cysteine residues compared to SEQ ID NO:2 attachment may also occur at such additional cysteine residues. It is understood that 1 or 2 of the cysteine residues of SEQ ID NO:2 may be used for attachment of $M_{mod}$. If the IL-2 moiety is a homolog or variant of SEQ ID NO:2 and comprises more cysteine residues than the IL-2 moiety of SEQ ID NO:2, more than 2 cysteine residues may be used for attachment of $M_{mod}$, i.e. up to the maximum number of cysteine residues present in such homolog or variant may be used for attachment of $M_{mod}$. In one embodiment one moiety $M_{mod}$ is attached to one cysteine residue of SEQ ID NO:2 or to a homolog or variant thereof. In another embodiment two moieties $M_{mod}$, which may be the same or different, are attached to two cysteine residues of SEQ ID NO:2 or to a homolog or variant thereof.

In another embodiment attachment of $M_{mod}$ occurs at an methionine residue of the IL-2 moiety, such as at an methionine residue selected from the group consisting of M22, M38, M45 and M103 based on SEQ ID NO: 2 or at the corresponding positions of homologs or variants of SEQ ID NO:2. In case the homologs or variants of IL-2 comprise one or more additional methionine residues compared to SEQ ID NO:2 attachment may also occur at such additional methionine residues. It is understood that 1, 2, 3 or 4 of the methionine residues of SEQ ID NO:2 may be used for attachment of the one or more modifying moieties. If the IL-2 moiety is a homolog or variant of SEQ ID NO:2 and comprises more methionine residues than the IL-2 moiety of SEQ ID NO:2, more than 4 methionine residues may be used for attachment of $M_{mod}$, i.e. up to the maximum number of methionine residues present in such homolog or variant may be used for attachment of $M_{mod}$. In one embodiment one moiety $M_{mod}$ is attached to one methionine residue of SEQ ID NO:2 or to a homolog or variant thereof. In another embodiment two moieties $M_{mod}$, which may be the same or different, are attached to two methionine residues of SEQ ID NO:2 or to a homolog or variant thereof. In another embodiment three moieties $M_{mod}$, which may be the same or different, are attached to three methionine residues of SEQ ID NO:2 or to a homolog or variant thereof. In another embodiment four moieties $M_{mod}$, which may be the same or different, are attached to four methionine residues of SEQ ID NO:2 or to a homolog or variant thereof.

In another embodiment attachment of $M_{mod}$ occurs at a glutamine residue of the IL-2 moiety, such as at a glutamine residue selected from the group consisting of Q10, Q12, Q21, Q56, Q73 and Q125 based on SEQ ID NO: 2 or at the corresponding positions of homologs or variants of SEQ ID NO:2. In case the homologs or variants of IL-2 comprise one or more additional glutamine residues compared to SEQ ID NO:2 attachment may also occur at such additional glutamine residues. It is understood that 1, 2, 3, 4, 5, 6, 7, 8 or 9 of the glutamine residues of SEQ ID NO:2 may be used for attachment of $M_{mod}$. If the IL-2 moiety is a homolog or variant of SEQ ID NO:2 and comprises more glutamine residues than the IL-2 moiety of SEQ ID NO:2, more than 6 glutamine residues may be used for attachment of $M_{mod}$, i.e. up to the maximum number of glutamine residues present in such homolog or variant may be used for attachment of $M_{mod}$. In one embodiment one moiety $M_{mod}$ is attached to one glutamine residue of SEQ ID NO:2 or to a homolog or variant thereof. In another embodiment two moieties $M_{mod}$, which may be the same or different, are attached to two glutamine residues of SEQ ID NO:2 or to a homolog or variant thereof. In another embodiment three moieties $M_{mod}$, which may be the same or different, are attached to three glutamine residues of SEQ ID NO:2 or to a homolog or variant thereof. In another embodiment four moieties $M_{mod}$, which may be the same or different, are attached to four glutamine residues of SEQ ID NO:2 or to a homolog or variant thereof. In another embodiment five moieties $M_{mod}$, which may be the same or different, are attached to five glutamine residues of SEQ ID NO:2 or to a homolog or variant thereof. In another embodiment six residues $M_{mod}$, which may be the same or different, are attached to six glutamine residues of SEQ ID NO:2 or to a homolog or variant thereof.

It is understood that in certain embodiments the biased IL-2 moiety may have moieties $M_{mod}$ attached to more than one type of amino acid residue, such as to a cysteine and to a lysine. Attachment of $M_{mod}$ to the IL-2 moiety is via a stable covalent linkage. In certain embodiments the linkage between the IL-2 moiety and a moiety $M_{mod}$ is via an amide. In certain embodiments the linkage between the IL-2 moiety and a moiety $M_{mod}$ is via a moiety

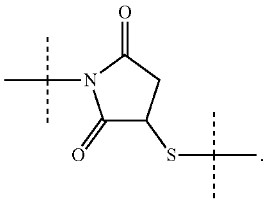

Preferably, attachment of at least one moiety $M_{mod}$ occurs at an amino acid position of the IL-2 moiety known to be involved in binding to IL-2Rα. Thus, preferably, attachment of at least one moiety $M_{mod}$ results in a substantially reduced affinity of the IL-2 moiety, preferably of a variant of the IL-2 moiety of SEQ ID NO:2, to IL-2Rαβ compared to aldesleukin, i.e. results in a biased IL-2 moiety.

Preferably attachment of $M_{mod}$ occurs at an amino acid position selected from the group consisting of K34, R37, M38, T40, F41, K42, F43, Y44, E61, and L71, based on SEQ ID NO:2 or at the corresponding positions of homologs or variants thereof. Even more preferably attachment of $M_{mod}$ occurs at an amino acid position selected from the group consisting of F41, Y44, E61 and L71 based on SEQ ID NO:2 or at the corresponding positions of homologs and variants thereof. It is understood that not all of these amino acid positions comprise a functional group that would allow direct conjugation of $M_{mod}$ and that certain steps may be necessary prior to attaching $M_{mod}$ at these amino acid positions, such as for example replacing the naturally occurring amino acid with a different amino acid or performing certain chemical modifications. Accordingly, attachment of $M_{mod}$ may occur in these positions either at the naturally occurring amino acid or at an amino acid that replaced the naturally occurring amino acid at that particular position and the attachment site may be a proteinogenic or non-proteinogenic amino acid, embodiments of both are as describe above. In certain embodiments attachment of $M_{mod}$ occurs at amino acid position K34 based on SEQ ID NO:2 or the corresponding position of homologs or variants thereof. In certain embodiments attachment of $M_{mod}$ occurs at amino acid position R37 based on SEQ ID NO:2 or the corresponding position of homologs or variants thereof. In certain embodiments attachment of $M_{mod}$ occurs at amino acid position M38 based on SEQ ID NO:2 or the corresponding position of homologs or variants thereof. In certain embodiments attachment of $M_{mod}$ occurs at amino acid position T40 based on SEQ ID NO:2 or the corresponding position of homologs or variants thereof. In certain embodiments attachment of $M_{mod}$ occurs at amino acid position F41 based on SEQ ID NO:2 or the corresponding position of homologs or variants thereof. In certain embodiments attachment of $M_{mod}$ occurs at amino acid position K42 based on SEQ ID NO:2 or the corresponding position of homologs or variants thereof. In certain embodiments attachment of $M_{mod}$ occurs at amino acid position F43 based on SEQ ID NO:2 or the corresponding position of homologs or variants thereof. In certain embodiments attachment of $M_{mod}$ occurs at amino acid position Y44 based on SEQ ID NO:2 or the corresponding position of homologs or variants thereof. In certain embodiments attachment of $M_{mod}$ occurs at amino acid position E61 based on SEQ ID NO:2 or the corresponding position of homologs or variants thereof. In certain embodiments attachment of $M_{mod}$ occurs at amino acid position L71 based on SEQ ID NO:2 or the corresponding position of homologs or variants thereof.

In certain embodiments $M_{mod}$ is of formula (A-1)

(A-1)

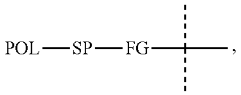

wherein

-FG- is a linkage;

-SP- is a spacer moiety; and

-POL is a polymer.

In certain embodiments -FG- of formula (A-1) is

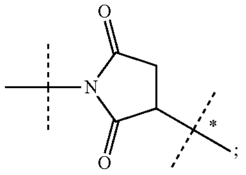

wherein the dashed line marked with the asterisk indicates attachment to a sulfur of the IL-2 moiety and the unmarked dashed line indicates attachment -SP-. Said sulfur may be a sulfur provided by the side chain of a cysteine.

In certain embodiments -FG- of formula (A-1) is

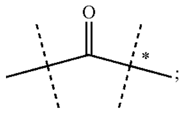

wherein the dashed line marked with the asterisk indicates attachment to a nitrogen of the IL-2 moiety and the unmarked dashed line indicates attachment to -SP-. Said nitrogen may be a nitrogen from the N-terminal amine or a nitrogen of the side chain of a lysine of the IL-2 moiety. In certain embodiments said nitrogen is the nitrogen of the N-terminal amine of the IL-2 moiety. In certain embodiments such nitrogen is a nitrogen of a side chain of a lysine of the IL-2 moiety.

In certain embodiments -FG- of formula (A-1) is

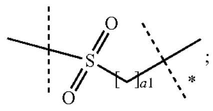

wherein the dashed line marked with the asterisk indicates attachment to a sulfur of nitrogen of the IL-2 moiety; the unmarked dashed line indicates attachment to -SP- and a1 is selected from the group consisting of 1, 2, 3, 4, 5, 6, 7, 8, 9, 10, 11, 12, 13, 14, 15, 16, 17, 18, 19 and 20. Said sulfur may be a sulfur provided by the side chain of a cysteine and said nitrogen may be a nitrogen from the N-terminal amine or a nitrogen of the side chain of a lysine of the IL-2 moiety. In certain embodiments the dashed line marked with the asterisk indicates attachment to a sulfur, which sulfur is provided by the side chain of a cysteine. In certain embodiments a1 is an integer ranging from 1 to 8. In certain embodiments a1 is an integer ranging from 1 to 6. In certain embodiments a1 is an integer ranging from 1 to 4. In certain embodiments a1 is 1. In certain embodiments a1 is 2. In certain embodiments a1 is 3. In certain embodiments a1 is 4. In certain embodiments a1 is 5. In certain embodiments a1 is 6.

In certain embodiments -FG- of formula (A-1) is

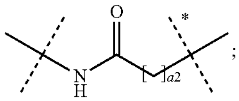

;

wherein the dashed line marked with the asterisk indicates attachment to a sulfur of nitrogen of the IL-2 moiety; the unmarked dashed line indicates attachment to -SP-; and a2 is an integer selected from the group consisting of 1, 2, 3, 4, 5, 6, 7, 8, 9, 10, 11, 12, 13, 14, 15, 16, 17, 18, 19 and 20. In certain embodiments a2 is an integer ranging from 1 to 8. In certain embodiments a2 is an integer ranging from 1 to 6. In certain embodiments a2 is an integer ranging from 1 to 4. In certain embodiments a2 is 1. In certain embodiments a2 is 2. In certain embodiments a2 is 3. In certain embodiments a2 is 4. In certain embodiments a2 is 5. In certain embodiments a2 is 6. Said sulfur may be a sulfur provided by the side chain of a cysteine and said nitrogen may be a nitrogen from the N-terminal amine or a nitrogen of the side chain of a lysine of the IL-2 moiety. In certain embodiments the dashed line marked with the asterisk indicates attachment to a sulfur, which sulfur is provided by the side chain of a cysteine.

In certain embodiments -SP- of formula (A-1) is selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $R^9$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{10}$)—, —$S(O)_2N(R^{10})$—, —S(O)N($R^{10}$)—, —$S(O)_2$—, —S(O)—, —$N(R^{10})S(O)_2N(R^{10a})$—, —S—, —N($R^{10}$)—, —OC($OR^{10}$)($R^{10a}$)—, —N($R^{10}$)C(O)N($R^{10a}$)—, and —OC(O)N($R^{10}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^9$, which are the same or different;

each —$R^9$ is independently selected from the group consisting of halogen, —CN, oxo (═O), —$COOR^{11}$, —$OR^{11}$, —C(O)$R^{11}$, —C(O)N($R^{11}R^{11a}$), —$S(O)_2N(R^{11}R^{11a})$, —S(O)N($R_{11}R^{11a}$), —$S(O)_2R^{11}$, —S(O)$R^{11}$, —$N(R^{11})S(O)_2N(R^{11a}R^{11b})$, —$SR^{11}$, —N($R^{11}R^{11a}$), —$NO_2$, —OC(O)$R^{11}$, —N($R^{11}$)C(O)$R^{11a}$, —$N(R^{11})S(O)_2R^{11a}$, —N($R^{11}$)S(O)$R^{11a}$, —N($R^{11}$)C(O)$OR^{11a}$, —N($R^{11}$)C(O)N($R^{11a}R^{11b}$), —OC(O)N($R^{11}R^{11a}$), and $C_{1-6}$ alkyl; wherein $C_{1-6}$ alkyl is optionally substituted with one or more halogen, which are the same or different; and each —$R^{10}$, —$R^{10a}$, —$R^{11}$, —$R^{11a}$ and —$R^{11b}$ is independently selected from the group consisting of —H, and $C_{1-6}$ alkyl, wherein $C_{1-6}$ alkyl is optionally substituted with one or more halogen, which are the same or different.

In certain embodiments -SP- of formula (A-1) is $C_{1-20}$ alkyl, which $C_{1-20}$ alkyl is optionally substituted with one or more —$R^9$, and which $C_{1-20}$ alkyl is optionally interrupted by one or more groups selected from the group consisting of —O—, —C(O)N($R^{10}$)—, —$S(O)_2$—, —S(O)—, —S—, —N($R^{10}$)—, —OC($OR^{10}$)($R^{10a}$)—, —N($R^{10}$)C(O)N($R^{10a}$), and —OC(O)N($R^{10}$)—; wherein each —$R^9$ is selected from the group consisting of $C_{1-6}$ alkyl; and each —$R^{10}$ and —$R^{10a}$ is independently selected from the group consisting of —H and $C_{1-6}$ alkyl.

In certain embodiments -SP- of formula (A-1) is $C_{1-10}$ alkyl, which $C_{1-10}$ alkyl is optionally substituted with one or more —$R^9$, and which $C_{1-10}$ alkyl is optionally interrupted by one or more groups selected from the group consisting of —O—, —C(O)N($R^{10}$)—, —$S(O)_2$—, —S(O)—, —S—, —N($R^{10}$)—, —OC($OR^{10}$)($R^{10a}$)—N($R^{10}$)C(O)N($R^{10a}$)—, and —OC(O)N($R^{10}$)—; wherein each —$R^9$ is selected from the group consisting of $C_{1-6}$ alkyl; and each —$R^{10}$ and —$R^{10a}$ is independently selected from the group consisting of —H and $C_{1-6}$ alkyl.

In certain embodiments -POL of formula (A-1) is a PEG-based polymer. In certain embodiments -POL is of formula (A-1i)

(A-1i)

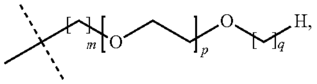

wherein the dashed line indicates attachment to -SP-;

m is 0 or 1;

p is an integer ranging from 12 to 22700; and q is selected from the group consisting of 1, 2, 3, 4, 5, and 6.

In certain embodiments m of formula (A-1i) is 0. In certain embodiments m of formula (A-1i) is 1.

In certain embodiments p of formula (A-1i) is an integer ranging from 23 to 227000, such as from 45 to 11300, or from 69 to 4540, or from 114 to 2700. In certain embodiments p of formula (A-1i) is about 12. In certain embodiments p of formula (A-1i) is about 23. In certain embodiments p of formula (A-1i) is about 46. In certain embodiments p of formula (A-1i) is about 68. In certain embodiments p of formula (A-1i) is about 90. In certain embodiments p of formula (A-1i) is about 112. In certain embodiments p of formula (A-1i) is about 170. In certain embodiments p of formula (A-1i) is about 227. In certain embodiments p of formula (A-1i) is about 340. In certain embodiments p of formula (A-1i) is about 450. In certain embodiments p of formula (A-1i) is about 680. In certain embodiments p of formula (A-1i) is about 900. In certain embodiments p of formula (A-1i) is about 1130. In certain embodiments p of formula (A-1i) is about 1350. In certain embodiments p of formula (A-1i) is about 1590. In certain embodiments p of formula (A-1i) is about 1800. In certain embodiments p of formula (A-1i) is about 2045. In certain embodiments p of formula (A-1i) is about 2275.

In certain embodiments q of formula (A-1i) is 1. In certain embodiments q of formula (A-1i) is 2. In certain embodiments q of formula (A-1i) is 3. In certain embodiments q of formula (A-1i) is 4. In certain embodiments q of formula (A-1i) is 5. In certain embodiments q of formula (A-1i) is 6.

In certain embodiments -POL of formula (A-1) is of formula (A-1ii)

(A-1ii)

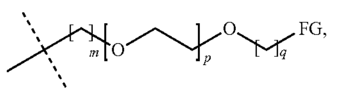

wherein the dashed line indicates attachment to -SP-;

FG is a functional group;

m is 0 or 1;

p is an integer ranging from 12 to 22700; and q is selected from the group consisting of 1, 2, 3, 4, 5, and 6.

If the moiety $M_{mod}$ of formula (A-1) is to be conjugated to further moieties, such as to one or more moieties $-L^1-L^2-Z$, it is advantageous if a moiety -POL ends with a functional group. It is understood the if -POL is of formula (A-1ii), such compound is a reagent and that after conjugation of such one or more moieties, such as one or more moieties $-L^1-L^2-Z$, to the functional group of said reagent, FG is no longer present, but has formed a linkage with a suitable functional group present in the reagent form of the one or more further moieties.

It is also understood that also other attachment sites for moieties to be conjugated to $M_{mod}$, such as moieties $-L^1-L^2-Z$, may be possible.

In certain embodiments m of formula (A-1ii) is 0. In certain embodiments m of formula (A-1ii) is 1.

In certain embodiments p of formula (A-1ii) is an integer ranging from 23 to 227000, such as from 45 to 11300, or from 69 to 4540, or from 114 to 2700. In certain embodiments p of formula (A-1ii) is about 12. In certain embodiments p of formula (A-1ii) is about 23. In certain embodiments p of formula (A-1ii) is about 46. In certain embodiments p of formula (A-1ii) is about 68. In certain embodiments p of formula (A-1ii) is about 90. In certain embodiments p of formula (A-1ii) is about 112. In certain embodiments p of formula (A-1ii) is about 170. In certain embodiments p of formula (A-1ii) is about 227. In certain embodiments p of formula (A-1ii) is about 340. In certain embodiments p of formula (A-1ii) is about 450. In certain embodiments p of formula (A-1ii) is about 680. In certain embodiments p of formula (A-1ii) is about 900. In certain embodiments p of formula (A-1ii) is about 1130. In certain embodiments p of formula (A-1ii) is about 1350. In certain embodiments p of formula (A-1ii) is about 1590. In certain embodiments p of formula (A-1ii) is about 1800. In certain embodiments p of formula (A-1ii) is about 2045. In certain embodiments p of formula (A-1ii) is about 2275.

In certain embodiments q of formula (A-1ii) is 1. In certain embodiments q of formula (A-1ii) is 2. In certain embodiments q of formula (A-1ii) is 3. In certain embodiments q of formula (A-1ii) is 4. In certain embodiments q of formula (A-1ii) is 5. In certain embodiments q of formula (A-1ii) is 6.

If a further moiety, such as a moiety $-L^1-L^2-Z$, is conjugated to $M_{mod}$ via a moiety -POL of formula (A-1), the moiety -POL may be of formula (A-1iii), (A-1iv), (A-1v) or (A-1vi)

(A1iii)

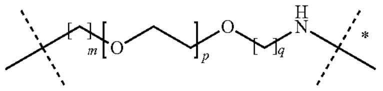

(A1iv)

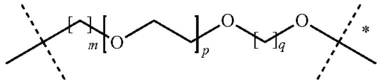

(A1v)

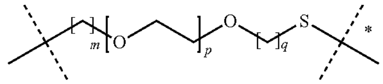

(A1-vi)

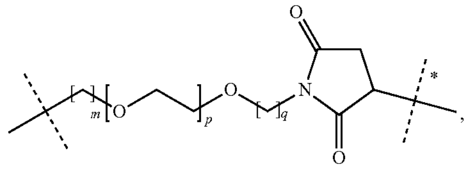

wherein the dashed line marked with the asterisk indicates attachment to the further moiety, such as to a moiety $-L^1-L^2-Z$;

the unmarked dashed line indicates attachment to -SP-; and m, p and q are used as defined in formula (A-1i).

In certain embodiments a further moiety, such as a moiety $-L^1-L^2-Z$, is conjugated to $M_{mod}$ via a moiety -POL of formula (A-1), resulting in a moiety of -POL of formula (A-1iii). In certain embodiments a further moiety, such as a moiety $-L^1-L^2-Z$, is conjugated to $M_{mod}$ via a moiety -POL of formula (A-1), resulting in a moiety of -POL of formula (A-1iv). In certain embodiments a further moiety, such as a moiety $-L^1-L^2-Z$, is conjugated to Ma via a moiety -POL of formula (A-1), resulting in a moiety of -POL of formula (A-1v). In certain embodiments a further moiety, such as a moiety $-L^1$-L2-Z, is conjugated to $M_{mod}$ via a moiety -POL of formula (A-1), resulting in a moiety of -POL of formula (A-1vi).

In certain embodiments -POL of formula (A-1) is a hyaluronic acid-based polymer.

In certain embodiments $M_{mod}$ is of formula (A-1a)

(A-1a)

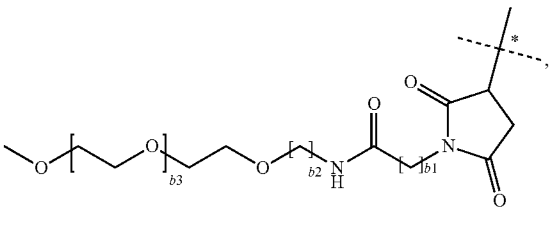

wherein the dashed line marked with the asterisk indicates attachment to the sulfur of a side chain of an amino acid residue of the IL-2 moiety;

b1 is an integer selected from the group consisting of 1, 2, 3, 4, 5, 6, 7, 8, 9, 10, 11, 12, 13, 14, 15, 16, 17, 18, 19 and 20;

b2 is an integer selected from the group consisting of 1, 2, 3, 4, 5, 6, 7, 8, 9, 10, 11, 12, 13, 14, 15, 16, 17, 18, 19 and 20; and b3 is an integer ranging from 12 to 22700.

In certain embodiments b1 of formula (A-1a) is an integer ranging from 1 to 8. In certain embodiments b1 of formula (A-1a) is an integer ranging from 1 to 6. In certain embodiments b1 of formula (A-1a) is an integer ranging from 1 to 4. In certain embodiments b1 of formula (A-1a) is 1. In certain embodiments b1 of formula (A-1a) is 2. In certain embodiments b1 of formula (A-1a) is 3. In certain embodiments b1 of formula (A-1a) is 4. In certain embodiments b1 of formula (A-1a) is 5. In certain embodiments b1 of formula (A-1a) is 6.

In certain embodiments b2 of formula (A-1a) is an integer ranging from 1 to 8. In certain embodiments b2 of formula (A-1a) is an integer ranging from 1 to 6. In certain embodiments b2 of formula (A-1a) is an integer ranging from 1 to 4. In certain embodiments b2 of formula (A-1a) is 1. In certain embodiments b2 of formula (A-1a) is 2. In certain embodiments b2 of formula (A-1a) is 3. In certain embodiments b2 of formula (A-1a) is 4. In certain embodiments b2 of formula (A-1a) is 5. In certain embodiments b2 of formula (A-1a) is 6.

In certain embodiments b3 of formula (A-1a) is an integer ranging from 23 to 227000, such as from 45 to 11300, or from 69 to 4540, or from 114 to 2700. In certain embodiments b3 of formula (A-1a) is about 12. In certain embodiments b3 of formula (A-1a) is about 23. In certain embodiments b3 of formula (A-1a) is about 46. In certain embodiments b3 of formula (A-1a) is about 68. In certain embodiments b3 of formula (A-1a) is about 90. In certain embodiments b3 of formula (A-1a) is about 112. In certain embodiments b3 of formula (A-1a) is about 170. In certain embodiments b3 of formula (A-1a) is about 227. In certain embodiments b3 of formula (A-1a) is about 340. In certain embodiments b3 of formula (A-1a) is about 450. In certain embodiments b3 of formula (A-1a) is about 680. In certain embodiments b3 of formula (A-1a) is about 900. In certain embodiments b3 of formula (A-1a) is about 1130. In certain embodiments b3 of formula (A-1a) is about 1350. In certain embodiments b3 of formula (A-1a) is about 1590. In certain embodiments b3 of formula (A-1a) is about 1800. In certain embodiments b3 of formula (A-1a) is about 2045. In certain embodiments b3 of formula (A-1a) is about 2275.

In certain embodiments b1 of formula (A-1a) is 2, b2 of formula (A-1a) is 3 and b3 of formula (A-1a) is about 12. In certain embodiments b1 of formula (A-1a) is 2, b2 of formula (A-1a) is 3 and b3 of formula (A-1a) is about 23. In certain embodiments b1 of formula (A-1a) is 2, b2 of formula (A-1a) is 3 and b3 of formula (A-1a) is about 46. In certain embodiments b1 of formula (A-1a) is 2, b2 of formula (A-1a) is 3 and b3 of formula (A-1a) is about 68. In certain embodiments b1 of formula (A-1a) is 2, b2 of formula (A-1a) is 3 and b3 of formula (A-1a) is about 90. In certain embodiments b1 of formula (A-1a) is 2, b2 of formula (A-1a) is 3 and b3 of formula (A-1a) is about 112. In certain embodiments b1 of formula (A-1a) is 2, b2 of formula (A-1a) is 3 and b3 of formula (A-1a) is about 170. In certain embodiments b1 of formula (A-1a) is 2, b2 of formula (A-1a) is 3 and b3 of formula (A-1a) is about 227. In certain embodiments b1 of formula (A-1a) is 2, b2 of formula (A-1a) is 3 and b3 of formula (A-1a) is about 340. In certain embodiments b1 of formula (A-1a) is 2, b2 of formula (A-1a) is 3 and b3 of formula (A-1a) is about 450.

In certain embodiments $M_{mod}$ is of formula (A-1b)

(A-1b)

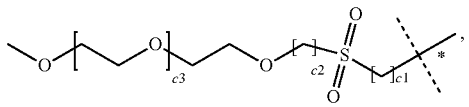

wherein the dashed line marked with the asterisk indicates attachment to the sulfur of a side chain of an amino acid residue of the IL-2 moiety;

c1 is an integer selected from the group consisting of 1, 2, 3, 4, 5, 6, 7, 8, 9, 10, 11, 12, 13, 14, 15, 16, 17, 18, 19 and 20;

c2 is an integer selected from the group consisting of 1, 2, 3, 4, 5, 6, 7, 8, 9, 10, 11, 12, 13, 14, 15, 16, 17, 18, 19 and 20; and c3 is an integer ranging from 12 to 22700.

In certain embodiments c1 of formula (A-1b) is an integer ranging from 1 to 8. In certain embodiments c1 of formula (A-1b) is an integer ranging from 1 to 6. In certain embodiments c1 of formula (A-1b) is an integer ranging from 1 to 4. In certain embodiments c1 of formula (A-1b) is 1. In certain embodiments c1 of formula (A-1b) is 2. In certain embodiments c1 of formula (A-1b) is 3. In certain embodiments c1 of formula (A-1b) is 4. In certain embodiments c1 of formula (A-1b) is 5. In certain embodiments c1 of formula (A-1b) is 6.

In certain embodiments c2 of formula (A-1b) is an integer ranging from 1 to 8. In certain embodiments c2 of formula (A-1b) is an integer ranging from 1 to 6. In certain embodiments c2 of formula (A-1b) is an integer ranging from 1 to 4. In certain embodiments c2 of formula (A-1b) is 1. In certain embodiments c2 of formula (A-1b) is 2. In certain embodiments c2 of formula (A-1b) is 3. In certain embodiments c2 of formula (A-1b) is 4. In certain embodiments c2 of formula (A-1b) is 5. In certain embodiments c2 of formula (A-1b) is 6.

In certain embodiments c3 of formula (A-1b) is an integer ranging from 23 to 227000, such as from 45 to 11300, or from 69 to 4540, or from 114 to 2700. In certain embodiments c3 of formula (A-1b) is about 12. In certain embodiments c3 of formula (A-1b) is about 23. In certain embodiments c3 of formula (A-1b) is about 46. In certain embodiments c3 of formula (A-1b) is about 68. In certain embodiments c3 of formula (A-1b) is about 90. In certain embodiments c3 of formula (A-1b) is about 112. In certain embodiments c3 of formula (A-1b) is about 170. In certain embodiments c3 of formula (A-1b) is about 227. In certain embodiments c3 of formula (A-1b) is about 340. In certain embodiments c3 of formula (A-1b) is about 450. In certain embodiments c3 of formula (A-1b) is about 680. In certain embodiments c3 of formula (A-1b) is about 900. In certain embodiments c3 of formula (A-1b) is about 1130. In certain embodiments c3 of formula (A-1b) is about 1350. In certain embodiments c3 of formula (A-1b) is about 1590. In certain embodiments c3 of formula (A-1b) is about 1800. In certain embodiments c3 of formula (A-1b) is about 2045. In certain embodiments c3 of formula (A-1b) is about 2275.

In certain embodiments c1 of formula (A-1b) is 2, c2 of formula (A-1b) is 3 and c3 of formula (A-1b) is about 12. In certain embodiments c1 of formula (A-1b) is 2, c2 of formula (A-1b) is 3 and c3 of formula (A-1b) is about 23. In certain embodiments c1 of formula (A-1b) is 2, c2 of formula (A-1b) is 3 and c3 of formula (A-1b) is about 46. In certain embodiments c1 of formula (A-1b) is 2, c2 of formula (A-1b) is 3 and c3 of formula (A-1b) is about 68. In certain embodiments c1 of formula (A-1b) is 2, c2 of formula (A-1b) is 3 and c3 of formula (A-1b) is about 90. In certain embodiments c1 of formula (A-1b) is 2, c2 of formula (A-1b) is 3 and c3 of formula (A-1b) is about 112. In certain embodiments c1 of formula (A-1b) is 2, c2 of formula (A-1b) is 3 and c3 of formula (A-1b) is about 170. In certain embodiments c1 of formula (A-1b) is 2, c2 of formula (A-1b) is 3 and c3 of formula (A-1b) is about 227. In certain embodiments c1 of formula (A-1b) is 2, c2 of formula (A-1b) is 3 and c3 of formula (A-1b) is about 340. In certain embodiments c1 of formula (A-1b) is 2, c2 of formula (A-1b) is 3 and c3 of formula (A-1b) is about 450.

In certain embodiments $M_{mod}$ is of formula (A-1c)

(A-1c)

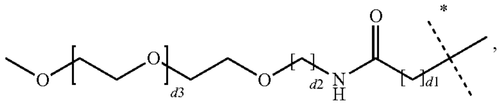

, wherein the dashed line marked with the asterisk indicates attachment to the sulfur of a side chain of an amino acid residue of the IL-2 moiety;

d1 is an integer selected from the group consisting of 1, 2, 3, 4, 5, 6, 7, 8, 9, 10, 11, 12, 13, 14, 15, 16, 17, 18, 19 and 20;

d2 is an integer selected from the group consisting of 1, 2, 3, 4, 5, 6, 7, 8, 9, 10, 11, 12, 13, 14, 15, 16, 17, 18, 19 and 20; and d3 is an integer ranging from 12 to 22700.

In certain embodiments d1 of formula (A-1c) is an integer ranging from 1 to 8. In certain embodiments d1 of formula (A-1c) is an integer ranging from 1 to 6. In certain embodiments d1 of formula (A-1c) is an integer ranging from 1 to 4. In certain embodiments d1 of formula (A-1c) is 1. In certain embodiments d1 of formula (A-1c) is 2. In certain embodiments d1 of formula (A-1c) is 3. In certain embodiments d1 of formula (A-1c) is 4. In certain embodiments d1 of formula (A-1c) is 5. In certain embodiments d1 of formula (A-1c) is 6.

In certain embodiments d2 of formula (A-1c) is an integer ranging from 1 to 8. In certain embodiments d2 of formula (A-1c) is an integer ranging from 1 to 6. In certain embodiments d2 of formula (A-1c) is an integer ranging from 1 to 4. In certain embodiments d2 of formula (A-1c) is 1. In certain embodiments d2 of formula (A-1c) is 2. In certain embodiments d2 of formula (A-1c) is 3. In certain embodiments d2 of formula (A-1c) is 4. In certain embodiments d2 of formula (A-1c) is 5. In certain embodiments d2 of formula (A-1c) is 6.

In certain embodiments d3 of formula (A-1c) is an integer ranging from 23 to 227000, such as from 45 to 11300, or from 69 to 4540, from 114 to 2700 or from 160 to 900. In certain embodiments d3 of formula (A-1c) is about 12. In certain embodiments d3 of formula (A-1c) is about 23. In certain embodiments d3 of formula (A-1c) is about 46. In certain embodiments d3 of formula (A-1c) is about 68. In certain embodiments d3 of formula (A-1c) is about 90. In certain embodiments d3 of formula (A-1c) is about 112. In certain embodiments d3 of formula (A-1c) is about 170. In certain embodiments d3 of formula (A-1c) is about 227. In certain embodiments d3 of formula (A-1c) is about 340. In certain embodiments d3 of formula (A-1c) is about 450. In certain embodiments d3 of formula (A-1c) is about 680. In certain embodiments d3 of formula (A-1c) is about 900. In certain embodiments d3 of formula (A-1c) is about 1130. In certain embodiments d3 of formula (A-1c) is about 1350. In certain embodiments d3 of formula (A-1c) is about 1590. In certain embodiments d3 of formula (A-1c) is about 1800. In certain embodiments d3 of formula (A-1c) is about 2045. In certain embodiments d3 of formula (A-1c) is about 2275.

In certain embodiments d1 of formula (A-1c) is 2, d2 of formula (A-1c) is 3 and d3 of formula (A-1cd) is about 12. In certain embodiments d1 of formula (A-1c) is 2, d2 of formula (A-1c) is 3 and d3 of formula (A-1c) is about 23. In certain embodiments d of formula (A-1c) is 2, d2 of formula (A-1c) is 3 and d3 of formula (A-1c) is about 46. In certain embodiments d1 of formula (A-1c) is 2, d2 of formula (A-1c) is 3 and d3 of formula (A-1c) is about 68. In certain embodiments d1 of formula (A-1c) is 2, d2 of formula (A-1c) is 3 and d3 of formula (A-1c) is about 90. In certain embodiments d1 of formula (A-1c) is 2, d2 of formula (A-1c) is 3 and d3 of formula (A-1c) is about 112. In certain embodiments d1 of formula (A-1c) is 2, d2 of formula (A-1c) is 3 and d3 of formula (A-1c) is about 170. In certain embodiments d of formula (A-1c) is 2, d2 of formula (A-1c) is 3 and d3 of formula (A-1c) is about 227. In certain embodiments d1 of formula (A-1c) is 2, d2 of formula (A-1c) is 3 and d3 of formula (A-1c) is about 340. In certain embodiments d1 of formula (A-1c) is 2, d2 of formula (A-1c) is 3 and d3 of formula (A-1c) is about 450.

The biased IL-2 moiety may comprise an IL-2 moiety comprising at least one amino acid mutation, such as one amino acid mutation, two amino acid mutations, three amino acid mutations, four amino acid mutations, five amino acid mutations, six amino acid mutations, seven amino acid mutations, eight amino acid mutations, nine amino acid mutations or ten amino acid mutations. Such amino acid mutation preferably occurs at a position that is involved in binding to IL-2Rα. Thus, preferably, the at least amino acid mutation results in a reduced affinity of the biased IL-2 moiety to IL-2Rαβ compared to aldesleukin.

Preferably the at least one amino acid mutation occurs at an amino acid position selected from the group consisting of K34, $R^{37}$, M38, T40, F41, K42, F43, Y44, E61, and L71, based on SEQ ID NO:2 or at the corresponding positions of homologs or variants thereof. Even more preferably the at least one amino acid mutation occurs at an amino acid position selected from the group consisting of F41, Y44, E61 and L71 based on SEQ ID NO:2 or at the corresponding positions of homologs or variants thereof. In certain embodiments the at least one amino acid mutation occurs at amino acid position K34 based on SEQ ID NO:2 or at the corresponding positions of homologs or variants thereof. In certain embodiments the at least one amino acid mutation occurs at amino acid position R37 based on SEQ ID NO:2 or at the corresponding positions of homologs or variants thereof. In certain embodiments the at least one amino acid mutation occurs at amino acid position M38 based on SEQ ID NO:2 or at the corresponding positions of homologs or variants thereof. In certain embodiments the at least one amino acid mutation occurs at amino acid position T40 based on SEQ ID NO:2 or at the corresponding positions of homologs or variants thereof. In certain embodiments the at least one amino acid mutation occurs at amino acid position F41 based on SEQ ID NO:2 or at the corresponding positions of homologs or variants thereof. In certain embodiments the at least one amino acid mutation occurs at amino acid position 142 based on SEQ ID NO:2 or at the corresponding positions of homologs or variants thereof. In certain embodiments the at least one amino acid mutation occurs at amino acid position F43 based on SEQ ID NO:2 or at the corresponding positions of homologs or variants thereof. In certain embodiments the at least one amino acid mutation occurs at amino acid position Y44 based on SEQ ID NO:2 or at the corresponding positions of homologs or variants thereof. In certain embodiments the at least one amino acid mutation occurs at amino acid position E61 based on SEQ ID NO:2 or at the corresponding positions of homologs or variants thereof. In certain embodiments the at least one amino acid mutation occurs at amino acid position L71 based on SEQ ID NO:2 or at the corresponding positions of homologs or variants thereof.

In certain embodiments such mutations are a replacement of a naturally occurring amino acid with an amino acid residue selected from the group consisting of alanine, arginine, asparagine, aspartic acid, cysteine, glutamine, glutamic acid, glycine, histidine, lysine, serine, threonine, tryptophan and tyrosine. In certain embodiments the naturally occurring amino acid is replaced with alanine. In certain embodiments the naturally occurring amino acid is replaced with arginine. In certain embodiments the naturally occurring amino acid is replaced with asparagine. In certain embodiments the naturally occurring amino acid is replaced with aspartic acid. In certain embodiments the naturally occurring amino acid is replaced with cysteine. In certain embodiments the naturally occurring amino acid is replaced with glutamine. In certain embodiments the naturally occurring amino acid is replaced with glutamic acid. In certain embodiments the naturally occurring amino acid is replaced with glycine. In certain embodiments the naturally occurring amino acid is replaced with histidine. In certain embodiments the naturally occurring amino acid is replaced with lysine. In certain embodiments the naturally occurring amino acid is replaced with serine. In certain embodiments the naturally occurring amino acid is replaced with threonine. In certain embodiments the naturally occurring amino acid is replaced with tryptophan. In certain embodiments the naturally occurring amino acid is replaced with tyrosine. In certain embodiments such mutations are a replacement of a naturally occurring amino acid with an amino acid residue selected from the group consisting of arginine, aspartic acid, cysteine, glutamine, glutamic acid, histidine, lysine, serine, threonine, tryptophan and tyrosine. In certain embodiments such mutations are a replacement of a naturally occurring amino acid with an amino acid residue selected from the group consisting of cysteine, glutamic acid, lysine, serine, threonine and tyrosine. In certain embodiments the naturally occurring amino acid is replaced by a non-proteinogenic amino acid. Embodiments for such non-proteinogenic amino acids are as described above.

In one embodiment the IL-2 of the biased IL-2 moiety comprises an amino acid mutation selected from the group consisting of K34A, K34C, K34G, K34S, K34T, K34Q, K34E, K34N, K34D, K34H, K34W, K34Y and K34R, based on SEQ ID NO:2 or the corresponding positions of homologs or variants thereof. In certain embodiments the IL-2 moiety comprises the K34A mutation. In certain embodiments the IL-2 moiety comprises the K34C mutation. In certain embodiments the IL-2 moiety comprises the K34G mutation. In certain embodiments the IL-2 moiety comprises the K34S mutation. In certain embodiments the IL-2 moiety comprises the K34T mutation. In certain embodiments the IL-2 moiety comprises the K34Q mutation. In certain embodiments the IL-2 moiety comprises the K34E mutation. In certain embodiments the IL-2 moiety comprises the K34D mutation. In certain embodiments the IL-2 moiety comprises the K34H mutation. In certain embodiments the IL-2 moiety comprises the K34W mutation. In certain embodiments the IL-2 moiety comprises the K34Y mutation. In certain embodiments the IL-2 moiety comprises the K34R mutation.

In one embodiment the IL-2 moiety of the biased IL-2 comprises an amino acid mutation selected from the group consisting of R37A, R37C, R37G, R37S, R37T, R37Q, R37E, R37N, R37D, R37H, R37W, R37Y and R37K, based on SEQ ID NO:2 or the corresponding positions of homologs or variants thereof. In certain embodiments the IL-2 moiety comprises the R37A mutation. In certain embodiments the IL-2 moiety comprises the R37C mutation. In certain embodiments the IL-2 moiety comprises the R37G mutation. In certain embodiments the IL-2 moiety comprises the R37S mutation. In certain embodiments the IL-2 moiety comprises the R37T mutation. In certain embodiments the IL-2 moiety comprises the R37Q mutation. In certain embodiments the IL-2 moiety comprises the R37E mutation. In certain embodiments the IL-2 moiety comprises the R37N mutation. In certain embodiments the IL-2 moiety comprises the R37D mutation. In certain embodiments the IL-2 moiety comprises the R37H mutation. In certain embodiments the IL-2 moiety comprises the R37K mutation. In certain embodiments the IL-2 moiety comprises the R37W mutation. In certain embodiments the IL-2 moiety comprises the R37Y mutation. In certain embodiments the IL-2 moiety comprises the R37K mutation.

In one embodiment the at least one amino acid mutation is selected from the group consisting of F41A, F41C, F41G, F41S, F41T, F41Q, F41E, F41N, F41D, F41R, F41K, Y44A, Y44C, Y44G, Y44S, Y44T, Y44Q, Y44E, Y44N, Y44D, Y44R, Y44K, L71C, L71G, L71A, L71S, L71T, L71Q, L71E, L71N, L71D, L71R, and L71K, based on SEQ ID NO: 2 or the corresponding positions of homologs or variants thereof.

In certain embodiments the IL-2 moiety of the biased IL-2 comprises an amino acid mutation selected from the group consisting of F41A, F41C, F41G, F41S, F41T, F41Q, F41E, F41N, F41D, F41R, F41H, F41W, F41Y and F41K, based on SEQ ID NO:2 or the corresponding positions of homologs or variants thereof. In certain embodiments the IL-2 moiety comprises an amino acid mutation selected from the group consisting of F41A, F41C, F41G, F41S, F41T, F41Q, F41E, F41N, F41D, F41R and F41K, based on SEQ ID NO:2 or the corresponding positions of homologs or variants thereof. In one embodiment the IL-2 moiety comprises the F41A mutation. In another embodiment the IL-2 moiety comprises the F41C mutation. In another embodiment the IL-2 moiety comprises the F41G mutation. In another embodiment the IL-2 moiety comprises the F41S mutation. In another embodiment the IL-2 moiety comprises the F41T mutation. In another embodiment the IL-2 moiety comprises the F41Q mutation. In another embodiment the IL-2 moiety comprises the F41E mutation. In another embodiment the IL-2 moiety comprises the F41N mutation. In another embodiment the IL-2 moiety comprises the F41D mutation. In another embodiment the IL-2 moiety comprises the F41R mutation. In another embodiment the IL-2 moiety comprises the F41H mutation. In another embodiment the IL-2 moiety comprises the F41W mutation. In another embodiment the IL-2 moiety comprises the F41Y mutation. In another embodiment the IL-2 moiety comprises the F41K mutation.

In certain embodiments the IL-2 moiety comprises an amino acid mutation selected from the group consisting of Y44A, Y44C, Y44G, Y44S, Y44T, Y44Q, Y44E, Y44N, Y44D, Y44R, Y44H, Y44W and Y44K, based on SEQ ID NO:2 or the corresponding positions of homologs or variants thereof. In certain embodiments the IL-2 moiety comprises an amino acid mutation selected from the group consisting of Y44A, Y44C, Y44G, Y44S, Y44T, Y44Q, Y44E, Y44N, Y44D, Y44R and Y44K, based on SEQ ID NO:2 or the corresponding positions of homologs or variants thereof. In one embodiment the IL-2 moiety comprises the Y44A mutation. In another embodiment the IL-2 moiety comprises the Y44C mutation. In another embodiment the IL-2 moiety comprises the Y44G mutation. In another embodiment the IL-2 moiety comprises the Y44S mutation. In another embodiment the IL-2 moiety comprises the Y44T mutation. In another embodiment the IL-2 moiety comprises the Y44Q mutation. In another embodiment the IL-2 moiety comprises the Y44E mutation. In another embodiment the IL-2 moiety comprises the Y44N mutation. In another embodiment the IL-2 moiety comprises the Y44D mutation. In another embodiment the IL-2 moiety comprises the Y44R mutation. In another embodiment the IL-2 moiety comprises the Y44H mutation. In another embodiment the IL-2 moiety comprises the Y44W mutation. In another embodiment the IL-2 moiety comprises the Y44K mutation.

In certain embodiments the IL-2 moiety comprises an amino acid mutation selected from the group consisting of L71G, L71C, L71A, L71S, L71T, L71Q, L71E, L71N, L71D, L71R, L71H, L71W, L71Y and L71K, based on SEQ ID NO:2 or the corresponding positions of homologs or variants thereof. In certain embodiments the IL-2 moiety comprises an amino acid mutation selected from the group consisting of L71G, L71C, L71A, L71S, L71T, L71Q, L71E, L71N, L71D, L71R and L71K, based on SEQ ID NO:2 or the corresponding positions of homologs or variants thereof. In one embodiment the IL-2 moiety comprises the L72G mutation. In another embodiment the IL-2 moiety comprises the L72C mutation. In another embodiment the IL-2 moiety comprises the L72A mutation. In another embodiment the IL-2 moiety comprises the L72S mutation. In another embodiment the IL-2 moiety comprises the L72T mutation. In another embodiment the IL-2 moiety comprises the L72Q mutation. In another embodiment the IL-2 moiety comprises the L72E mutation. In another embodiment the IL-2 moiety comprises the L72N mutation. In another embodiment the IL-2 moiety comprises the L72D mutation. In another embodiment the IL-2 moiety comprises the L72R mutation. In another embodiment the IL-2 moiety comprises the L72H mutation. In another embodiment the IL-2 moiety comprises the L72W mutation. In another embodiment the IL-2 moiety comprises the L72Y mutation. In another embodiment the IL-2 moiety comprises the L72K mutation.

In another embodiment the IL-2 moiety comprises an amino acid mutation selected from the group consisting of F41A, F41C, F41G, F41S, F41T, F41Q, F41E, F41N, F41D, F41R and F41K and a further amino acid mutation selected from the group consisting of Y44A, Y44C, Y44G, Y44S, Y44T, Y44Q, Y44E, Y44N, Y44D, Y44R and Y44K, based on SEQ ID NO:2 or the corresponding positions of homologs or variants thereof. In one embodiment the IL-2 moiety comprises the F41A and Y44A mutations. In another embodiment the IL-2 moiety comprises the F41C mutation and the Y44A mutations. In another embodiment the IL-2 moiety comprises the F41A and the Y44C mutations.

In another embodiment the IL-2 moiety comprises an amino acid mutation selected from the group consisting of F41A, F41C, F41G, F41S, F41T, F41Q, F41E, F41N, F41D, F41R and F41K and a further amino acid mutation selected from the group consisting of L71G, L71C, L71A, L71S, L71T, L71Q, L71E, L71N, L71D, L71R and L71K, based on SEQ ID NO:2 or the corresponding positions of homologs or variants thereof. In one embodiment the IL-2 moiety comprises the F42A and L72G mutations. In another embodiment the IL-2 moiety comprises the F42C and L72G mutation. In another embodiment the IL-2 moiety comprises the F42A and L72C mutation.

In another embodiment the IL-2 moiety comprises an amino acid mutation selected from the group consisting of Y44A, Y44C, Y44G, Y44S, Y44T, Y44Q, Y44E, Y44N, Y44D, Y44R and Y44K and a further amino acid mutation selected from the group consisting of L71G, L71C, L71A, L71S, L71T, L71Q, L71E, L71N, L71D, L71R and L71K, based on SEQ ID NO:2 or the corresponding positions of homologs or variants thereof. In one embodiment the IL-2 moiety comprises the Y45A and L72G mutations. In another embodiment the IL-2 moiety comprises the Y45C and L72G mutations. In another embodiment the IL-2 moiety comprises the Y45A and L72C mutations.

In another embodiment the IL-2 moiety comprises an amino acid mutation selected from the group consisting of F41A, F41C, F41G, F41S, F41T, F41Q, F41E, F41N, F41D, F41R and F41K; a further amino acid mutation selected from the group consisting of Y44A, Y41C, Y44G, Y44S, Y44T, Y44Q, Y44E, Y44N, Y44D, Y44R and Y44K and a further amino acid mutation selected from the group consisting of L71G, L71C, L71A, L71S, L71T, L71Q, L71E, L71N, L71D, L71R and L71K, based on SEQ ID NO:2 or the corresponding positions of homologs or variants thereof. In one embodiment the IL-2 moiety comprises the F41A, Y44A and L71G mutations. In another embodiment the IL-2 moiety comprises the F41C, Y44A and L71G mutations. In another embodiment the IL-2 moiety comprises the F41A, Y44C and the L71G mutations. In another embodiment the IL-2 moiety comprises the F41A, Y44C and L71C mutations.

The IL-2 moiety may in addition or alternatively comprise an amino acid mutation, which eliminates the O-glycosylation site. Preferably, such amino acid mutation is at a position corresponding to residue 2 of aldesleukin, even more preferably such amino acid mutation is selected from the group consisting of T2A, T2G, T2Q, T2E, T2N, T2D, T2R, T2K and T2P and most preferably is T2A, based on SEQ ID NO:2 or the corresponding positions of homologs or variants thereof.

The IL-2 moiety may in addition or alternatively comprise one or more further amino acid mutations that may provide additional advantages, such as increased expression or stability. For example, the methionine at position 103 of aldesleukin may be replaced by a neutral amino acid such as alanine, as described in U.S. Pat. No. 5,206,344.

In certain embodiments the biased IL-2 moiety is an IL-2 moiety comprising at least one amino acid mutation and at least one stable attachment of a modifying moiety $M_{mod}$, such as one amino acid mutation and one moiety $M_{mod}$, one amino acid mutation and two moieties $M_{mod}$, two amino acid mutations and one moiety $M_{mod}$, three amino acid mutations and one moiety $M_{mod}$, or one amino acid mutation and three moieties $M_{mod}$. It is understood that the number of amino acid mutations and moieties $M_{mod}$ may be chosen independently of each other and may be selected from the group consisting of 1, 2, 3, 4, 5, 6, 7, 8, 9, 10, 11, 12, 13, 14 and 15. In certain embodiments the number of amino acid mutations and moieties $M_{mod}$ is independently of each other selected from the group consisting of 1, 2, 3, 4, 5, 6, 7 and 8. In certain embodiments the number of amino acid mutations is 1. In certain embodiments the number of amino acid mutations is 2. In certain embodiments the number of amino acid mutations is 3. In certain embodiments the number of amino acid mutations is 4. In certain embodiments the number of amino acid mutations is 5. In certain embodiments the number of amino acid mutations is 6. In certain embodiments the number of moieties $M_{mod}$ is 1. In certain embodiments the number of moieties $M_{mod}$ is 2. In certain embodiments the number of moieties $M_{mod}$ is 3. In certain embodiments the number of moieties $M_{mod}$ is 4. In certain embodiments the number of moieties $M_{mod}$ is 5. In certain embodiments the number of moieties $M_{mod}$ is 6. Embodiments for moieties $M_{mod}$ and mutation sites/mutations are as described above.

In certain embodiments the biased IL-2 moiety is an IL-2 moiety comprising at least one amino acid mutation and at least one moiety $M_{mod}$ attached to such mutated amino acid. It is understood that the number of amino acid mutations and moieties $M_{mod}$ may not be identical and that further moieties $M_{mod}$ may be conjugated to the IL-2 moiety at non-mutated amino acid residues and that not all mutated amino acid residues may be conjugated to a moiety $M_{mod}$, as long as at least one moiety $M_{mod}$ is conjugated to one mutated amino acid residue. Thus, the number of amino acid mutations and moieties $M_{mod}$ may be chosen independently of each other and may be selected from the group consisting of 1, 2, 3, 4, 5, 6, 7, 8, 9, 10, 11, 12, 13, 14 and 15. In certain embodiments the number of amino acid mutations and moieties $M_{mod}$ is independently of each other selected from the group consisting of 1, 2, 3, 4, 5, 6, 7 and 8. In certain embodiments the number of amino acid mutations is 1. In certain embodiments the number of amino acid mutations is 2. In certain embodiments the number of amino acid mutations is 3. In certain embodiments the number of amino acid mutations is 4. In certain embodiments the number of amino acid mutations is 5. In certain embodiments the number of amino acid mutations is 6. In certain embodiments the number of moieties $M_{mod}$ is 1. In certain embodiments the number of moieties $M_{mod}$ is 2. In certain embodiments the number of moieties $M_{mod}$ is 3. In certain embodiments the number of moieties $M_{mod}$ is 4. In certain embodiments the number of moieties $M_{mod}$ is 5. In certain embodiments the number of moieties $M_{mod}$ is 6. Embodiments for moieties $M_{mod}$ and mutation sites/mutations are as described above.

In certain embodiments the biased IL-2 moiety is an IL-2 moiety comprising at least one amino acid mutation at a position selected from the group consisting of K34, R37, M38, T40, F41, K42, F43, Y44, E61, and L71, wherein the naturally occurring amino acid is replaced by a cysteine resulting in mutations K34C, R37C, M38C, T40C, F41C, K42C, F43C, Y44C, E61C, and L71C, and wherein at least one moiety $M_{mod}$ is conjugated to the sulfur of such cysteine. In certain embodiments the biased IL-2 moiety comprises the K34C mutation and in addition a moiety $M_{mod}$ conjugated to the sulfur of the cysteine that replaced the lysine at position 34. In certain embodiments the biased IL-2 moiety comprises the R37C mutation and in addition a moiety $M_{mod}$ conjugated to the sulfur of the cysteine that replaced the arginine at position 37. In certain embodiments the biased IL-2 moiety comprises the M38C mutation and in addition a moiety $M_{mod}$ conjugated to the sulfur of the cysteine that replaced the methionine at position 38. In certain embodiments the biased IL-2 moiety comprises the T40C mutation and in addition a moiety $M_{mod}$ conjugated to the sulfur of the cysteine that replaced the threonine at position 40. In certain embodiments the biased IL-2 moiety comprises the F41C mutation and in addition a moiety $M_{mod}$ conjugated to the sulfur of the cysteine that replaced the phenylalanine at position 41. In certain embodiments the biased IL-2 moiety comprises the K42C mutation and in addition a moiety $M_{mod}$ conjugated to the sulfur of the cysteine that replaced the lysine at position 42. In certain embodiments the biased IL-2 moiety comprises the F43C mutation and in addition a moiety $M_{mod}$ conjugated to the sulfur of the cysteine that replaced the phenylalanine at position 43. In certain embodiments the biased IL-2 moiety comprises the Y44C mutation and in addition a moiety $M_{mod}$ conjugated to the sulfur of the cysteine that replaced the tyrosine at position 44. In certain embodiments the biased IL-2 moiety comprises the E61C mutation and in addition a moiety $M_{mod}$ conjugated to the sulfur of the cysteine that replaced the glutamic acid at position 61. In certain embodiments the biased IL-2 moiety comprises the L71C mutation and in addition a moiety $M_{mod}$ conjugated to the sulfur of the cysteine that replaced the lysine at position 71. In certain embodiments the biased IL-2 moiety comprises one mutation selected from the group consisting of K34C, R37C, M38C, T40C, F41C, K42C, F43C, Y44C, E61C, and L71C, wherein one moiety $M_{mod}$ is conjugated to the sulfur of the cysteine that replaced the naturally occurring amino acid, i.e. the arginine at position 37 in case of the R37C mutation, for example.

The IL-2 moiety may comprise at least one deletion (see point (c)). It is understood that such a deletion is preferably in reference to the sequence of SEQ ID NO:2. Such a deletion may be a naturally occurring deletion, such as for example in the form of a splice variant or may be a deletion artificially introduced. One such naturally occurring splice variant is the IL-2δ2 mutant (see Tsytsikov et al., JBC 1996, 271(38): 23055-23060), in which exon 2 is excluded and which results in the deletion of amino acid residues N30 to K49, based on the sequence of SEQ ID NO:1, which corresponds to a deletion of amino acid residues N29 to K48 based on the sequence of SEQ ID NO:2.

Preferably such a deletion occurs at a position that is involved in binding to IL-2Rα. Thus, preferably, the at least one deletion results in a reduced affinity of the biased IL-2 moiety to IL-2Rαβ compared to aldesleukin.

In one embodiment -D comprises an IL-2 moiety, preferably an IL-2 moiety having the sequence of SEQ ID NO:2, which comprises at least one mutation that introduces a cysteine residue, and in addition comprises a modifying moiety $M_{mod}$ attached to said cysteine mutation. Preferably, the cysteine mutation is selected from the group comprising of K34C, R37C, M38C, T40C, F41C, K42C, F43C, Y44C, E61C and L71C. In certain embodiments the cysteine mutation is the K34C mutation. In certain embodiments the cysteine mutation is the R37C mutation. In certain embodiments the cysteine mutation is the M38C mutation. In certain embodiments the cysteine mutation is the T40C mutation. In certain embodiments the cysteine mutation is the F41C mutation. In certain embodiments the cysteine mutation is the K42C mutation. In certain embodiments the cysteine mutation is the F43C mutation. In certain embodiments the cysteine mutation is the Y44C mutation. In certain embodiments the cysteine mutation is the E61C mutation. In certain embodiments the cysteine mutation is the L71C mutation.

In one embodiment the IL-2 moiety is a superkine as described in Levin et al. (Nature, 2012, 484: 529-535). Preferably, such IL-2 moiety comprises in addition or alternatively to the modifications described above at one or mutations of amino acid residues Q73, L79, R80, L84, 185 and 191 and in particular comprises one or more of the mutations selected from the group consisting of Q73H, L79F, R80D, L84V, I85V and I91F. In one embodiment the IL-2 moiety comprises in addition or alternatively to the modifications described above the Q73H, L79F, R80D, L84V, I85V and I91F mutations. In another embodiment the IL-2 moiety comprises in addition or alternatively to the modifications described above the L79F, R80D, L84V, I85V and I91F mutations. If the IL-2 moiety is based on a superkine, the corresponding biased IL-2 has a higher affinity to IL-2Rβ than aldesleukin.

The IL-2 conjugate of the present invention comprises at least one covalently and reversibly attached polymeric moiety and/or substituted fatty acid moiety —Z.

It was surprisingly found that the addition of such at least one covalently and reversibly attached polymeric moiety and/or substituted fatty acid moiety is capable of further extending the circulation half-life of the biased IL-2 moiety, while its reversible attachment ensures sufficient affinity to IL-2Rβ after cleavage of the at least one covalently and reversibly attached polymeric moiety or substituted fatty acid moiety.

In one embodiment the IL-2 conjugate of the present invention comprises one moiety —Z, which is either a substituted fatty acid or a polymeric moiety. In one embodiment —Z is a substituted fatty acid. In another embodiment —Z is a polymeric moiety.

In another embodiment the IL-2 conjugate of the present invention comprises two moieties —Z, which may be the same or different. In one embodiment both moieties —Z are a substituted fatty acid, which may be the same or different. In another embodiment both moieties —Z are a polymeric moiety, which may be the same or different. In another embodiment one moiety —Z is a substituted fatty acid and the other moiety —Z is a polymeric moiety.

In another embodiment the IL-2 conjugate of the present invention comprises three moieties —Z, which may be the same or different. In one embodiment all three moieties —Z are a substituted fatty acid, which may be the same or different. In another embodiment all three moieties —Z are a polymeric moiety, which may be the same or different. In another embodiment one or two moieties —Z are a substituted fatty acid and the remaining moiety/moieties —Z is/are a polymeric moiety.

In another embodiment the IL-2 conjugate of the present invention comprises four moieties —Z, which may be the same or different. In one embodiment all four moieties —Z are a substituted fatty acid, which may be the same or different. In another embodiment all four moieties —Z are a polymeric moiety, which may be the same or different. In another embodiment one, two or three moieties —Z are a substituted fatty acid and the remaining moiety/moieties —Z is/are a polymeric moiety.

If —Z is a substituted fatty acid moiety it is preferably a substituted fatty acid moiety disclosed in WO 2005/027978 A2 and WO 2014/060512 A1, which are herewith incorporated by reference.

If —Z is a polymeric moiety, such polymeric moiety has preferably a molecular weight ranging from 1 kDa to 1000 kDa, more preferably from 2 kDa to 500 kDa, even more preferably from 3 kDa to 200 kDa, even more preferably from 5 kDa to 120 kDa, even more preferably from 10 kDa to 100 kDa and most preferably from 15 kDa to 80 kDa. In one embodiment —Z is a polymeric moiety having a molecular weight of about 2 kDa. In another embodiment —Z is a polymeric moiety having a molecular weight of about 5 kDa. In another embodiment —Z is a polymeric moiety having a molecular weight of about 10 kDa. In another embodiment —Z is a polymeric moiety having a molecular weight of about 15 kDa. In another embodiment —Z is a polymeric moiety having a molecular weight of about 20 kDa. In another embodiment —Z is a polymeric moiety having a molecular weight of about 30 kDa. In another embodiment —Z is a polymeric moiety having a molecular weight of about 40 kDa. In another embodiment —Z is a polymeric moiety having a molecular weight of about 50 kDa. In another embodiment —Z is a polymeric moiety having a molecular weight of about 60 kDa. In another embodiment —Z is a polymeric moiety having a molecular weight of about 70 kDa. In another embodiment —Z is a polymeric moiety having a molecular weight of about 80 kDa. In another embodiment —Z is a polymeric moiety having a molecular weight of about 90 kDa. In another embodiment —Z is a polymeric moiety having a molecular weight of about 100 kDa. In one embodiment —Z is a polymeric moiety having a molecular weight of 2 kDa. In another embodiment —Z is a polymeric moiety having a molecular weight of 5 kDa. In another embodiment —Z is a polymeric moiety having a molecular weight of 10 kDa. In another embodiment —Z is a polymeric moiety having a molecular weight of 15 kDa. In another embodiment —Z is a polymeric moiety having a molecular weight of 20 kDa. In another embodiment —Z is a polymeric moiety having a molecular weight of 30 kDa. In another embodiment —Z is a polymeric moiety having a molecular weight of 40 kDa. In another embodiment —Z is a polymeric moiety having a molecular weight of 50 kDa. In another embodiment —Z is a polymeric moiety having a molecular weight of 60 kDa. In another embodiment —Z is a polymeric moiety having a molecular weight of 70 kDa. In another embodiment —Z is a polymeric moiety having a molecular weight of 80 kDa. In another embodiment —Z is a polymeric moiety having a molecular weight of 90 kDa. In another embodiment —Z is a polymeric moiety having a molecular weight of 100 kDa.

If —Z is a polymeric moiety, such polymeric moiety preferably comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, alginate, mannans, pectins, rhamnogalacturonans, starches, hydroxyalkyl starches, hydroxyethyl starches and other carbohydrate-based polymers, xylans, and copolymers thereof.

In one embodiment —Z is a peptide or protein moiety. Preferably, such peptide or protein moiety is not an IL-2-moiety or fragment thereof. Such peptide or protein moiety —Z may be chemically conjugated to -D via $-L^1-L^2-$ or may be translationally fused to -D via a reversible linker moiety $-L^1-$, in which case $-L^1-$ is a peptide or protein moiety and $-L^2-$ is preferably a chemical bond. In one embodiment such peptide or protein moiety —Z is chemically conjugated to -D via $-L^1-L^2-$. In another embodiment such peptide or protein moiety —Z is translationally fused to -D via a reversible linker moiety $-L^1-$, in which case $-L^1-$ is a peptide or protein moiety and $-L^2-$ is preferably a chemical bond. It is understood that such peptide or protein reversible linker moiety $-L^1-$ may be enzymatically or non-enzymatically degradable. To facilitate enzymatic degradation $-L^1-$ may comprise a protease recognition site.

If —Z is a peptide or protein moiety it is preferably selected from the group consisting of moieties comprising the carboxyl-terminal peptide of the chorionic gonadotropin as described in US 2012/0035101 A1, which are herewith incorporated by reference; albumin moieties; random coil protein moieties and Fc fusion protein moieties.

In one embodiment —Z comprises a random coil peptide or protein moiety.

Preferably such random coil peptide or protein moiety comprises at least 25 amino acid residues and at most 2000 amino acids. Even more preferably such random coil peptide or protein moiety comprises at least 30 amino acid residues and at most 1500 amino acid residues. Even more preferably such random coil peptide or protein moiety comprises at least 50 amino acid residues and at most 500 amino acid residues.

In a preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine and proline. Even more preferably, at least 10%, but less than 75%, preferably less than 65%, of the total number of amino acid residues of such random coil protein moiety are proline residues. Preferably, such random coil protein moiety is as described in WO 2011/144756 A1 which is hereby incorporated by reference in its entirety. Even more preferably —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO2011/144756 which are hereby incorporated by reference. A moiety comprising such random coil protein comprising alanine and proline will be referred to as "PA" or "PA moiety".

Accordingly, in one embodiment —Z comprises a PA moiety.

In another embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, serine and proline. Even more preferably, at least 4%, but less than 40% of the total number of amino acid residues of such random coil protein moiety are proline residues. Preferably, such random coil protein moiety is as described in WO 2008/155134 A1, which is hereby incorporated by reference in its entirety. Even more preferably —Z comprises at least one moiety selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1, which are hereby incorporated by reference. A moiety comprising such random coil protein moiety comprising alanine, serine and proline will be referred to as "PAS" or "PAS moiety".

Accordingly, in one embodiment —Z comprises a PAS moiety.

In another embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine, serine, threonine, glutamate and proline. Preferably, such random coil protein moiety is as described in WO 2010/091122 A1, which is hereby incorporated by reference. Even more preferably —Z comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:1715, SEQ ID NO:1716, SEQ ID NO:1718, SEQ ID NO:1719, SEQ ID NO:1720, SEQ ID NO:1721 and SEQ ID NO:1722 as disclosed in WO2010/091122A1, which are hereby incorporated by reference. A moiety comprising such random coil protein moiety comprising alanine, glycine, serine, threonine, glutamate and proline will be referred to as "XTEN" or "XTEN moiety" in line with its designation in WO 2010/091122 A1.

Accordingly, in one embodiment —Z comprises an XTEN moiety.

In another embodiment —Z is a hyaluronic acid-based polymer.

In another embodiment —Z is a PEG-based moiety, such as a linear, branched or multi-arm PEG-based moiety. In one embodiment —Z is a branched PEG-based moiety. Preferably, such branched PEG-based moiety —Z is a branched PEG-based moiety having one, two, three, four, five or six branching points. Preferably, —Z is a branched PEG-based moiety having one, two or three branching points. In one embodiment —Z is a branched PEG-based moiety having one branching point. In another embodiment —Z is a branched PEG-based moiety having two branching points. In another embodiment —Z is a branched PEG-based moiety having three branching points.

Each branching point is preferably independently selected from the group consisting of —N<, —CH< and >C<.

In certain embodiments —Z comprises a moiety of formula (A)

(A)

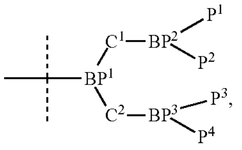

wherein

—$BP^1$<, —$BP^2$<, —$BP^3$< are independently of each other selected from the group consisting of —N< and —$C(R^8)$<;

$R^8$ is selected from the group consisting of H, $C_{1-6}$ alkyl, $C_{2-6}$ alkenyl and $C_{2-6}$ alkynyl;

—$P^1$, —$P^2$, —$P^3$, —$P^4$ are independently of each other a PEG-based chain comprising at least 40% PEG and having a molecular weight ranging from 3 to 40 kDa;

—$C^1$—, —$C^2$— are independently of each other selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $R^9$, which are the same or different and wherein $C_{2-50}$ alkyl, $C_{2-50}$ alkenyl, and $C_{2-50}$ alkynyl are optionally interrupted by one or more groups selected from the group consisting of -T-, —C(O)O—, —O—, —C(O)—, —$C(O)N(R^{10})$—, —$S(O)_2N(R^{10})$—, —$S(O)N(R^{10})$—, —$S(O)_2$—, —S(O)—, —$N(R^{10})S(O)_2N(R^{10a})$—, —S—, —$N(R^{10})$—, —$OC(OR^{10})(R^{10a})$—, —$N(R^{10})C(O)N(R^{10a})$—, and —$OC(O)N(R^{10})$—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^9$, which are the same or different;

each $R^9$ is independently selected from the group consisting of halogen, —CN, oxo (=O), —$COOR^{11}$, —$OR^{11}$, —$C(O)R^{11}$, —$C(O)N(R^{11}R^{11a})$, —$S(O)_2N(R^{11}R^{11a})$, —$S(O)N(R^{11}R^{11a})$, —$S(O)_2R^{11}$, —$S(O)R^{11}$, —$N(R^{11})S(O)_2N(R^{11a}R^{11b})$, —$SR^{11}$, —$N(R^{11}R^{11a})$, —$NO_2$, —$OC(O)R^{11}$, —$N(R^{11})C(O)R^{11a}$, —$N(R^{11})S(O)_2R^{11a}$, —$N(R^{11})S(O)R^{11a}$, —$N(R^{11})C(O)OR^{11a}$, —$N(R^{11})C(O)N(R^{11a}R^{11b})$, —$OC(O)N(R^{11}R^{11a})$, and $C_{1-6}$ alkyl; wherein $C_{1-6}$ alkyl is optionally substituted with one or more halogen, which are the same or different; and each $R^{10}$, $R^{10a}$, $R^{11}$, $R^{11a}$ and $R^{11b}$ is independently selected from the group consisting of —H, and $C_{1-6}$ alkyl, wherein $C_{1-6}$ alkyl is optionally substituted with one or more halogen, which are the same or different.

In certain embodiments —$P^1$, —$P^2$, —$P^3$, $P^4$ are independently of each other a PEG-based chain comprising at least 50% PEG and having a molecular weight ranging from 3 to 40 kDa. In certain embodiments —$P^1$, —$P^2$, —$P^3$, —$P^4$ are independently of each other a PEG-based chain comprising at least 60% PEG and having a molecular weight ranging from 3 to 40 kDa. In certain embodiments —$P^1$, —$P^2$, —$P^3$, —$P^4$ are independently of each other a PEG-based chain comprising at least 70% PEG and having a molecular weight ranging from 3 to 40 kDa. In certain embodiments —$P^1$, —$P^2$, —$P^3$, —$P^4$ are independently of each other a PEG-based chain comprising at least 80% PEG and having a molecular weight ranging from 3 to 40 kDa.

In certain embodiments the molecular weight of a moiety $P^1$, $P^2$, $P^3$ and $P^4$ of formula (A) ranges independently of each other from 5 to 30 kDa, such as from 5 to 25 kDa or from 8 to 20 kDa. In certain embodiments the molecular weight of a moiety $P^1$, $P^2$, $P^3$ or $P^4$ may be about 5 kDa. In certain embodiments the molecular weight of a moiety $P^1$, $P^2$, $P^3$ or $P^4$ may be about 7 kDa. In certain embodiments the molecular weight of a moiety $P^1$, $P^2$, $P^3$ or $P^4$ may be about 10 kDa. In certain embodiments the molecular weight of a moiety $P^1$, $P^2$, $P^3$ or $P^4$ may be about 12 kDa. In certain embodiments the molecular weight of a moiety $P^1$, $P^2$, $P^3$ or $P^4$ may be about 15 kDa. In certain embodiments the molecular weight of a moiety $P^1$, $P^2$, $P^3$ or $P^4$ may be about 20 kDa. In certain embodiments the molecular weight of a moiety $P^1$, $P^2$, $P^3$ or $P^4$ may be about 25 kDa. In certain embodiments the molecular weight of a moiety $P^1$, $P^2$, $P^3$ or $P^4$ may be about 30 kDa. In certain embodiments the molecular weight of a moiety $P^1$, $P^2$, $P^3$ or $P^4$ may be 7 kDa. In certain embodiments the molecular weight of a moiety $P^1$, $P^2$, $P^3$ or $P^4$ may be 10 kDa. In certain embodiments the molecular weight of a moiety $P^1$, $P^2$, $P^3$ or $P^4$ may be 12 kDa. In certain embodiments the molecular weight of a moiety $P^1$, $P^2$, $P^3$ or $P^4$ may be 15 kDa. In certain embodiments the molecular weight of a moiety $P^1$, $P^2$, $P^3$ or $P^4$ m be 20 kDa. In certain embodiments the molecular weight of a moiety $P^1$, $P^2$, $P^3$ or $P^4$ may be 25 kDa. In certain embodiments the molecular weight of a moiety $P^1$, $P^2$, $P^3$ or $P^4$ may be 30 kDa.

In certain embodiments $P^1$. $P^2$, $P^3$ and $P^4$ of formula (A) have the same structure.

In certain embodiments BP of formula (A) is —N<.

In certain embodiments $BP^2$ and $BP^2$ of formula (A) have the same structure. In certain embodiments $BP^2$ and $BP^2$ of formula (A) are both —CH<.

In certain embodiments $C^1$ and $C^2$ of formula (A) have the same structure. In certain embodiments $C^1$ and $C^2$ of formula (A) are $C_{1-50}$ alkyl interrupted by one or more of the groups selected from the group consisting of —O—, —$C(O)N(R^{10})$— and 3- to 10 membered heterocyclyl; wherein the 3- to 10 membered heterocyclyl is substituted with at least one oxo (=O).

In certain embodiments $C^1$ and $C^2$ of formula (A) are of formula (A-a)

(A-a)

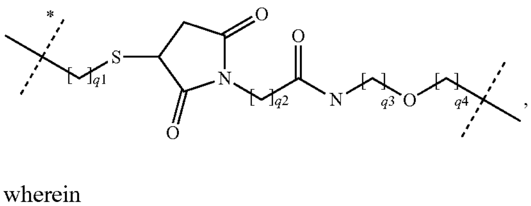

wherein the dashed line marked with the asterisk indicates attachment to $BP^1$;

the unmarked dashed line indicates attachment to $BP^2$ or $BP^3$, respectively;

q1 is selected from the group consisting of 1, 2, 3, 4, 5, 6, 7 and 8;

q2 is selected from the group consisting of 1, 2, 3, 4, and 5;

q3 is selected from the group consisting of 1, 2, 3, 4, 5, 6, 7 and 8; and q4 is selected from the group consisting of 1, 2 and 3.

In certain embodiments q1 of formula (A-a) is selected from the group consisting of 4, 5, 6, 7, and 8. In certain embodiments q1 of formula (A-a) is selected from the group consisting of 5, 6 and 7. In certain embodiments q1 of formula (A-a) is 1. In certain embodiments q1 of formula (A-a) is 2. In certain embodiments q1 of formula (A-a) is 3. In certain embodiments q1 of formula (A-a) is 4. In certain embodiments q1 of formula (A-a) is 5. In certain embodiments q of formula (A-a) is 6. In certain embodiments q1 of formula (A-a) is 7. In certain embodiments q1 of formula (A-a) is 8.

In certain embodiments q2 of formula (A-a) is selected from the group consisting of 1, 2 and 3. In certain embodiments q2 of formula (A-a) is 1. In certain embodiments q2 of formula (A-a) is 2. In certain embodiments q2 of formula (A-a) is 3. In certain embodiments q2 of formula (A-a) is 4. In certain embodiments q2 of formula (A-a) is 5.

In certain embodiments q3 of formula (A-a) is selected from the group consisting of 2, 3, 4, and 5. In certain embodiments q3 of formula (A-a) is selected from the group consisting of 2, 3 and 4. In certain embodiments q3 of formula (A-a) is 1. In certain embodiments q3 of formula (A-a) is 2. In certain embodiments q3 of formula (A-a) is 3.

In certain embodiments m of formula (A-b) is 0. In certain embodiments m of formula (A-b) is 1.

In certain embodiments p of formula (A-b) is an integer ranging from 115 to 680. In certain embodiments p of formula (A-b) is an integer ranging from 115 to 560. In certain embodiments p of formula (A-b) is an integer ranging from 185 to 450. In certain embodiments p of formula (A-b) is about 115. In certain embodiments p of formula (A-b) is about 160. In certain embodiments p of formula (A-b) is about 225. In certain embodiments p of formula (A-b) is about 270. In certain embodiments p of formula (A-b) is about 340. In certain embodiments p of formula (A-b) is about 450. In certain embodiments p of formula (A-b) is about 560.

In certain embodiments q of formula (A-b) is 1. In certain embodiments q of formula (A-b) is 2. In certain embodiments q of formula (A-b) is 3. In certain embodiments q of formula (A-b) is 4. In certain embodiments q of formula (A-b) is 5. In certain embodiments q of formula (A-b) is 6.

In certain embodiments —Z comprises a moiety of formula (A-1c):

(A-c)

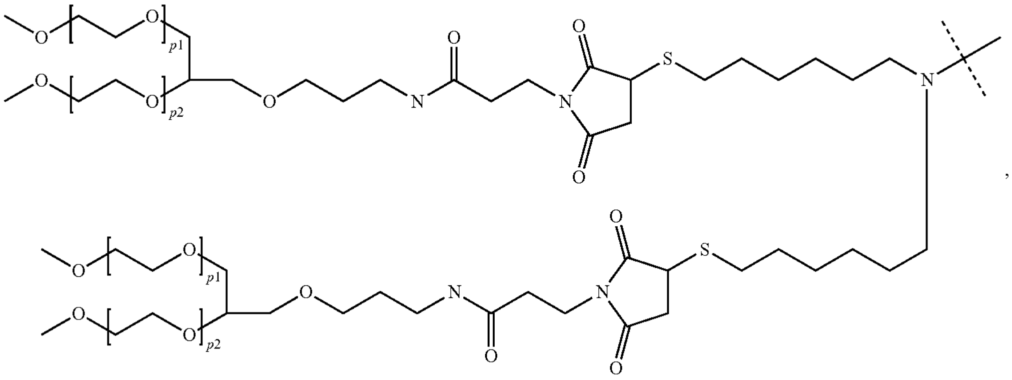

,

In certain embodiments q3 of formula (A-a) is 4. In certain embodiments q3 of formula (A-a) is 5. In certain embodiments q3 of formula (A-a) is 6. In certain embodiments q3 of formula (A-a) is 7. In certain embodiments q3 of formula (A-a) is 8.

In certain embodiments q4 of formula (A-a) is 1. In certain embodiments q4 of formula (A-a) is 2. In certain embodiments q4 of formula (A-a) is 3.

In certain embodiments $P^1$, $P^2$, $P^3$ and $P^4$ of formula (A) are independently of each other of formula (A-b)

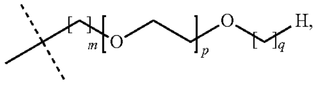

(A-b)

wherein the dashed line indicates attachment to the remainder of —Z;

m is 0 or 1;

p is an integer ranging from 70 to 900; and q is selected from the group consisting of 1, 2, 3, 4, 5, and 6.

wherein p1, p2, p3, p4 are independently of each other an integer ranging from 70 to 900.

In certain embodiments p1 of formula (A-c) is an integer ranging from 115 to 680. In certain embodiments p1 of formula (A-c) is an integer ranging from 115 to 560. In certain embodiments p1 of formula (A-c) is an integer ranging from 185 to 450. In certain embodiments p1 of formula (A-c) is an integer ranging from 220 to 240. In certain embodiments p1 of formula (A-c) is about 115. In certain embodiments p1 of formula (A-c) is about 160. In certain embodiments p1 of formula (A-c) is about 225. In certain embodiments p1 of formula (A-c) is about 270. In certain embodiments p1 of formula (A-c) is about 340. In certain embodiments p1 of formula (A-c) is about 450. In certain embodiments p1 of formula (A-c) is about 560.

In certain embodiments p2 of formula (A-c) is an integer ranging from 115 to 680. In certain embodiments p2 of formula (A-c) is an integer ranging from 115 to 560. In certain embodiments p2 of formula (A-c) is an integer ranging from 185 to 450. In certain embodiments p2 of formula (A-c) is an integer ranging from 220 to 240. In certain embodiments p2 of formula (A-c) is about 115. In certain embodiments p2 of formula (A-c) is about 160. In certain embodiments p2 of formula (A-c) is about 225. In certain embodiments p2 of formula (A-c) is about 270. In certain embodiments p2 of formula (A-c) is about 340. In certain embodiments p2 of formula (A-c) is about 450. In certain embodiments p2 of formula (A-c) is about 560.

In certain embodiments p3 of formula (A-c) is an integer ranging from 115 to 680. In certain embodiments p3 of formula (A-c) is an integer ranging from 115 to 560. In certain embodiments p3 of formula (A-c) is an integer ranging from 185 to 450. In certain embodiments p3 of formula (A-c) is an integer ranging from 220 to 240. In certain embodiments p3 of formula (A-c) is about 115. In certain embodiments p3 of formula (A-c) is about 160. In certain embodiments p3 of formula (A-c) is about 225. In certain embodiments p3 of formula (A-c) is about 270. In certain embodiments p3 of formula (A-c) is about 340. In certain embodiments p3 of formula (A-c) is about 450. In certain embodiments p3 of formula (A-c) is about 560.

In certain embodiments p4 of formula (A-c) is an integer ranging from 115 to 680. In certain embodiments p4 of formula (A-c) is an integer ranging from 115 to 560. In certain embodiments p4 of formula (A-c) is an integer ranging from 185 to 450. In certain embodiments p4 of formula (A-c) is an integer ranging from 220 to 240. In certain embodiments p4 of formula (A-c) is about 115. In certain embodiments p4 of formula (A-c) is about 160. In certain embodiments p4 of formula (A-c) is about 225. In certain embodiments p4 of formula (A-c) is about 270. In certain embodiments p4 of formula (A-c) is about 340. In certain embodiments p4 of formula (A-c) is about 450. In certain embodiments p4 of formula (A-c) is about 560.

In certain embodiments p1, p2, p3 of formula (A-c) and p4 are identical. In certain embodiments p1, p2, p3 and p4 range from 220 to 240.

In one embodiment —Z is a moiety as disclosed in WO 2012/02047 A1, which is herewith incorporated by reference.

In another embodiment —Z is a moiety as disclosed in WO 2013/024048 A1, which is herewith incorporated by reference.

In certain embodiments —Z is water-insoluble. In certain embodiments —Z is a hydrogel.

In certain embodiments such hydrogel comprises a polymer selected from the group consisting of 2-methacryloyloxyethyl phosphoyl cholins, poly(acrylic acids), poly(acrylates), poly(acrylamides), poly(alkyloxy) polymers, poly (amides), poly(amidoamines), poly(amino acids), poly (anhydrides), poly(aspartamides), poly(butyric acids), poly (glycolic acids), polybutylene terephthalates, poly (caprolactones), poly(carbonates), poly(cyanoacrylates), poly(dimethylacrylamides), poly(esters), poly(ethylenes), poly(alkylene glycols), such as poly(ethylene glycols) and poly(propylene glycol), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly (hydroxypropyloxazolines), poly(iminocarbonates), poly (lactic acids), poly(lactic-co-glycolic acids), poly (methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments —Z is a poly(alkylene glycol)-based or hyaluronic acid-based hydrogel.

In certain embodiments —Z is a poly(propylene glycol)-based hydrogel.

In certain embodiments —Z is a PEG-based hydrogel.

In certain embodiments —Z is a PEG-based hydrogel as disclosed in WO2011/012715A1 or WO2014/056926A1, which are herewith incorporated by reference.

In certain embodiments —Z is a hyaluronic acid-based hydrogel.

In certain embodiments —Z is a hyaluronic acid-based hydrogel as disclosed in WO2018/175788A1, which is herewith incorporated by reference.

A moiety $-L^1-$ may be attached to -D through the IL-2 moiety, in particular through an amino acid residue of the IL-2 moiety, or through a modifying moiety $M_{mod}$ present in -D. In one embodiment $-L^1-$ is attached to -D through the IL-2 moiety, in particular through an amino acid residue of the IL-2 moiety. In another embodiment $-L^1-$ is attached to -D through a modifying moiety $M_{mod}$ present in -D. It is understood that one or more moieties $-L^1-$ may be attached to a moiety $M_{mod}$.

In one embodiment all moieties $-L^1-$ present in the IL-2 conjugates of the present invention are attached to an amino acid residue of -D.

If $-L^1-$ is attached to an amino acid residue of the IL-2 moiety, such amino acid residue may be a proteinogenic or non-proteinogenic amino acid residue of -D. In one embodiment $-L^1-$ is attached to a non-proteinogenic amino acid residue, preferably to a non-proteinogenic amino acid as described above. In another embodiment attachment of $-L^1-$ is to a proteinogenic amino acid residue. If attachment occurs at a proteinogenic amino acid residue, said proteinogenic amino acid residue is in certain embodiments selected from the group consisting of cysteine, methionine, histidine, lysine, tryptophan, serine, threonine, tyrosine, aspartic acid, glutamic acid, glutamine and arginine. In certain embodiments such proteinogenic amino acid residue is selected from the group consisting of cysteine, histidine, lysine, tryptophan, serine, threonine, tyrosine, aspartic acid, glutamic acid and arginine.

In one embodiment of $-L^1-$ is attached to a cysteine residue of -D, such as to a cysteine residue selected from the group consisting of C57 and C104 based on SEQ ID NO: 2 or to the corresponding positions of homologs or variants of SEQ ID NO:2. In case the homologs or variants of IL-2 comprise one or more additional cysteine residues compared to SEQ ID NO:2 attachment may also occur at such cysteine residue, which may be naturally occurring or may have been the result of an addition, insertion or mutation. It is understood that one or two of the cysteine residues of SEQ ID NO:2 may be used for attachment of one or two moieties —Z to -D, respectively. If the IL-2 moiety is a homolog or variant of SEQ ID NO:2 and has more cysteine residues than the IL-2 moiety of SEQ ID NO:2, more than two cysteine residues may be used for attachment of —Z, i.e. up to the maximum number of cysteine residues present in such homolog or variant may be used for attachment of —Z. In one embodiment one moiety —Z is attached to one cysteine residue. In another embodiment a total of two moieties —Z are attached to two cysteine residues.

In another embodiment $-L^1-$ is attached to a histidine residue of -D, such as to a histidine residue selected from the group consisting of H15, H54 and H78 based on SEQ ID NO: 2 or to the corresponding positions of homologs or variants of SEQ ID NO:2. In case the homologs or variants of IL-2 comprise one or more additional histidine residues compared to SEQ ID NO:2 attachment may also occur at such histidine residue, which may be naturally occurring or may have been the result of an addition, insertion or mutation. It is understood that one, two or three of the histidine residues of SEQ ID NO:2 may be used for attachment of one, two or three moieties $-L^1-$, respectively. If the IL-2 moiety is a homolog or variant of SEQ ID NO:2 and has more histidine residues than the IL-2 moiety of SEQ ID NO:2, more than three histidine residues may be used for attachment of $-L^1-$ to -D, i.e. up to the maximum number of histidine residues present in such homolog or variant may be used for attachment of $-L^1-$. In one embodiment one moiety $-L^1-$ is attached to one histidine residue. In another embodiment a total of two moieties $-L^1-$ are attached to two histidine residues. In another embodiment a total of three moieties $-L^1-$ are attached to three histidine residues.

In another embodiment $-L^1-$ is attached to a lysine residue, such as to a lysine residue selected from the group consisting of K7, K8, K31, K34, K42, K47, K48, K53, K63, K75 or K96 based on SEQ ID NO: 2 or to the corresponding positions of homologs or variants of SEQ ID NO:2. In case the homologs or variants of IL-2 comprise one or more additional lysine residues compared to SEQ ID NO:2 attachment may also occur at such lysine residues, which may be naturally occurring or may have been the result of an addition, insertion or mutation. It is understood that 1, 2, 3, 4, 5, 6, 7, 8, 9, 10 or 11 of the lysine residues of SEQ ID NO:2 may be used for attachment of 1, 2, 3, 4, 5, 6, 7, 8, 9, 10 or 11 moieties $-L^1-$, respectively. If the IL-2 moiety is a homolog or variant of SEQ ID NO:2 and has more lysine residues than the IL-2 moiety of SEQ ID NO:2, more than 11 lysine residues may be used for attachment of $-L^1-$, i.e. up to the maximum number of lysine residues present in such homolog or variant may be used for attachment of $-L^1-$. In one embodiment one moiety $-L^1-$ is attached to one lysine residue. In another embodiment a total of two moieties $-L^1-$ are attached to two lysine residues. In another embodiment a total of three moieties $-L^1-$ are attached to three lysine residues. In another embodiment a total of four moieties $-L^1-$ are attached to four lysine residues. In another embodiment a total of five moieties $-L^1-$ are attached to five lysine residues. In another embodiment a total of six moieties $-L^1-$ are attached to six lysine residues.

In another embodiment $-L^1-$ is attached to a tryptophan residue, such as to the tryptophan residue at position W120 based on SEQ ID NO: 2 or to the corresponding positions of homologs or variants of SEQ ID NO:2. In case the homologs or variants of IL-2 comprise one or more additional tryptophan residues compared to SEQ ID NO:2 attachment may also occur at such tryptophan residue, which may be naturally occurring or may have been the result of an addition, insertion or mutation. If the IL-2 moiety is a homolog or variant of SEQ ID NO:2 and has more tryptophan residues than the IL-2 moiety of SEQ ID NO:2, more than one tryptophan residues may be used for attachment of $-L^1-$, i.e. up to the maximum number of tryptophan residues present in such homolog or variant may be used for attachment of $-L^1-$. In one embodiment one moiety-$L^1-$ is attached to one tryptophan residue.

In another embodiment $-L^1-$ is attached to a serine residue, such as to a serine residue selected from the group consisting of S3, S4, S5, S74, S86, S98, S124, S126 and S129 based on SEQ ID NO: 2 or to the corresponding positions of homologs or variants of SEQ ID NO:2. In case the homologs or variants of IL-2 comprise one or more additional serine residues compared to SEQ ID NO:2 attachment may also occur at such serine residue, which may be naturally occurring or may have been the result of an addition, insertion or mutation. It is understood that 1, 2, 3, 4, 5, 6, 7, 8 or 9 of the serine residues of SEQ ID NO:2 may be used for attachment of $-L^1-$. If the IL-2 moiety is a homolog or variant of SEQ ID NO:2 and has more serine residues than the IL-2 moiety of SEQ ID NO:2, more than 9 serine residues may be used for attachment of $-L^1-$ to -D, i.e. up to the maximum number of serine residues present in such homolog or variant may be used for attachment of $-L^1-$. In one embodiment one moiety $-L^1-$ is attached to one serine residue. In another embodiment a total of two moieties $-L^1-$ are attached to two serine residues. In another embodiment a total of three moieties $-L^1-$ are attached to three serine residues. In another embodiment a total of four moieties $-L^1-$ are attached to four serine residues. In another embodiment a total of five moieties $-L^1-$ are attached to five serine residues. In another embodiment a total of six moieties $-L^1-$ are attached to six serine residues.

In another embodiment $-L^1-$ is attached to a threonine residue, such as to a threonine residue selected from the group consisting of T2, T6, T9, T36, T40, T50, T100, T102, T110, T112, T122, T130 and T132 based on SEQ ID NO: 2 or to the corresponding positions of homologs or variants of SEQ ID NO:2. In case the homologs or variants of IL-2 comprise one or more additional threonine residues compared to SEQ ID NO:2 attachment may also occur to such threonine residue, which may be naturally occurring or may have been the result of an addition, insertion or mutation. It is understood that 1, 2, 3, 4, 5, 6, 7, 8, 9, 10, 11, 12 or 13 of the threonine residues of SEQ ID NO:2 may be used for attachment of 1, 2, 3, 4, 5, 6, 7, 8, 9, 10, 11, 12 or 13 moieties $-L^1-$, respectively. If the IL-2 moiety is a homolog or variant of SEQ ID NO:2 and has more threonine residues than the IL-2 moiety of SEQ ID NO:2, more than 13 threonine residues may be used for attachment of $-L^1-$ to -D, i.e. up to the maximum number of threonine residues present in such homolog or variant may be used for attachment $-L^1-$. In one embodiment one moiety $-L^1-$ is attached to one threonine residue. In another embodiment a total of two moieties $-L^1-$ are attached to two threonine residues. In another embodiment a total of three moieties $-L^1-$ are attached to three threonine residues. In another embodiment a total of four moieties $-L^1-$ are attached to four threonine residues. In another embodiment a total of five moieties $-L^1-$ are attached to five threonine residues. In another embodiment a total of six moieties $-L^1-$ are attached to six threonine residues.

In another embodiment $-L^1-$ is attached to a tyrosine residue, such as to a tyrosine residue selected from the group consisting of Y30, Y44 and Y106 based on SEQ ID NO: 2 or to the corresponding positions of homologs or variants of SEQ ID NO:2. In case the homologs or variants of IL-2 comprise one or more additional tyrosine residues compared to SEQ ID NO:2 attachment may also occur at such tyrosine residue, which may be naturally occurring or may have been the result of an addition, insertion or mutation. It is understood that 1, 2 or 3 of the tyrosine residues of SEQ ID NO:2 may be used for attachment of 1, 2 or 3 moieties $-L^1-$ to -D. If the IL-2 moiety is a homolog or variant of SEQ ID NO:2 and has more tyrosine residues than the IL-2 moiety of SEQ ID NO:2, more than 3 tyrosine residues may be used for attachment of $-L^1-$, i.e. up to the maximum number of tyrosine residues present in such homolog or variant may be used for attachment of $-L^1-$ to -D. In one embodiment one moiety $-L^1-$ is attached to one tyrosine residue. In another embodiment a total of two moieties $-L^1-$ are attached to two tyrosine residues. In another embodiment a total of three moieties $-L^1-$ are attached to three tyrosine residues.

In another embodiment $-L^1-$ is attached to an aspartic acid residue, such as to an aspartic acid residue selected from the group consisting of D19, D83 and D108 based on SEQ ID NO: 2 or to the corresponding positions of homologs or variants of SEQ ID NO:2. In case the homologs or variants of IL-2 comprise one or more additional aspartic acid residues compared to SEQ ID NO:2 attachment may also be to such aspartic acid residues, which may be naturally occurring or may have been the result of an addition, insertion or mutation. It is understood that 1, 2 or 3 of the aspartic acid residues of SEQ ID NO:2 may be used for attachment of 1, 2 or 3 moieties $-L^1-$, respectively. If the IL-2 moiety is a homolog or variant of SEQ ID NO:2 and has more aspartic acid residues than the IL-2 moiety of SEQ ID NO:2, more than 3 aspartic acid residues may be used for attachment of $-L^1-$, i.e. up to the maximum number of aspartic acid residues present in such homolog or variant may be used for attachment of $-L^1-$ to -D. In one embodiment one moiety $-L^1-$ is attached to one aspartic acid residue. In another embodiment a total of two moieties $-L^1-$ are attached to two aspartic acid residues. In another embodiment a total of three moieties $-L^1-$ are attached to three aspartic acid residues.

In another embodiment $-L^1-$ is attached to a glutamic acid residue, such as to a glutamic acid residue selected from the group consisting of E14, E51, E59, E60, E61, E66, E67, E94, E99, E105, E109 and E115 based on SEQ ID NO: 2 or to the corresponding positions of homologs or variants of SEQ ID NO:2. In case the homologs or variants of IL-2 comprise one or more additional glutamic acid residues compared to SEQ ID NO:2 attachment may also be to such glutamic acid residue, which may be naturally occurring or may have been the result of an addition, insertion or mutation. It is understood that 1, 2, 3, 4, 5, 6, 7, 8, 9, 10, 11 or 12 of the glutamic acid residues of SEQ ID NO:2 may be used for attachment of 1, 2, 3, 4, 5, 6, 7, 8, 9, 10, 11 or 12 moieties $-L^1-$. If the IL-2 moiety is a homolog or variant of SEQ ID NO:2 and has more glutamic acid residues than the IL-2 moiety of SEQ ID NO:2, more than 12 glutamic acid residues may be used for attachment of $-L^1-$, i.e. up to the maximum number of glutamic acid residues present in such homolog or variant may be used for attachment of $-L^1-$. In one embodiment one moiety $-L^1-$ is attached to one glutamic acid residue. In another embodiment a total of two moieties $-L^1-$ are attached to two glutamic acid residues. In another embodiment a total of three moieties $-L^1-$ are attached to three glutamic acid residues. In another embodiment a total of four moieties $-L^1-$ are attached to four glutamic acid residues.

In another embodiment a total of five moieties $-L^1-$ are attached to five glutamic acid residues. In another embodiment a total of six moieties $-L^1-$ are attached to six glutamic acid residues.

In another embodiment $-L^1-$ is attached to an arginine residue, such as to an arginine residue selected from the group consisting of R37, R80, R82 and R119 based on SEQ ID NO: 2 or to the corresponding positions of homologs or variants of SEQ ID NO:2. In case the homologs or variants of IL-2 comprise one or more additional arginine residues compared to SEQ ID NO:2 attachment may also occur to such arginine residue, which may be naturally occurring or may have been the result of an addition, insertion or mutation. It is understood that 1, 2, 3 or 4 of the arginine residues of SEQ ID NO:2 may be used for attachment of 1, 2, 3 or 4 moieties $-L^1-$. If the IL-2 moiety is a homolog or variant of SEQ ID NO:2 and has more arginine residues than the IL-2 moiety of SEQ ID NO:2, more than 4 arginine residues may be used for attachment of $-L^1-$, i.e. up to the maximum number of arginine residues present in such homolog or variant may be used for attachment of $-L^1-$. In one embodiment one moiety $-L^1-$ is attached to one arginine residue. In another embodiment a total of two moieties $-L^1-$ are attached to two arginine residues. In another embodiment a total of three moieties $-L^1-$ are attached to four arginine residues. In another embodiment a total of four moieties $-L^1-$ are attached to four tyrosine residues.

In another embodiment at least one moiety $-L^1-$ is attached to an amino acid residue of -D and the remaining moiety/moieties $-L^1-$ are attached to a modifying moiety present in -D.

In another embodiment all moieties $-L^1-$ present in the IL-2 conjugates of the present invention are attached to a modifying moiety present in -D. In one embodiment one moiety $-L^1-$ is attached to one modifying moiety of -D. In another embodiment a total of two moieties $-L^1-$ are attached to one modifying moiety, i.e. to the same modifying moiety. In another embodiment a total of three moieties $-L^1-$ are attached to one modifying moiety. In another embodiment a total of four moieties $-L^1-$ are attached to one modifying moiety. In another embodiment a total of five moieties $-L^1-$ are attached to one modifying moiety. In another embodiment a total of six moieties $-L^1-$ are attached to one modifying moiety. In another embodiment a total of two moieties $-L^1-$ are attached to two modifying moieties, i.e. one moiety $-L^1-$ per modifying moiety. In another embodiment a total of three moieties $-L^1-$ are attached to three modifying moieties, i.e. one moiety $-L^1-$ per modifying moiety. In another embodiment a total of four moieties $-L^1-$ are attached to four modifying moieties, i.e. one moiety $-L^1-$ is attached per modifying moiety. In another embodiment a total of five moieties $-L^1-$ are attached to five modifying moieties, i.e. one moiety per modifying moiety. In another embodiment a total of six moieties $-L^1-$ are attached to six modifying moieties, i.e. one $-L^1-$ is attached per modifying moiety.

In one embodiment $-L^1-$ has a structure as disclosed in WO 2009/095479 A2. Accordingly, in one embodiment the moiety $-L^1-$ is of formula (II):

(II)

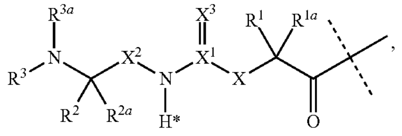

wherein the dashed line indicates attachment to a nitrogen of -D by forming an amide bond;

$-X-$ is $-C(R^4R^{4a})-$; $-N(R^4)-$; $-O-$; $-C(R^4R^{4a})-C(R^5R^{5a})-$; $-C(R^5R^{5a})-C(R^4R^{4a})-$; $-C(R^4R^{4a})-N(R^6)-$; $-N(R^6)-C(R^4R^{4a})-$; $-C(R^4R^{4a})-O-$; $-O-C(R^4R^{4a})-$; or $-C(R^7R^{7a})-$;

$X^1$ is C; or S(O);

$-X^2-$ is $-C(R^8R^{8a})-$; or $-C(R^8R^{8a})-C(R^9R^{9a})$;

$=X^3$ is $=O$; $=S$; or $=N-CN$;

$-R^1$, $-R^{1a}$, $-R^2$, $-R^{2a}$, $-R^4$, $-R^{4a}$, $-R^5$, $-R^{5a}$, $-R^6$, $-R^8$, $-R^{8a}$, $-R^9$, $-R^{9a}$ are independently selected from the group consisting of $-H$; and $C_{1-6}$ alkyl;

—$R^3$, —$R^{3a}$ are independently selected from the group consisting of —H; and $C_{1-6}$ alkyl, provided that in case one of —$R^3$, —$R^{3a}$ or both are other than —H they are connected to N to which they are attached through an $SP^3$-hybridized carbon atom;

—$R^7$ is —$N(R^{10}R^{10a})$; or —$NR^{10}$—(C═O)—$R^{11}$;

—$R^{7a}$, —$R^{10}$, —$R^{10a}$, —$R^{11}$ are independently of each other —H; or $C_{1-6}$ alkyl;

optionally, one or more of the pairs —$R^{1a}$/—$R^{4a}$, —$R^{1a}$/—$R^{5a}$, —$R^{1a}$/—$R^{7a}$, —$R^{4a}$/—$R^{5a}$, —$R^{8a}$/—$R^{9a}$ form a chemical bond;

optionally, one or more of the pairs —$R^1$/—$R^{1a}$, —$R^2$/—$R^{2a}$, —$R^4$/—$R^{4a}$, —$R^5$/—$R^{5a}$, —$R^8$/—$R^{8a}$, —$R^9$/—$R^{9a}$ are joined together with the atom to which they are attached to form a $C_{3-10}$ cycloalkyl; or 3- to 10-membered heterocyclyl;

optionally, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^8$/—$R^9$, —$R^2$/—$R^3$ are joined together with the atoms to which they are attached to form a ring A;

optionally, $R^3$/$R^{3a}$ are joined together with the nitrogen atom to which they are attached to form a 3- to 10-membered heterocycle;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein -$L^1$- is substituted with at least one -$L^2$-Z and wherein -$L^1$- is optionally further substituted, provided that the hydrogen marked with the asterisk in formula (II) is not replaced by -$L^2$-Z or a substituent.

Preferably -$L^1$- of formula (II) is substituted with one moiety -$L^2$-Z.

In one embodiment -$L^1$- of formula (II) is not further substituted.

It is understood that if —$R^3$/—$R^{3a}$ of formula (II) are joined together with the nitrogen atom to which they are attached to form a 3- to 10-membered heterocycle, only such 3- to 10-membered heterocycles may be formed in which the atoms directly attached to the nitrogen are $SP^3$-hybridized carbon atoms. In other words, such 3- to 10-membered heterocycle formed by —$R^3$/—$R^{3a}$ together with the nitrogen atom to which they are attached has the following structure:

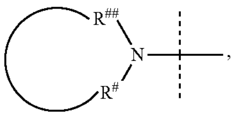, wherein the dashed line indicates attachment to the rest of -$L^1$-;

the ring comprises 3 to 10 atoms comprising at least one nitrogen; and $R^{\#}$and $R^{\#\#}$represent an $SP^3$-hydridized carbon atom.

It is also understood that the 3- to 10-membered heterocycle may be further substituted.

Exemplary embodiments of suitable 3- to 10-membered heterocycles formed by —$R^3$/—$R^{3a}$ of formula (II) together with the nitrogen atom to which they are attached are the following:

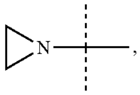, 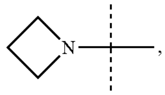, 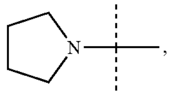,

-continued

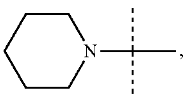, 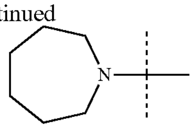,

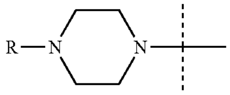 and 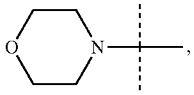, wherein dashed lines indicate attachment to the rest of the molecule; and —R is selected from the group consisting of —H and $C_{1-6}$ alkyl.

-$L^1$- of formula (II) may optionally be further substituted. In general, any substituent may be used as far as the cleavage principle is not affected, i.e. the hydrogen marked with the asterisk in formula (II) is not replaced and the nitrogen of the moiety

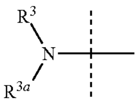

of formula (II) remains part of a primary, secondary or tertiary amine, i.e. —$R^3$ and —$R^{3a}$ are independently of each other —H or are connected to —N< through an $SP^3$-hybridized carbon atom.

In one embodiment —R or —$R^{1a}$ of formula (II) is substituted with -$L^2$-Z or -$L^2$-Z'. In another embodiment —$R^2$ or —$R^{2a}$ of formula (II) is substituted with -$L^2$-Z or -$L^2$-Z'. In another embodiment —$R^3$ or —$R^{3a}$ of formula (II) is substituted with -$L^2$-Z or -$L^2$-Z'. In another embodiment —$R^4$ of formula (II) is substituted with -$L^2$-Z or -$L^2$-Z'. In another embodiment —$R^5$ or —$R^{5a}$ of formula (II) is substituted with -$L^2$-Z or -$L^2$-Z'. In another embodiment —$R^6$ of formula (II) is substituted with -$L^2$-Z or -$L^2$-Z'. In another embodiment —$R^7$ or —$R^{7a}$ of formula (II) is substituted with -$L^2$-Z or -$L^2$-Z'. In another embodiment —$R^8$ or —$R^{8a}$ of formula (II) is substituted with -$L^2$-Z or -$L^2$-Z'. In another embodiment —$R^9$ or —$R^{9a}$ of formula (II) is substituted with -$L^2$-Z or -$L^2$-Z'.

In another embodiment -$L^1$- has a structure as disclosed in WO2016/020373A1. Accordingly, in another embodiment the moiety -$L^1$- is of formula (III):

(III)

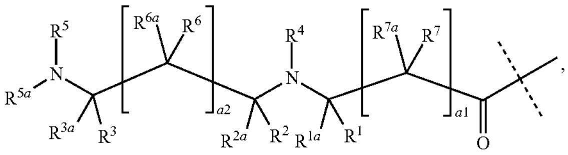, wherein the dashed line indicates attachment to a primary or secondary amine or hydroxyl of -D by forming an amide or ester linkage, respectively;

—$R^1$, —$R^{1a}$, —$R^2$, —$R^{2a}$, —$R^3$ and —$R^{3a}$ are independently of each other selected from the group consisting of —H, —$C(R^8R^{8a}R^{8b})$, —C(═O)$R^8$, —C≡N, —C(═$NR^8$)$R^{8a}$, —$CR^8$(═$CR^{8a}R^{8b}$), —C≡$CR^8$ and -T;

—$R^4$, —$R^5$ and —$R^{5a}$ are independently of each other selected from the group consisting of —H, —$C(R^9R^{9a}R^{9b})$ and -T;

a1 and a2 are independently of each other 0 or 1;

each —$R^6$, —$R^{6a}$, —$R^7$, —$R^{7a}$, —$R^8$, —$R^{8a}$, —$R^{8b}$, —$R^9$, —$R^{9a}$, —$R^{9b}$ are independently of each other selected from the group consisting of —H, halogen, —CN, —$COOR^{10}$, —$OR^{10}$, —$C(O)R^{10}$, —$C(O)N(R^{10}R^{10a})$, —$S(O)_2N(R^{10}R^{10a})$, —$S(O)N(R^{10}R^{10a})$, —$S(O)_2R^{10}$, —$S(O)R^{10}$, —$N(R^{10})S(O)_2N(R^{10a}R^{10b})$, —$SR^{10}$, —$N(R^{10}R^{10a})$, —$NO_2$, —$OC(O)R^{10}$, —$N(R^{10})C(O)R^{10a}$, —$N(R^{10})S(O)_2R^{10a}$, —$N(R^{10})S(O)R^{10a}$, —$N(R^{10})C(O)OR^{10a}$, —$N(R^{10})C(O)N(R^{10a}R^{10b})$, —$OC(O)N(R^{10}R^{10a})$, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —$C(O)N(R^{12})$—, —$S(O)_2N(R^{12})$—, —$S(O)N(R^{12})$—, —$S(O)_2$—, —S(O)—, —$N(R^{12})S(O)_2N(R^{12a})$—, —S—, —$N(R^{12})$—, —$OC(OR^{12})(R^{12a})$—, —$N(R^{12})C(O)N(R^{12a})$—, and —$OC(O)N(R^{12})$—;

each —$R^{10}$, $R^{10a}$, —$R^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —$C(O)N(R^{12})$—, —$S(O)_2N(R^{12})$—, —$S(O)N(R^{12})$—, —$S(O)_2$—, —S(O)—, —$N(R^{12})S(O)_2N(R^{12a})$—, —S—, —$N(R^{12})$—, —$OC(OR^{12})(R^{12a})$—, —$N(R^{12})C(O)N(R^{12a})$—, and —$OC(O)N(R^{12})$—;

each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T is independently optionally substituted with one or more —$R^{11}$, which are the same or different;

each —$R^{11}$ is independently of each other selected from halogen, —CN, oxo (=O), —$COOR^{13}$, —$OR^{13}$, —$C(O)R^{13}$, —$C(O)N(R^{13}R^{13a})$, —$S(O)_2N(R^{13}R^{13a})$, —$S(O)N(R^{13}R^{13a})$, —$S(O)_2R^{13}$, —$S(O)R^{13}$, —$N(R^{13})S(O)_2N(R^{13a}R^{13b})$, —$SR^{13}$, —$N(R^{13}R^{13a})$, —$NO_2$, —$OC(O)R^{13}$, —$N(R^{13})C(O)R^{13a}$, —$N(R^{13})S(O)_2R^{13a}$, —$N(R^{13})S(O)R^{13a}$, —$N(R^{13})C(O)OR^{13a}$, —$N(R^{13})C(O)N(R^{13a}R^{13b})$, —$OC(O)N(R^{13}R^{13a})$, and $C_{1-6}$ alkyl; wherein $C_{1-6}$ alkyl is optionally substituted with one or more halogen, which are the same or different;

each —$R^{12}$, —$R^{12a}$, —$R^{13}$, —$R^{13a}$, —$R^{13b}$ is independently selected from the group consisting of —H, and $C_{1-6}$ alkyl; wherein $C_{1-6}$ alkyl is optionally substituted with one or more halogen, which are the same or different;

optionally, one or more of the pairs —$R^1$/—$R^{1a}$, —$R^2$/$R^{2a}$, —$R^3$/—$R^{3a}$, —$R^6$/—$R^{6a}$, —$R^7$/—$R^{7a}$ are joined together with the atom to which they are attached to form a $C_{3-10}$ cycloalkyl or a 3- to 10-membered heterocyclyl;

optionally, one or more of the pairs -$R^1$/—$R^2$, —$R^1$/—$R^3$, —$R^1$/—$R^4$, —$R^1$/—$R^5$, —$R^1$/—$R^6$, —$R^1$/—$R^7$, —$R^2$/—$R^3$, —$R^2$/—$R^4$, —$R^2$/—$R^5$, —$R^2$/—$R^6$, —$R^2$/—$R^7$, —$R^3$/—$R^4$, —$R^3$/—$R^8$, —$R^3$/—$R^6$, —$R^3$/—$R^7$, —$R^4$/—$R^5$, —$R^4$/—$R^6$, —$R^4$/—$R^7$, —$R^5$/—$R^6$, —$R^5$/—$R^7$, —$R^6$/—$R^7$ are joint together with the atoms to which they are attached to form a ring A;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl;

wherein -$L^1$- is substituted with at least one -$L^2$-Z and wherein -$L^1$- is optionally further substituted.

The optional further substituents of -$L^1$- of formula (III) are preferably as described above.

Preferably -$L^1$- of formula (II) is substituted with one moiety -$L^2$-Z.

In one embodiment -$L^1$- of formula (III) is not further substituted.

In another embodiment -$L^1$- has a structure as disclosed in EP1536334B1, WO2009/009712A1, WO2008/034122A1, WO2009/143412A2, WO2011/082368A2, and U.S. Pat. No. 8,618,124B2, which are herewith incorporated by reference.

In another embodiment -$L^1$- has a structure as disclosed in U.S. Pat. No. 8,946,405B2 and U.S. Pat. No. 8,754,190B2, which are herewith incorporated by reference. Accordingly, in another embodiment -$L^1$- is of formula (IV):

(IV)

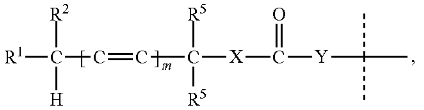

wherein the dashed line indicates attachment to -D through a functional group of -D selected from the group consisting of —OH, —SH and —$NH_2$;

m is 0 or 1;

at least one or both of —$R^1$ and —$R^2$ is/are independently of each other selected from the group consisting of —CN, —$NO_2$, optionally substituted aryl, optionally substituted heteroaryl, optionally substituted alkenyl, optionally substituted alkynyl, —$C(O)R^3$, —$S(O)R^3$, —$S(O)_2R^3$, and —$SR^4$, one and only one of —$R^1$ and —$R^2$ is selected from the group consisting of —H, optionally substituted alkyl, optionally substituted arylalkyl, and optionally substituted heteroarylalkyl;

—$R^3$ is selected from the group consisting of —H, optionally substituted alkyl, optionally substituted aryl, optionally substituted arylalkyl, optionally substituted heteroaryl, optionally substituted heteroarylalkyl, —$OR^9$ and —$N(R^9)_2$;

—$R^4$ is selected from the group consisting of optionally substituted alkyl, optionally substituted aryl, optionally substituted arylalkyl, optionally substituted heteroaryl, and optionally substituted heteroarylalkyl;

each —$R^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;

—$R^9$ is selected from the group consisting of —H and optionally substituted alkyl;

—Y— is absent and —X— is —O— or —S—; or

—Y— is —N(Q)$CH_2$— and —X— is —O—;

Q is selected from the group consisting of optionally substituted alkyl, optionally substituted aryl, optionally substituted arylalkyl, optionally substituted heteroaryl and optionally substituted heteroarylalkyl;

optionally, —$R^1$ and —$R^2$ may be joined to form a 3 to 8-membered ring; and optionally, both —$R^9$ together with the nitrogen to which they are attached form a heterocyclic ring;

wherein -$L^1$- is substituted with -$L^2$-Z and wherein -$L^1$- is optionally further substituted.

Only in the context of formula (IV) the terms used have the following meaning:

The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted. Optional substituents on any group, including the above, include halo, nitro, cyano, —OR, —SR, —$NR_2$, —OCOR, —NRCOR, —COOR, —$CONR_2$, —SOR, —$SO_2R$, —$SONR_2$, —$SO_2NR_2$, wherein each R is independently alkyl, alkenyl, alkynyl, aryl or heteroaryl, or two R groups taken together with the atoms to which they are attached form a ring.

Preferably -$L^1$- of formula (IV) is substituted with one moiety -$L^2$-Z.

In another embodiment -$L^1$- has a structure as disclosed in WO2013/036857A1, which is herewith incorporated by reference. Accordingly, in another embodiment -$L^1$- is of formula (V):

(V)

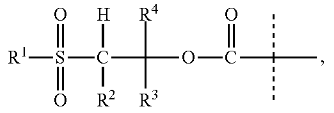

wherein the dashed line indicates attachment to -D through an amine functional group of -D;

—$R^1$ is selected from the group consisting of optionally substituted $C_1$-$C_6$ linear, branched, or cyclic alkyl; optionally substituted aryl; optionally substituted heteroaryl; alkoxy; and —$NR^5_2$;

—$R^2$ is selected from the group consisting of —H; optionally substituted $C_1$-$C_6$ alkyl; optionally substituted aryl; and optionally substituted heteroaryl;

—$R^3$ is selected from the group consisting of —H; optionally substituted $C_1$-$C_6$ alkyl; optionally substituted aryl; and optionally substituted heteroaryl;

—$R^4$ is selected from the group consisting of —H; optionally substituted $C_1$-$C_6$ alkyl; optionally substituted aryl; and optionally substituted heteroaryl;

each —$R^5$ is independently of each other selected from the group consisting of —H; optionally substituted $C_1$-$C_6$ alkyl; optionally substituted aryl; and optionally substituted heteroaryl; or when taken together two —$R^5$ can be cycloalkyl or cycloheteroalkyl;

wherein -$L^1$- is substituted with -$L^2$-Z and wherein -$L^1$- is optionally further substituted.

Only in the context of formula (V) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketne; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

Preferably $-L^1-$ of formula (V) is substituted with one moiety $-L^2-Z$.

In another embodiment $-L^1-$ has a structure as disclosed in U.S. Pat. No. 7,585,837B2, which is herewith incorporated by reference. Accordingly, in another embodiment $-L^1-$ is of formula (VI):

(VI)

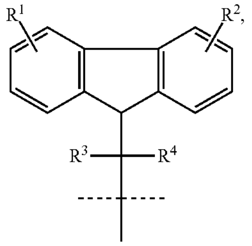

wherein the dashed line indicates attachment to -D through an amine functional group of -D;

$R^1$ and $R^2$ are independently selected from the group consisting of hydrogen, alkyl, alkoxy, alkoxyalkyl, aryl, alkaryl, aralkyl, halogen, nitro, $-S_3H$, $-SO_2NHR^5$, amino, ammonium, carboxyl, $PO_3H_2$, and $OPO_3H_2$;

$R^3$, $R^4$, and $R^5$ are independently selected from the group consisting of hydrogen, alkyl, and aryl;

wherein $-L^1-$ is substituted with $-L^2-Z$ o and wherein $-L^1-$ is optionally further substituted.

Suitable substituents for formulas (VI) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Only in the context of formula (VI) the terms used have the following meaning:

The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

Preferably $-L^1-$ of formula (VI) is substituted with one moiety $-L^2-Z$.

In another embodiment $-L^1-$ has a structure as disclosed in WO2002/089789A1, which is herewith incorporated by reference. Accordingly, in another embodiment $-L^1-$ is of formula (VII):

(VII)

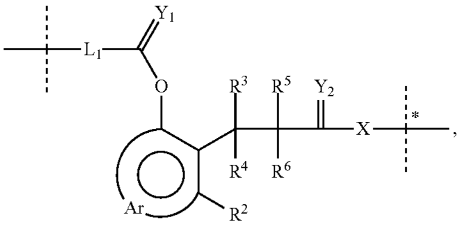

wherein the dashed line indicates attachment to -D through an amine functional group of -D;

$L_1$ is a bifunctional linking group, $Y_1$ and $Y_2$ are independently O, S or $NR^7$;

$R^2$, $R^3$, $R^4$, $R^5$, $R^6$ and $R^7$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula (VII) forms a multisubstituted aromatic hydrocarbon or a multi-substituted heterocyclic group;

X is a chemical bond or a moiety that is actively transported into a target cell, a hydrophobic moiety, or a combination thereof, y is 0 or 1;

wherein $-L^1-$ is substituted with $-L^2-Z$ and wherein $-L^1-$ is optionally further substituted.

Only in the context of formula (VII) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophene; alkoxy includes moieties such as methoxy; and phenoxy includes moieties such as 3-nitrophenoxy. Halo-shall be understood to include fluoro, chloro, iodo and bromo.

Preferably $-L^1-$ of formula (VII) is substituted with one moiety $-L^2-Z$.

In another embodiment $-L^1-$ comprises a substructure of formula (VIII)

(VIII)

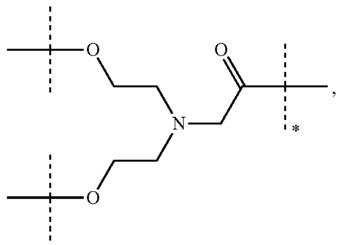

wherein the dashed line marked with the asterisk indicates attachment to a nitrogen of -D by forming an amide bond;

the unmarked dashed lines indicate attachment to the remainder of $-L^1-$; and wherein $-L^1-$ is substituted with $-L^2-Z$ and wherein $-L^1-$ is optionally further substituted.

Preferably $-L^1-$ of formula (VIII) is substituted with one moiety $-L^2-Z$.

In one embodiment $-L^1-$ of formula (VIII) is not further substituted.

In another embodiment $-L^1-$ comprises a substructure of formula (IX)

(IX)

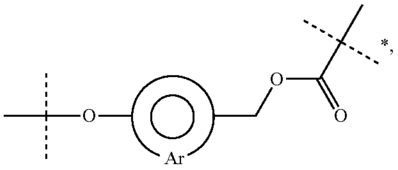

wherein the dashed line marked with the asterisk indicates attachment to a nitrogen of -D by forming a carbamate bond;

the unmarked dashed lines indicate attachment to the remainder of $-L^1-$; and wherein $-L^1-$ is substituted with $-L^2-Z$ and wherein $-L^1-$ is optionally further substituted.

Preferably $-L^1-$ of formula (IX) is substituted with one moiety $-L^2-Z$.

In one embodiment $-L^1-$ of formula (IX) is not further substituted.

In one embodiment $-L^1-$ is of formula (IX-a):

(IX-a)

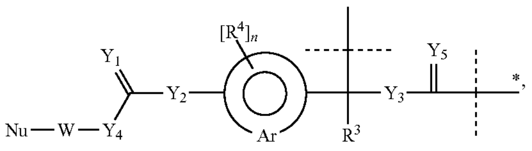

wherein the dashed line marked with the asterisk indicates attachment to a nitrogen of -D and the unmarked dashed line indicates attachment to $-L^2-Z$;

n is 0, 1, 2, 3, or 4;

$=Y_1$, is selected from the group consisting of $=O$ and $=S$;

$-Y_2-$ is selected from the group consisting of $-O-$ and $-S-$;

$-Y_3-$ is selected from the group consisting of $-O-$ and $-S-$;

$-Y_4-$ is selected from the group consisting of $-O-$, $-NR^5-$ and $-C(R^6R^{6a})-$;

$=Y_5$ is selected from the group consisting of $=O$ and $=S$;

$-R^3$, $-R^5$, $-R^6$, $-R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

$-R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl,2,3-dimethylbutyl and 3,3-dimethylpropyl;

—W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, $-C(O)N(R^7)-$, —O—, —S— and $-N(R^7)-$;

—Nu is a nucleophile selected from the group consisting of $-N(R^7R^{7a})$, $-N(R^7OH)$, $-N(R^7)-N(R^{7a}R^{7b})$, $-S(R^7)$, —COOH,

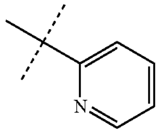, 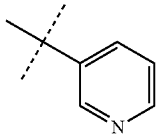, 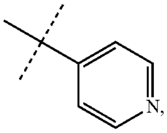,

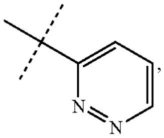, 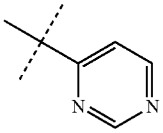, 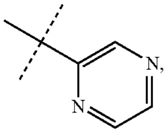,

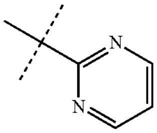, 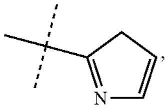, 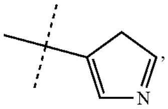,

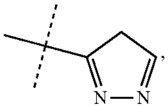, 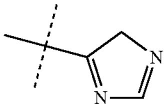 and

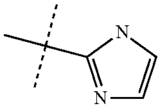;

—Ar— is selected from the group consisting of

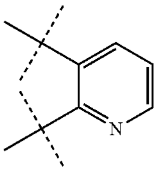, 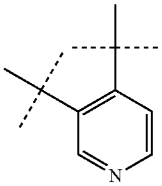,

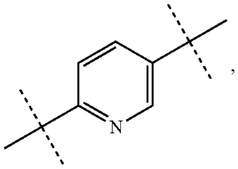, 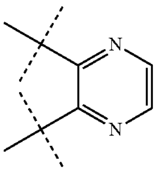,

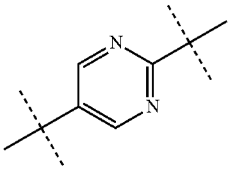, 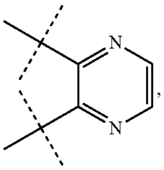,

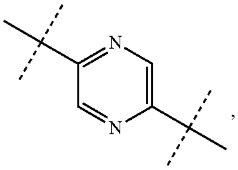, 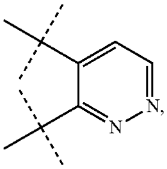,

-continued

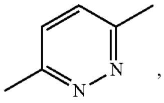, 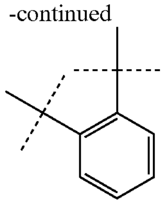, 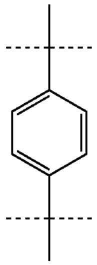,

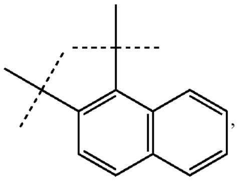, 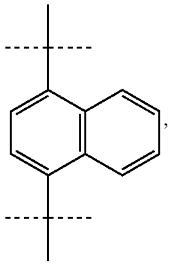,

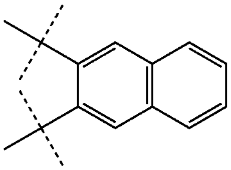, 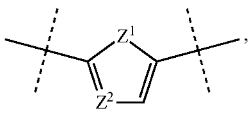,

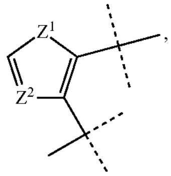, 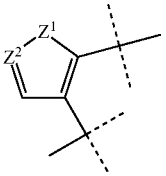 and

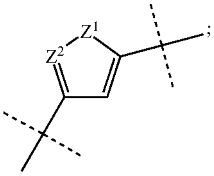;

wherein dashed lines indicate attachment to the remainder of $-L^1-$, $—Z^1—$ is selected from the group consisting of —O—, —S— and $—N(R^7)—$, and $—Z^2—$ is $—N(R^7)—$; and $—R^7$, $—R^{7a}$, $—R^{7b}$ are independently of each other selected from the group consisting of —H, $C_{1-6}$ alkyl, $C_{2-6}$ alkenyl and $C_{2-6}$ alkynyl;

wherein $-L^1-$ is optionally further substituted.

In one embodiment $-L^1-$ of formula (IX-a) is not further substituted.

In another embodiment $-L^1-$ is of formula (IX-b):

(IX-b)

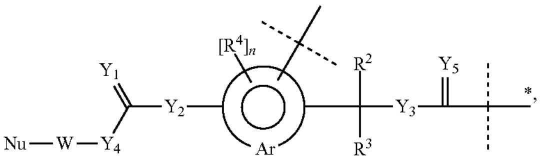

wherein the dashed line marked with the asterisk indicates attachment to a nitrogen of -D and the unmarked dashed line indicates attachment to $-L^2-Z$;

n is 0, 1, 2, 3, or 4;

$=Y_1$, is selected from the group consisting of =O and =S;

$—Y_2—$ is selected from the group consisting of —O— and —S—;

$—Y_3—$ is selected from the group consisting of —O— and —S—;

$—Y_4—$ is selected from the group consisting of —O—, $—NR^5—$ and $—C(R^6R^{6a})—$;

$=Y_5$ is selected from the group consisting of =O and =S;

$—R^2$, $—R^3$, $—R^5$, $—R^6$, $—R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

$—R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

—W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, $—C(O)N(R^7)—$, —O—, —S— and $—N(R^7)—$;

—Nu is a nucleophile selected from the group consisting of $—N(R^7R^{7a})$, $—N(R^7OH)$, $—N(R^7)—N(R^{7a}R^{7b})$, $—S(R^7)$, —COOH,

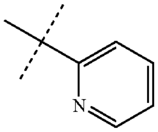, 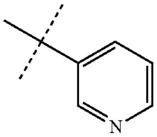, 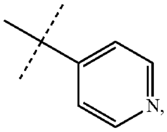,

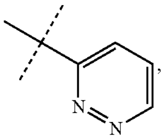, 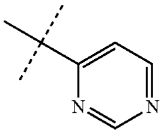, 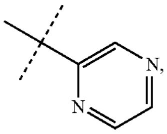,

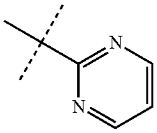, 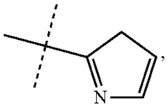, 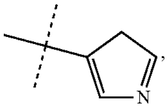,

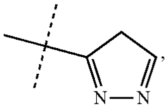, 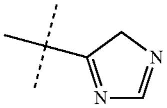 and

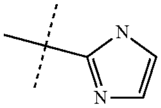;

—Ar— is selected from the group consisting of

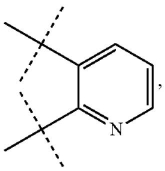,
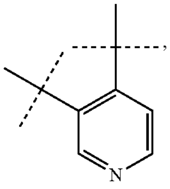,
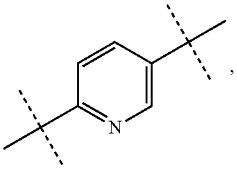,
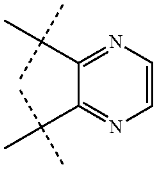,
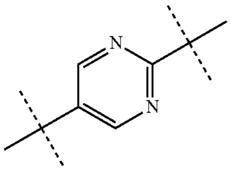,
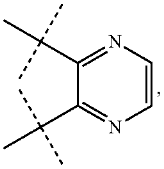,
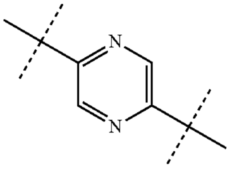,
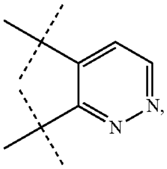,
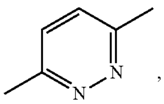,
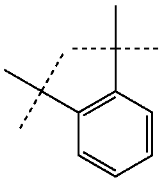,
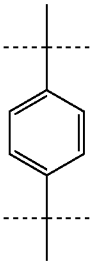,
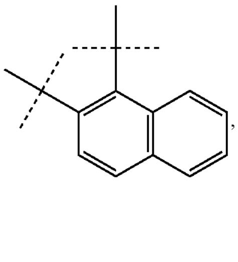,
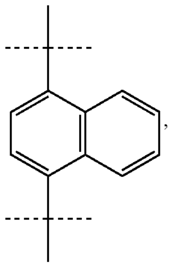,
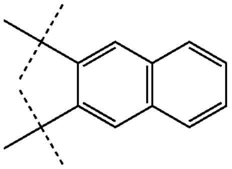,
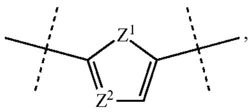,
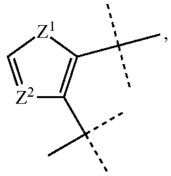,
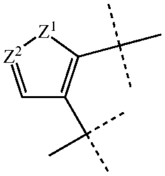 and -continued

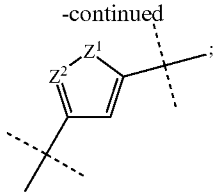;

wherein dashed lines indicate attachment to the remainder of $-L^1-$, $—Z^1—$ is selected from the group consisting of —O—, —S— and $—N(R^7)—$, and $—Z^2—$ is $—N(R^7)—$; and $—R^7$, $—R^{7a}$, $—R^{7b}$ are independently of each other selected from the group consisting of —H, $C_{1-6}$ alkyl, $C_{2-6}$ alkenyl and $C_{2-6}$ alkynyl;

wherein $-L^1-$ is optionally further substituted.

In one embodiment $-L^1-$ of formula (IX-b) is not further substituted.

In certain embodiments $=Y^1$ of formula (IX-a) and (IX-b) is =O.

In certain embodiments $—Y^2—$ of formula (IX-a) and (IX-b) is —O—.

In certain embodiments $—Y^3—$ of formula (IX-a) and (IX-b) is —O—.

In certain embodiments $—Y^4—$ of formula (IX-a) and (IX-b) is $—NR^5—$.

In certain embodiments $=Y^5$ of formula (IX-a) and (IX-b) is =O.

In certain embodiments n of formula (IX-a) and (IX-b) is 0 or 1. In certain embodiments n of formula (IX-a) and (IX-b) is 0. In certain embodiments n of formula (IX-a) and (IX-b) is 1.

In certain embodiments $—R^2$ of formula (IX-b) is selected from the group consisting of —H, methyl, ethyl, n-propyl, isopropyl, n-butyl, isobutyl, sec-butyl and tert-butyl. In certain embodiments $—R^2$ of formula (IX-b) is selected from the group consisting of —H, methyl, ethyl, n-propyl and isopropyl. In certain embodiments $—R^2$ of formula (IX-b) is selected from —H, methyl and ethyl. In certain embodiments $—R^2$ of formula (IX-b) is —H.

In certain embodiments $—R^3$ of formula (IX-a) and (IX-b) is selected from the group consisting of —H, methyl, ethyl, n-propyl, isopropyl, n-butyl, isobutyl, sec-butyl and tert-butyl. In certain embodiments $—R^3$ of formula (IX-a) and (IX-b) is selected from the group consisting of —H, methyl, ethyl, n-propyl and isopropyl. In certain embodiments $—R^3$ of formula (IX-a) and (IX-b) is selected from —H, methyl and ethyl. In certain embodiments $—R^3$ of formula (IX-a) and (IX-b) is —H.

In a preferred embodiment, each $—R^4$ of formula (IX-a) and (IX-b) is independently selected from methyl, ethyl, n-propyl, isopropyl, n-butyl, isobutyl, sec-butyl and tert-butyl. In certain embodiments $—R^4$ of formula (IX-a) and (IX-b) is selected from the group consisting of methyl, ethyl, n-propyl and isopropyl. In certain embodiments $—R^4$ of formula (IX-a) and (IX-b) is selected from methyl and ethyl.

In certain embodiments $—R^5$ of formula (IX-a) and (IX-b) is selected from the group consisting of —H, methyl, ethyl, n-propyl, isopropyl, n-butyl, isobutyl, sec-butyl and tert-butyl. In certain embodiments $—R^5$ of formula (IX-a) and (IX-b) is selected from the group consisting of —H, methyl, ethyl, n-propyl and isopropyl. In certain embodiments —$R^5$ of formula (IX-a) and (IX-b) is selected from methyl and ethyl. In certain embodiments —$R^5$ of formula (IX-a) and (IX-b) is methyl.

In certain embodiments —$R^6$ and —$R^{6a}$ of formula (IX-a) and (IX-b) are independently selected from the group consisting of —H, methyl, ethyl, n-propyl, isopropyl, n-butyl, isobutyl, sec-butyl and tert-butyl. In certain embodiments —$R^6$ and —$R^{6a}$ of formula (IX-a) and (IX-b) are independently selected from the group consisting of —H, methyl, ethyl, n-propyl and isopropyl.

In certain embodiments —$R^6$ and —$R^{6a}$ of formula (IX-a) and (IX-b) are independently selected from —H, methyl and ethyl. In certain embodiments —$R^6$ and —$R^{6a}$ of formula (IX-a) and (IX-b) are both —H.

In certain embodiments Ar of formula (IX-a) and (IX-b) is phenyl. In certain embodiments Ar of formula (IX-a) and (IX-b) is

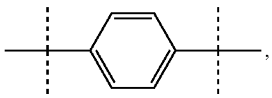

wherein the dashed lines indicate attachment to the remainder of the moiety of formula (IX-a) and (IX-b).

In certain embodiments W of formula (IX-a) and (IX-b) is $C_{1-20}$ alkyl, optionally interrupted with $C_{3-10}$ cycloalkyl, —C(O)—, —C(O)N($R^7$)—, —O—, —S— and —N($R^7$)—. In certain embodiments W of formula (IX-a) and (IX-b) is $C_{1-10}$ alkyl, optionally interrupted with $C_{3-10}$ cycloalkyl, —C(O)—, —C(O)N($R^7$)—, —O—, —S— and —N($R^7$)—. In certain embodiments W of formula (IX-a) and (IX-b) is $C_{1-6}$ alkyl, optionally interrupted with $C_{3-10}$ cycloalkyl, —C(O)—, —C(O)N($R^7$)—, —O—, —S— and —N($R^7$)—. In certain embodiments W of formula (IX-a) and (IX-b) is

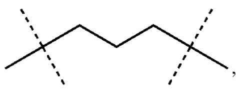

wherein the dashed lines indicate attachment to the remainder of the moiety of formula (IX-a) or (IX-b), respectively.

In certain embodiments -Nu of formula (IX-a) and (IX-b) is —N($R^7R^{7a}$).

In certain embodiments —$R^7$, —$R^{7a}$ and —$R^{7b}$ of formula (IX-a) and (IX-b) are independently of each other selected from the group consisting of —H, methyl, ethyl, n-propyl, isopropyl, n-butyl, isobutyl, sec-butyl and tert-butyl. In certain embodiments —$R^7$, —$R^{7a}$ and —R of formula (IX-a) and (IX-b) are independently of each other selected from —H, methyl, ethyl, n-propyl and isopropyl. In certain embodiments —$R^7$, —$R^{7a}$ and —$R^{7b}$ of formula (IX-a) and (IX-b) are independently of each other selected from methyl or ethyl. In certain embodiments —$R^7$, —$R^{7a}$ and —$R^{7b}$ of formula (IX-a) and (IX-b) are both methyl.

In certain embodiments -$L^1$- is of formula (IX-c)

(IX-c)

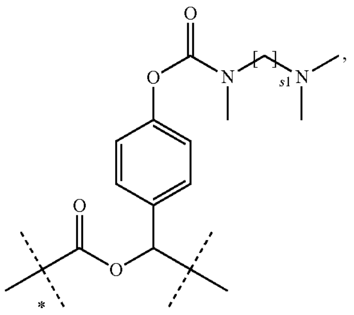

wherein the dashed line marked with the asterisk indicates attachment to a nitrogen of -D;

the unmarked dashed line indicates attachment to -$L^2$-Z; and s1 is an integer selected from the group consisting of 1, 2, 3, 4, 5, 6, 7, 8, 9 and 10.

In certain embodiments s1 of formula (IX-c) is an integer selected from the group consisting of 1, 2, 3, 4 and 5. In certain embodiments s1 of formula (IX-c) is 1. In certain embodiments s1 of formula (IX-c) is 2. In certain embodiments s1 of formula (IX-c) is 3. In certain embodiments s1 of formula (IX-c) is 4. In certain embodiments s1 of formula (IX-c) is 5.

In certain embodiments -$L^1$- is of formula (IX-d)

(IX-d)

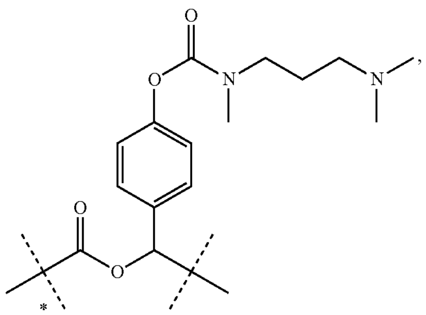

wherein the dashed line marked with the asterisk indicates attachment to a nitrogen of -D; and the unmarked dashed line indicates attachment to -$L^2$-Z.

The moiety -$L^1$- may be connected to -D through any type of linkage, provided that it is reversible. Preferably, -$L^1$- is connected to -D through a linkage selected from the group consisting of amide, ester, carbamate, acetal, aminal, imine, oxime, hydrazone, disulfide and acylguanidine. Even more preferably -$L^1$- is connected to -D through a linkage selected from the group consisting of amide, ester, carbamate and acylguanidine. It is understood that these linkages may not be reversible per se, but that reversibility may be an effect of certain groups of atoms or moieties present in -$L^1$-.

In one embodiment -$L^1$- is connected to -D through an ester linkage.

In another embodiment -$L^1$- is connected to -D through a carbamate linkage.

In another embodiment -$L^1$- is connected to -D through an acylguanidine.

In a preferred embodiment $-L^1-$ is connected to -D through an amide linkage.

In certain embodiments $-L^1-$ is connected to -D via the nitrogen of an amine functional group of a side chain of a lysine residue of -D. In certain embodiments $-L^1-$ is connected to -D via the nitrogen of an amine functional group of a side chain of a lysine residue of -D and the linkage formed between -D and $-L^1-$ is a carbamate. Embodiments for such lysine residue are as described above.

In one embodiment $-L^2-$ is a chemical bond.

In another embodiment $-L^2-$ is a spacer moiety.

In certain embodiments $-L^2-$ is selected from the group consisting of -T-, —C(O)O—, —O—, —C(O)—, —C(O)N($R^{y1}$)—, —$S(O)_2N(R^{y1})$—, —S(O)N($R^{y1}$)—, —$S(O)_2$—, —S(O)—, —N($R^{y1}$)$S(O)_2N(R^{y1a})$—, —S—, —N($R^{y1}$)—, —OC($OR^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —N($R^{y3}$)$S(O)_2N(R^{y3a})$—, —S—, —N($R^{y3}$)—, —OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —$S(O)_2N(R^{y4})$—, —S(O)N($R^{y4}$)—, —$S(O)_2$—, —S(O)—, —N($R^{y4}$)$S(O)_2N(R^{y4a})$—, —S—, —N($R^{y4}$)—, —OC($OR^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (=O), —$COOR^{y5}$, —$OR^{y5}$, —C(O)$R^{y5}$, —C(O)N($R^{y5}R^{y5a}$), —$S(O)_2N(R^{y5}R^{y5a})$, —S(O)N($R^{y5}R^{y5a}$), —$S(O)_2R^{y5}$, —S(O)$R^{y5}$, —N($R^{y5}$)$S(O)_2N(R^{y5a}R^{y5b})$, —$SR^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)$OR^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different.

In certain embodiments $-L^2-$ is selected from the group consisting of -T-, —C(O)O—, —O—, —C(O)—, —C(O)N($R^{y1}$)—, —$S(O)_2N(R^{y1})$—, —S(O)N($R^{y1}$)—, —$S(O)_2$—, —S(O)—, —N($R^{y1}$)$S(O)_2N(R^{y1a})$—, —S—, —N($R^{y1}$)—, —OC($OR^{y1}$)($R^{y1a}$)—, —N($R^{y1}$)C(O)N($R^{y1a}$)—, —OC(O)N($R^{y1}$)— $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —N($R^{y3}$)$S(O)_2N(R^{y3a})$—, —S—, —N($R^{y3}$)—, —OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —$S(O)_2N(R^{y4})$—, —S(O)N($R^{y4}$)—, —$S(O)_2$—, —S(O)—, —N($R^{y4}$)$S(O)_2N(R^{y4a})$—, —S—, —N($R^{y4}$)—, —OC($OR^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (=O), —$COOR^{y5}$, —$OR^{y5}$, —C(O)$R^{y5}$, —C(O)N($R^{y5}R^{y5a}$), —$S(O)_2N(R^{y5}R^{y5a})$, —S(O)N($R^{y5}R^{y5a}$), —$S(O)_2R^{y5}$, —S(O)$R^{y5}$, —N($R^{y5}$)$S(O)_2N(R^{y5a}R^{y5b})$, —$SR^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)$OR^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

In certain embodiments $-L^2-$ is selected from the group consisting of -T-, —C(O)O—, —O—, —C(O)—, —C(O)N($R^{y1}$)—, —$S(O)_2N(R^{y1})$—, —S(O)N($R^{y1}$)—, —$S(O)_2$—, —S(O)—, —N($R^{y1}$)$S(O)_2N(R^{y1a})$—, —S—, —N($R^{y1}$)—, —OC($OR^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —N($R^{y3}$)$S(O)_2N(R^{y3a})$—, —S—, —N($R^{y3}$)—, —OC($OR^{y3}$)($R^{y3a}$)—, —N($R^{y3}$)C(O)N($R^{y3a}$)—, and —OC(O)N($R^{y3}$)—:

—$R^1$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen, and $C_{1-6}$ alkyl; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

In certain embodiments -$L^2$- is a $C_{1-20}$ alkyl chain, which is optionally interrupted by one or more groups independently selected from —O—, -T- and —C(O)N($R^1$)—; and which $C_{1-20}$ alkyl chain is optionally substituted with one or more groups independently selected from —OH, -T and —C(O)N($R^{y6}R^{y6a}$); wherein —$R^{y1}$, —$R^{y6}$, —$R^{y6a}$ are independently selected from the group consisting of H and $C_{1-4}$ alkyl and wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

In certain embodiments -$L^2$- has a molecular weight in the range of from 14 g/mol to 750 g/mol.

In certain embodiments -$L^2$- comprises a moiety selected from the group consisting of

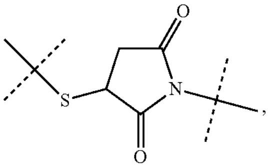
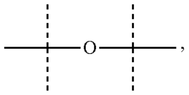
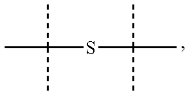
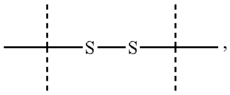
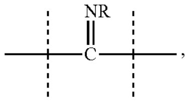
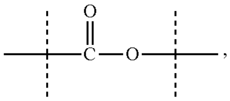
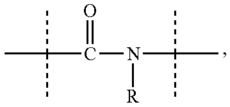
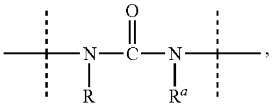
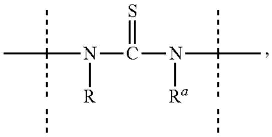
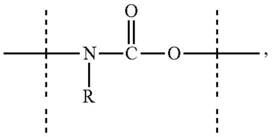
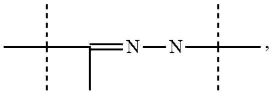
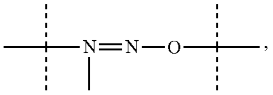
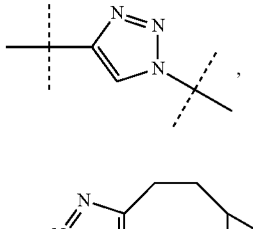
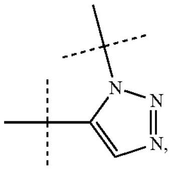
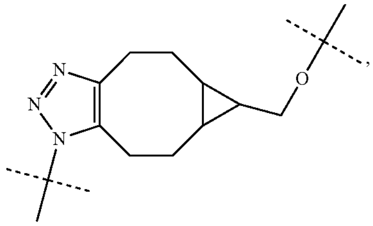

-continued

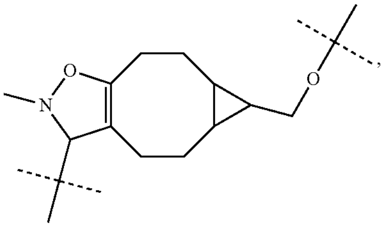
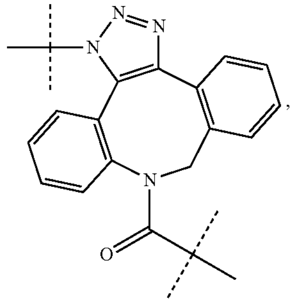
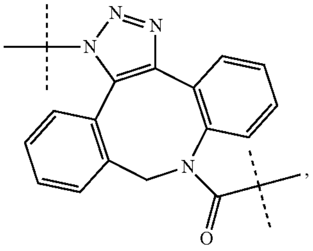
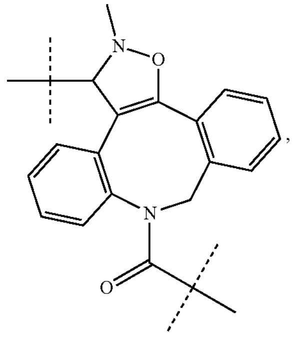
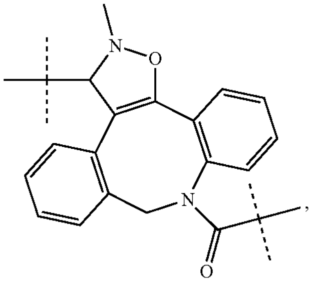
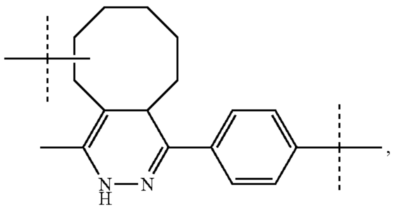

-continued

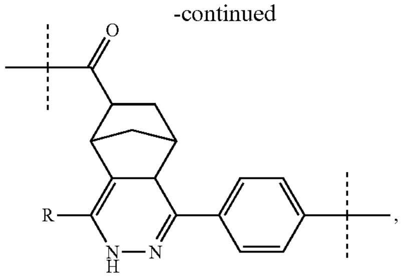

, and

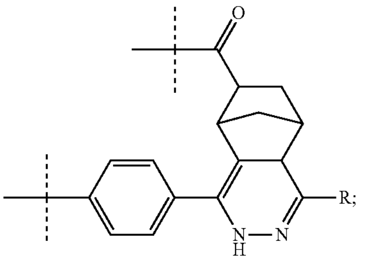

wherein dashed lines indicate attachment to $-L^1-$, the remainder of $-L^2-$ or to —Z, respectively; and —R and —$R^a$ are independently of each other selected from the group consisting of —H, methyl, ethyl, propyl, butyl, pentyl and hexyl.

In certain embodiments $-L^2-$ is of formula (IX-e)

(IX-e)

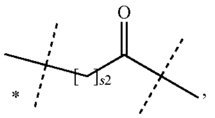

wherein the dashed line marked with the asterisk indicates attachment to $-L^1-$;

the unmarked dashed line indicates attachment to —Z; and s2 is an integer selected from the group consisting of 0, 1, 2, 3, 4, 5, 6, 7, 8, 9, 10, 11, 12, 13, 14, 15, 16, 17, 18, 19 and 20.

In certain embodiments s2 of formula (IX-e) is an integer selected from the group consisting of 1, 2, 3, 4, 5, 6, 7, 8, 9, 10, 11 and 12. In certain embodiments s2 of formula (IX-e) is an integer selected from the group consisting of 1, 2, 3, 4, 5, 6, 7 and 8. In certain embodiments s2 of formula (IX-e) is 1. In certain embodiments s2 of formula (IX-e) is 2. In certain embodiments s2 of formula (IX-e) is 3. In certain embodiments s2 of formula (IX-e) is 4. In certain embodiments s2 of formula (IX-e) is 5. In certain embodiments s2 of formula (IX-e) is 6. In certain embodiments s2 of formula (IX-e) is 7. In certain embodiments s2 of formula (IX-e) is 8.

In certain embodiments the moiety $-L^1-L^2-$ is of formula (IX-f)

(IX-f)

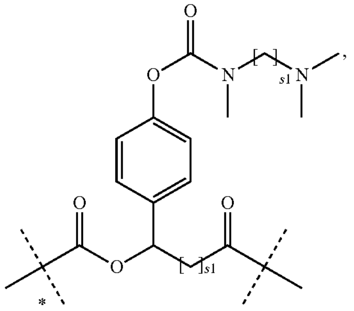

wherein the dashed line marked with the asterisk indicates attachment to a nitrogen of -D;

the unmarked dashed line indicates attachment to —Z;

s1 is an integer selected from the group consisting of 1, 2, 3, 4, 5, 6, 7, 8, 9 and 10; and s2 is an integer selected from the group consisting of 0, 1, 2, 3, 4, 5, 6, 7, 8, 9, 10, 11, 12, 13, 14, 15, 16, 17, 18, 19 and 20.

Accordingly, the linkage between the moiety $-L^1-$ and -D formed in the compound of formula (IX-f) is a carbamate.

In certain embodiments s1 of formula (IX-f) is an integer selected from the group consisting of 1, 2, 3, 4 and 5. In certain embodiments s1 of formula (IX-f) is 1. In certain embodiments s1 of formula (IX-f) is 2. In certain embodiments s1 of formula (IX-f) is 3. In certain embodiments s1 of formula (IX-f) is 4. In certain embodiments s1 of formula (IX-f) is 5.

In certain embodiments s2 of formula (IX-f) is an integer selected from the group consisting of 1, 2, 3, 4, 5, 6, 7, 8, 9, 10, 11 and 12. In certain embodiments s2 of formula (IX-f) is an integer selected from the group consisting of 1, 2, 3, 4, 5, 6, 7 and 8. In certain embodiments s2 of formula (IX-f) is 1. In certain embodiments s2 of formula (IX-f) is 2. In certain embodiments s2 of formula (IX-f) is 3. In certain embodiments s2 of formula (IX-e) is 4. In certain embodiments s2 of formula (IX-f) is 5. In certain embodiments s2 of formula (IX-e) is 6. In certain embodiments s2 of formula (IX-f) is 7. In certain embodiments s2 of formula (IX-f) is 8.

In certain embodiments s1 of formula (IX-f) is 3 and s2 of formula (IX-f) is 3.

In one embodiment the IL-2 conjugate of the present invention is of formula (Ia). In one embodiment x is 1. In another embodiment x is 2. In another embodiment x is 3. In another embodiment x is 4.

In another embodiment the IL-2 conjugate of the present invention is of formula (Ib). In one embodiment y is 2. In another embodiment y is 3. In another embodiment y is 4.

Another aspect of the present invention is a pharmaceutical composition comprising at least one IL-2 conjugate of the present invention and at least one excipient.

Preferably, the pharmaceutical composition comprising at least one IL-2 conjugate of the present invention has a pH ranging from and including pH 3 to pH 8.

In one embodiment the pharmaceutical composition comprising at least one IL-2 conjugate of the present invention and at least one excipient is a liquid formulation.

In another embodiment the pharmaceutical composition comprising at least one IL-2 conjugate of the present invention and at least one excipient is a dry formulation.

Such liquid or dry pharmaceutical composition comprises at least one excipient. Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. Preferably, the at least one excipient comprised in the pharmaceutical composition of the present invention is selected from the group consisting of (i) Buffering agents: physiologically tolerated buffers to maintain pH in a desired range, such as sodium phosphate, bicarbonate, succinate, histidine, citrate and acetate, sulphate, nitrate, chloride, pyruvate; antacids such as $Mg(OH)_2$ or $ZnCO_3$ may be also used;

(ii) Isotonicity modifiers: to minimize pain that can result from cell damage due to osmotic pressure differences at the injection depot; glycerin and sodium chloride are examples; effective concentrations can be determined by osmometry using an assumed osmolality of 285-315 mOsmol/kg for serum;

(iii) Preservatives and/or antimicrobials: multidose parenteral formulations require the addition of preservatives at a sufficient concentration to minimize risk of patients becoming infected upon injection and corresponding regulatory requirements have been established; typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride;

(iv) Stabilizers: Stabilisation is achieved by strengthening of the protein-stabilising forces, by destabilisation of the denatured state, or by direct binding of excipients to the protein; stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives; in addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the formulation's container; e.g., poloxamer (Pluronic F-68), PEG dodecyl ether (Brij 35), polysorbate 20 and 80, dextran, polyethylene glycol, PEG-polyhistidine, BSA and HSA and gelatins; chosen concentration and type of excipient depends on the effect to be avoided but typically a monolayer of surfactant is formed at the interface just above the CMC value;

(vi) Oxidation protection agents: antioxidants such as ascorbic acid, ectoine, methionine, glutathione, monothioglycerol, morin, polyethylenimine (PEI), propyl gallate, and vitamin E; chelating agents such as citric acid, EDTA, hexaphosphate, and thioglycolic acid may also be used;

(vii) Viscosifiers or viscosity enhancers: retard settling of the particles in the vial and syringe and are used in order to facilitate mixing and resuspension of the particles and to make the suspension easier to inject (i.e., low force on the syringe plunger); suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly (glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly(acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone; such block copolymers as well as the abovementioned poloxamers may exhibit reverse thermal gelation behavior (fluid state at room temperature to facilitate administration and gel state above sol-gel transition temperature at body temperature after injection);

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue; a spreading agent such as but not limited to hyaluronidase temporarily decreases the viscosity of the extracellular matrix and promotes diffusion of injected drugs; and (ix) Other auxiliary agents: such as wetting agents, viscosity modifiers, antibiotics, hyaluronidase; acids and bases such as hydrochloric acid and sodium hydroxide are auxiliary agents necessary for pH adjustment during manufacture.

Another aspect of the present invention is the IL-2 conjugate or a pharmaceutically acceptable salt thereof or a pharmaceutical composition comprising at least one IL-2 conjugate of the present invention for use as a medicament.

Another aspect of the present invention is the IL-2 conjugate or a pharmaceutically acceptable salt thereof or the pharmaceutical composition comprising at least one IL-2 conjugate of the present invention for use in the treatment of a disease which can be treated with IL-2.

Preferably, said disease is cancer. Even more preferably said disease is selected from the group consisting of sarcoma, chordoma, colon cancer, rectal cancer, colorectal cancer, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, gastric cancer, non-small cell lung cancer, small cell lung cancer, bladder cancer, renal cell carcinoma, urothelial cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, non-Hodgkin's lymphoma, cutaneous T-cell lymphoma, acute myeloid leukemia and leukemias. Even more preferred is a disease selected from the group consisting of non-small cell lung cancer, small cell lung cancer, melanoma, renal cell carcinoma, urothelial cancer, breast cancer, colorectal cancer, gastric cancer, and sarcoma.

Preferred types of sarcomas include fibrosarcoma, myxosarcoma, leiomyosarcoma, liposarcoma, chondrosarcoma, osteogenic sarcoma, angiosarcoma, endotheliosarcoma, gastrointestinal stromal tumor, lymphangiosarcoma, lymphangioendotheliosarcoma, synovioma, mesothelioma, Ewing's tumor, leiomyosarcoma, and rhabdomyosarcoma.

In one embodiment, the IL-2 conjugate or a pharmaceutically acceptable salt thereof or the pharmaceutical composition comprising at least one IL-2 conjugate of the present invention for use in the treatment of a disease which can be treated with IL-2 is administered to the patient prior to, simultaneously with, or after administration of one or more further drugs, which one or more further drugs are preferably selected from the group consisting of PD-1 inhibitors; PD-L1 inhibitors; CTLA-4 inhibitors; cancer vaccines, such as tumor cell vaccines, antigen vaccines, dendritic cell vaccines, vector-based vaccines; Toll-like Receptor Agonist (TLR), including agonists targeting TLR2, TLR3, TLR2/4, TLR4, TLR5, TLR7/8 and TLR9; and agents which agonize immune activating receptors such as 41BB (CD137), OX40, ICOS, CD40, CD28, NKG2D, NKp30, NKp44, NKp46, LFA1, CD16, CD64, CD32A and CD3. In one embodiment, the IL-2 conjugate or a pharmaceutically acceptable salt thereof or the pharmaceutical composition comprising at least one IL-2 conjugate of the present invention for use in the treatment of a disease which can be treated with IL-2 is administered to the patient prior to, simultaneously with, or after administration of one or more further drugs, which one or more further drugs are preferably selected from the group consisting of PD-1 inhibitors; PD-L1 inhibitors; CTLA-4 inhibitors; cancer vaccines, such as tumor cell vaccines, antigen vaccines, dendritic cell vaccines, vector-based vaccines; and Toll-like Receptor Agonist (TLR), including agonists targeting TLR2, TLR3, TLR2/4, TLR4, TLR5, TLR7/8 and TLR9. Such administration of the IL-2 conjugate or a pharmaceutically acceptable salt thereof or the pharmaceutical composition comprising at least one IL-2 conjugate of the present invention with one or more further drugs may either be a single event or may be repeated multiple times.

In one embodiment the PD-1 inhibitor is pembrolizumab. In another embodiment the PD-1 inhibitor is nivolumab.

In one embodiment the PD-L1 inhibitor is atezolizumab. In another embodiment the PD-L1 inhibitor is avelumab. In another embodiment the PD-L1 inhibitor is durvalumab.

In one embodiment the CTLA-4 inhibitor is ipilimumab. In another embodiment the CTLA-4 inhibitor is tremelimumab.

In another embodiment the IL-2 conjugate or a pharmaceutically acceptable salt thereof or the pharmaceutical composition comprising at least one IL-2 conjugate of the present invention is administered to the patient prior to, simultaneously with, or after CAR-T therapy. Such administration of the IL-2 conjugate or a pharmaceutically acceptable salt thereof or the pharmaceutical composition comprising at least one IL-2 conjugate of the present invention in combination with CAR-T therapy may either be a single event or may be repeated multiple times.

Preferably, the IL-2 conjugate, a pharmaceutically acceptable salt thereof or the pharmaceutical composition comprising at least one IL-2 conjugate of the present invention for use in the treatment is administered to a mammalian patient, preferably to a human patient.

Another aspect of the present invention is the use of the IL-2 conjugate or a pharmaceutically acceptable salt thereof or the pharmaceutical composition comprising at least one IL-2 conjugate of the present invention for the manufacture of a medicament for treating a disease which can be treated with IL-2.

Preferably, said disease is cancer. Even more preferably said disease is selected from the group consisting of sarcoma, chordoma, colon cancer, rectal cancer, colorectal cancer, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, gastric cancer, non-small cell lung cancer, small cell lung cancer, bladder cancer, renal cell carcinoma, urothelial cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, non-Hodgkin's lymphoma, cutaneous T-cell lymphoma, acute myeloid leukemia and leukemias. Even more preferred is a disease selected from the group consisting of non-small cell lung cancer, small cell lung cancer, melanoma, renal cell carcinoma, urothelial cancer, breast cancer, colorectal cancer, gastric cancer, and sarcoma.

Preferred types of sarcomas include fibrosarcoma, myxosarcoma, leiomyosarcoma, liposarcoma, chondrosarcoma, osteogenic sarcoma, angiosarcoma, endotheliosarcoma, gastrointestinal stromal tumor, lymphangiosarcoma, lymphangioendotheliosarcoma, synovioma, mesothelioma, Ewing's tumor, leiomyosarcoma, and rhabdomyosarcoma.

In one embodiment, the medicament is administered to the patient prior to, simultaneously with, or after administration of one or more further drugs, which one or more further drugs are preferably selected from the group consisting of PD-1 inhibitors; PD-L1 inhibitors; CTLA-4 inhibitors; cancer vaccines, such as tumor cell vaccines, antigen vaccines, dendritic cell vaccines, vector-based vaccines; Toll-like Receptor Agonist (TLR), including agonists targeting TLR2, TLR3, TLR2/4, TLR4, TLR5, TLR7/8 and TLR9; and agents which agonize immune activating receptors such as 41BB (CD137), OX40, ICOS, CD40, CD28, NKG2D, NKp30, NKp44, NKp46, LFA1, CD16, CD64, CD32A and CD3. Such administration of the medicament with one or more further drugs may either be a single event or may be repeated multiple times. In one embodiment, the medicament is administered to the patient prior to, simultaneously with, or after administration of one or more further drugs, which one or more further drugs are preferably selected from the group consisting of PD-1 inhibitors; PD-L1 inhibitors; CTLA-4 inhibitors; cancer vaccines, such as tumor cell vaccines, antigen vaccines, dendritic cell vaccines, vector-based vaccines; and Toll-like Receptor Agonist (TLR), including agonists targeting TLR2, TLR3, TLR2/4, TLR4, TLR5, TLR7/8 and TLR9. Such administration of the medicament with one or more further drugs may either be a single event or may be repeated multiple times.

In one embodiment the PD-1 inhibitor is pembrolizumab. In another embodiment the PD-1 inhibitor is nivolumab.

In one embodiment the PD-L1 inhibitor is atezolizumab. In another embodiment the PD-L1 inhibitor is avelumab. In another embodiment the PD-L1 inhibitor is durvalumab.

In one embodiment the CTLA-4 inhibitor is ipilimumab. In another embodiment the CTLA-4 inhibitor is tremelimumab.

In another embodiment the medicament is administered to the patient prior to, simultaneously with, or after CAR-T therapy. Such administration of the medicament in combination with CAR-T therapy may either be a single event or may be repeated multiple times.

Preferably, the medicament is administered to a mammalian patient, more preferably to a human patient.

A further aspect of the present invention is a method of treating, controlling, delaying or preventing in a mammalian patient, preferably a human patient, in need of the treatment of one or more diseases which can be treated with IL-2, comprising the step of administering to said patient in need thereof a therapeutically effective amount of the IL-2 conjugate or a pharmaceutically acceptable salt thereof or a pharmaceutical composition comprising the IL-2 conjugate of the present invention.

Preferably, the one or more diseases that can be treated with IL-2 is cancer. Even more preferably said disease is selected from the group consisting of sarcoma, chordoma, colon cancer, rectal cancer, colorectal cancer, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, gastric cancer, non-small cell lung cancer, small cell lung cancer, bladder cancer, renal cell carcinoma, urothelial cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, non-Hodgkin's lymphoma, cutaneous T-cell lymphoma, acute myeloid leukemia and leukemias. Even more preferred is a disease selected from the group consisting of non-small cell lung cancer, small cell lung cancer, melanoma, renal cell carcinoma, urothelial cancer, breast cancer, colorectal cancer, gastric cancer, and sarcoma.

Preferred types of sarcomas include fibrosarcoma, myxosarcoma, leiomyosarcoma, liposarcoma, chondrosarcoma, osteogenic sarcoma, angiosarcoma, endotheliosarcoma, gastrointestinal stromal tumor, lymphangiosarcoma, lymphangioendotheliosarcoma, synovioma, mesothelioma, Ewing's tumor, leiomyosarcoma, and rhabdomyosarcoma.

In one embodiment the IL-2 conjugate or a pharmaceutically acceptable salt thereof or a pharmaceutical composition comprising the IL-2 conjugate of the present invention is administered to the patient prior to, simultaneously with, or after administration of one or more further drugs, which one or more further drugs are preferably selected from the group consisting of PD-1 inhibitors; PD-L1 inhibitors; CTLA-4 inhibitors; cancer vaccines, such as tumor cell vaccines, antigen vaccines, dendritic cell vaccines, vector-based vaccines; Toll-like Receptor Agonist (TLR), including agonists targeting TLR2, TLR3, TLR2/4, TLR4, TLR5, TLR7/8 and TLR9; and agents which agonize immune activating receptors such as 41BB (CD137), OX40, ICOS, CD40, CD28, NKG2D, NKp30, NKp44, NKp46, LFA1, CD16, CD64, CD32A and CD3. Such administration of the IL-2 conjugate or a pharmaceutically acceptable salt thereof or the pharmaceutical composition comprising at least one IL-2 conjugate of the present invention with one or more further drugs may either be a single event or may be repeated multiple times. In one embodiment the IL-2 conjugate or a pharmaceutically acceptable salt thereof or a pharmaceutical composition comprising the IL-2 conjugate of the present invention is administered to the patient prior to, simultaneously with, or after administration of one or more further drugs, which one or more further drugs are preferably selected from the group consisting of PD-1 inhibitors; PD-L1 inhibitors; CTLA-4 inhibitors; cancer vaccines, such as tumor cell vaccines, antigen vaccines, dendritic cell vaccines, vector-based vaccines; and Toll-like Receptor Agonist (TLR), including agonists targeting TLR2, TLR3, TLR2/4, TLR4, TLR5, TLR7/8 and TLR9. Such administration of the IL-2 conjugate or a pharmaceutically acceptable salt thereof or the pharmaceutical composition comprising at least one IL-2 conjugate of the present invention with one or more further drugs may either be a single event or may be repeated multiple times.

In one embodiment the PD-1 inhibitor is pembrolizumab. In another embodiment the PD-1 inhibitor is nivolumab.

In one embodiment the PD-L1 inhibitor is atezolizumab. In another embodiment the PD-L1 inhibitor is avelumab. In another embodiment the PD-L1 inhibitor is durvalumab.

In one embodiment the CTLA-4 inhibitor is ipilimumab. In another embodiment the CTLA-4 inhibitor is tremelimumab.

In another embodiment the IL-2 conjugate or a pharmaceutically acceptable salt thereof or the pharmaceutical composition comprising at least one IL-2 conjugate of the present invention is administered to the patient prior to, simultaneously with, or after CAR-T therapy. Such administration of the IL-2 conjugate or a pharmaceutically acceptable salt thereof or the pharmaceutical composition comprising at least one IL-2 conjugate of the present invention in combination with CAR-T therapy may either be a single event or may be repeated multiple times.

An additional aspect of the present invention is a method of administering the IL-2 conjugate, a pharmaceutically acceptable salt thereof or the pharmaceutical composition of the present invention, wherein the method comprises the step of administering the IL-2 conjugate, a pharmaceutically acceptable salt thereof or the pharmaceutical composition of the present invention via topical, enteral or parenteral administration and by methods of external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection and infusion, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation, preferably via subcutaneous injection.

In one embodiment, the present invention relates to an IL-2 conjugate or pharmaceutically acceptable salt thereof or a pharmaceutical composition of the present invention, for use in the treatment of one or more diseases that can be treated with IL-2 via subcutaneous injection. In another embodiment, the present invention relates to an IL-2 conjugate or pharmaceutically acceptable salt thereof or a pharmaceutical composition of the present invention, for use in the treatment of one or more diseases that can be treated with IL-2 via subcutaneous injection.

Materials 0.7 kDa PEG maleimide (MeO-dPEG(12)-mal, Maleimidyl-N-(2,5,8,11,14,17,20,23,26,29,32,35-dodecaoxa heptatriacontan-37-yl)propanamide, CAS 724722-89-8) was acquired from Iris Biotech GmbH, Marktredwitz, Germany. 2 kDa PEG-maleimide (Sunbright ME-020-MA, CAS 883993-35-9), 5 kDa PEG-maleimide (Sunbright ME-050MA, CAS 883993-35-9), 10 kDa PEG-maleimide (Sunbright ME-100MA, CAS 883993-35-9) and 20 kDa PEG-maleimide (Sunbright ME-200MA0B, CAS 883993-35-9) were acquired from NOF Europe N.V., Grobbendonk, Belgium.

kDa PEG amine (Sunbright ME-100EA, CAS 80506-64-5) can be acquired from NOF Europe N.V., Grobbendonk, Belgium.

Recombinant human IL-2 (Aldesleukin, catalog #AF-200-02) was acquired from Peprotech, Rocky Hill, NJ, USA.

Microbial transglutaminase (catalog #T001) and MTG blocker (catalog #C102) were acquired from Zedira GmbH, Darmstadt, Germany.

10 kDa Mal-PEG-$NH_2$ (catalog #PHB-943) may for example be acquired from Creative PEGWorks, Chapell Hill, NC, USA.

METHODS

Example 1: Preparation of IL-2 Variants

IL-2 variants (muteins) were custom made and sourced from an external supplier where expression of the proteins was performed from *E. coli* followed by standard purification strategies known to the one skilled in the art. The following proteins were prepared

```
1a-SEQ ID NO: 3:
PTSSSTKKTQ LQLEHLLLDL QMILNGINNY KNPKLTCMLT

FKFYMPKKAT ELKHLQCLEE ELKPLEEVLN LAQSKNFHLR

PRDLISNINV IVLELKGSET TFMCEYADET ATIVEFLNRW

ITFSQSIIST LT

1b-SEQ ID NO: 4:
PTSSSTKKTQ LQLEHLLLDL QMILNGINNY KNPKLTRMLT

CKFYMPKKAT ELKHLQCLEE ELKPLEEVLN LAQSKNFHLR

PRDLISNINV IVLELKGSET TFMCEYADET ATIVEFLNRW

ITFSQSIIST LT

1c-SEQ ID NO: 5:
PTSSSTKKTQ LQLEHLLLDL QMILNGINNY KNPKLTRMLT

FKFCMPKKAT ELKHLQCLEE ELKPLEEVLN LAQSKNFHLR

PRDLISNINV IVLELKGSET TFMCEYADET ATIVEFLNRW

ITFSQSIIST LT
```

-continued

```
1d-SEQ ID NO: 6:
PTSSSTKKTQ LQLEHLLLDL QMILNGINNY KNPKLTRMLT

FKFYMPKKAT ELKHLQCLEE CLKPLEEVLN LAQSKNFHLR

PRDLISNINV IVLELKGSET TFMCEYADET ATIVEFLNRW

ITFSQSIIST LT
```

Example 2: Preparation of 0.7 kDa PEG-IL-2 Mutein Conjugate 2

Approx. 2 mL IL-2 mutein 1a at 0.2 mg/mL formulated in 50 mM acetic acid, pH 3 were concentrated via centrifugal filters to a final volume of 0.47 mL with a concentration of 0.85 mg/mL, as determined by UV (A280). Conjugation was performed at approx. pH 7.5 as follows. 0.385 mg 1a (0.455 mL at 0.85 mg/mL) in 50 mM acetic acid, pH 3 were mixed with 0.36 vol. eq. (164 μL) of 0.5 M sodium phosphate, pH 8, 16 μL of 37 mM acetic acid, 132 mM sodium phosphate, pH 7, and 3 mol eq. (5 μL) of 15.1 mM maleimidyl-N-(2,5,8,11,14,17,20,23,26,29,32,35-dodecaoxaheptatriacontan-37-yl)propanamide in water. The solution was shaken carefully and allowed to stand for 15 min at ambient temperature. Quantitative conversion of 1a to the respective monoconjugate was confirmed via MS. The conjugate was isolated from the reaction mixture via size exclusion chromatography (SEC) using a GE Healthcare Superdex 200 Increase 10/300 GL (24 mL volume) column connected to an Äkta system with 10 mM HEPES, 150 mM sodium chloride, 0.05% Tween 20, pH 7.4 as mobile phase and a flow rate of 0.75 mL/min. One fraction predominantly containing the conjugate was concentrated using centrifugal filters to finally give 2 as 0.45 mL of protein solution with a protein content of 0.22 mg/mL and an approximate purity of 79%, as determined by SEC.

Example 3: Preparation of 2 kDa PEG-IL-2 Mutein Conjugate 3

Approx. 2 mL of IL-2 mutein 1a at 0.2 mg/mL formulated in 50 mM acetic acid, pH 3 were concentrated via centrifugal filters to a final volume of 0.34 mL with a concentration of 1.16 mg/mL, as determined by A280. Conjugation was performed at approx. pH 7 as follows. 0.38 mg 1a (0.33 mL at 1.16 mg/mL) in 50 mM acetic acid, pH 3 were mixed with 0.36 vol. eq. (118 μL) of 0.5 M sodium phosphate, pH 8, and 20 mol eq. (20 μL) of 24.8 mM 2 kDa PEG-Mal in water. The solution was shaken carefully and incubated for 15 min at ambient temperature. 0.82 mL of a thiol functionalized hydrogel suspension as described in WO2014056923 example 29, page 159 with a hydrogel content of 21.8 mg/mL and a thiol content of 3 μmol/mL (corresponding to 5 mol eq. of thiol with respect to the 2 kDa PEG maleimide) were transferred into a 2 mL PP reactor equipped with PE frit. The reaction mixture was transferred into the reaction vessel and incubated for 30 min at ambient temperature with gentle agitation to enable binding of the excess PEG-maleimide to the hydrogel. The protein containing solution was expelled and the protein conjugate was isolated via size exclusion chromatography (SEC) from the conjugation mixture using a GE Healthcare Superdex 75 Increase 10/300 GL (24 mL volume) column connected to an Äkta system with 10 mM HEPES, 150 mM sodium chloride, 0.05% Tween 20, pH 7.4 as mobile phase at a flow rate of 0.75 mL/min. The conjugate containing fraction was concentrated using centrifugal filters to give 0.37 mL of 2 kDa PEG IL-2 mutein conjugate 3 at a protein concentration of 0.27 mg/mL with a purity of 78% according to SEC.

Example 4: Preparation of 5 kDa PEG-IL-2 Mutein Conjugate 4

Approx. 2 mL IL-2 mutein 1a at 0.2 mg/mL formulated in 50 mM acetic acid, pH 3 were concentrated via centrifugal filters to give a final volume of 0.36 mL with a concentration of 1.01 mg/mL, as determined by A280. Conjugation was performed at approx. pH 7.5 as follows. 0.35 mg of the protein (0.35 mL at 1.01 mg/mL) in 50 mM acetic acid, pH 3 were mixed with 0.36 vol. eq. (125 μL) of 0.5 M sodium phosphate, pH 8, and 3 mol eq. (9.8 μL, activity-corrected) of 7.49 mM 5 kDa PEG-maleimide in water. The solution was shaken carefully and incubated for 15 min at ambient temperature. To quench excess PEG-maleimide, 6 mol eq. with regard to 1a (10 μL) of 13.8 mM L-cysteine in water were added to the conjugation mixture. The solution was shaken carefully and incubated for 2.5 h at ambient temperature. The conjugate was isolated by size exclusion chromatography (SEC) from the conjugation mixture using a GE Healthcare Superdex 75 Increase 10/300 GL (24 mL volume) column connected to an Äkta system with 10 mM HEPES, 150 mM sodium chloride, 0.05% Tween 20, pH 7.4 as mobile phase and a flow rate of 0.75 mL/min. Fractions predominantly containing the conjugate were pooled and concentrated using centrifugal filters to give 0.42 mL of 5 kDa PEG IL-2 mutein conjugate 4 with a protein concentration of 0.30 mg/mL. Analysis of the isolated conjugate was performed via SEC and RP-HPLC. Quantitative depletion of impurities could not be achieved by the purification step, as shown by RP-HPLC. An approximate purity of conjugate 4 was determined as 68% according to SEC analysis at 215 nm.

Example 5: Preparation of 10 kDa PEG-IL-2 Mutein Conjugate 5

Approx. 2 mL IL-2 mutein 1a at 0.2 mg/mL formulated in 50 mM acetic acid, pH 3 were concentrated via centrifugal filters to give a final volume of 0.35 mL with a concentration of 1.03 mg/mL, as determined by A280. Conjugation was performed at approx. pH 7.5 as follows. 0.34 mg of the protein (0.33 mL at 1.03 mg/mL) in 50 mM acetic acid, pH 3 were mixed with 0.36 vol. eq. (120 μL) of 0.5 M sodium phosphate, pH 8, and 3 mol eq. (5 μL) of 13.54 mM 10 kDa PEG-maleimide in water. The solution was shaken carefully and incubated for 15 min at ambient temperature. The conjugate was isolated by size exclusion chromatography (SEC) from the conjugation mixture using a GE Healthcare Superdex 200 Increase 10/300 GL (24 mL volume) column connected to an Äkta system with 10 mM HEPES, 150 mM sodium chloride, 0.05% Tween 20, pH 7.4 as mobile phase and a flow rate of 0.75 mL/min. Fractions predominantly containing the conjugate were pooled and concentrated using centrifugal filters to give 0.55 mL of 10 kDa PEG IL-2 mutein conjugate 5 with a protein concentration of 0.22 mg/mL. Analysis of the isolated conjugate was performed via SEC and RP-HPLC. Quantitative depletion of impurities could not be achieved by the purification step. An approximate purity of conjugate 5 was determined as 57% according to SEC analysis at 215 nm with excess PEG-Mal being the main impurity.

Example 6: Preparation of 20 kDa PEG-IL-2 Mutein Conjugate 6

Approx. 2 mL IL-2 mutein 1a at 0.2 mg/mL formulated in 50 mM acetic acid, pH 3 were concentrated via centrifugal filters to give a final volume of 0.33 mL with a concentration of 1.11 mg/mL, as determined by A280. Conjugation was performed at approx. pH 7.5 as follows. 0.35 mg of the protein (0.32 mL at 1.11 mg/mL) in 50 mM acetic acid, pH 3 were mixed with 0.36 vol. eq. (115 μL) of 0.5 M sodium phosphate, pH 8, 6 μL of 37 mM acetic acid, 132 mM sodium phosphate, pH 7, and 3 mol eq. (10 μL) of 6.96 mM 20 kDa PEG-maleimide in water. The solution was shaken carefully and incubated for 15 min at ambient temperature. The conjugate was isolated by size exclusion chromatography (SEC) from the conjugation mixture using a GE Healthcare Superdex 200 Increase 10/300 GL (24 mL volume) connected to an Äkta system with 10 mM HEPES, 150 mM sodium chloride, 0.05% Tween 20, pH 7.4 as mobile phase and a flow rate of 0.75 mL/min. Fractions predominantly containing the conjugate were pooled and concentrated using centrifugal filters to give 0.67 mL of 20 kDa PEG IL-2 mutein conjugate 6 with a protein concentration of 0.18 mg/mL. Analysis of the isolated conjugate was performed via SEC and RP-HPLC. Quantitative depletion of impurities could not be achieved by the purification step. An approximate purity of conjugate 6 was determined as 44% according to RP-HPLC analysis at 215 nm with excess PEG-Mal being the main impurity.

Example 7: Preparation of 5 kDa PEG-IL-2 Mutein Conjugate 7

1.1 mL of IL-2 mutein 1c at 0.66 mg/mL formulated in 50 mM acetic acid, pH 3 were mixed with 0.15 vol. eq. (165 μL) of 0.5 M sodium phosphate, pH 8 and 141 μL of 0.6M hydroxylamine hydrochloride, 0.5 M sodium phosphate, pH 6.4. The resulting reaction mixture was incubated at 25° C. overnight. The solution was concentrated using centrifugal filters to give a final volume of 0.67 mL with a concentration of 0.99 mg/mL as determined by A280. Conjugation was performed as follows. 0.65 mg of the protein (0.66 mL at 0.99 mg/mL) in 58 mM sodium phosphate, approx. 57 mM hydroxylamine hydrochloride, 39 mM acetic acid, pH 6.5 were mixed with 6 mol eq. (320 μL) of 81 mM 5 kDa PEG-maleimide in water. The resulting reaction mixture was incubated at ambient temperature for 2.25 hours. Subsequently, buffer exchange was performed using a centrifugal filter to 37 mM acetic acid, 132 mM phosphate, pH 7 to give a final volume of 0.75 mL. 1.5 mol eq. (80 μL) of 81 mM 5 kDa PEG-maleimide in water were added to the reaction solution followed by addition of 3 mol eq. (160 μL) of 81 mM 5 kDa PEG-maleimide in water after 3.5 hours. The resulting reaction mixture was allowed to incubate at ambient temperature overnight. The conjugate was isolated via size exclusion chromatography (SEC) from the conjugation mixture using a GE Healthcare Superdex 75 Increase 10/300 GL (24 mL volume) column connected to an Äkta system with 10 mM HEPES, 150 mM sodium chloride, 0.05% Tween, pH 7.4 as mobile phase at a flow rate of 0.75 mL/min. The collected fraction containing the conjugate was concentrated using centrifugal filters to give 0.45 mL of 5 kDa PEG IL-2 mutein 7 at 0.25 mg/mL. Analysis of the isolated conjugate was performed by SEC and RP-HPLC. Depletion of impurities could not be achieved quantitatively by the purification step, leading to their presence in the conjugate sample resulting in an approximate purity of conjugate 7 of 60% according to SEC.

Example 8: Preparation of 10 kDa PEG-IL-2 Mutein Conjugate 8

1.1 mL of IL-2 mutein 1c at 0.66 mg/mL formulated in 50 mM acetic acid, pH 3 were mixed with 0.15 vol. eq. (165 μL)

of 0.5 M sodium phosphate, pH 8 and 141 µL of 0.5 M hydroxylamine hydrochloride, 0.05 M sodium phosphate, pH 7. The resulting reaction mixture was incubated at 25° C. overnight. The solution was concentrated using centrifugal filters to give a final volume of 0.48 mL with a concentration of 1.42 mg/mL as determined by A280. Conjugation was performed as follows. 0.678 mg of the protein (0.48 mL at 1.42 mg/mL) in 64 mM sodium phosphate, 50 mM hydroxylamine hydrochloride, 39 mM acetic acid, pH 6.5-7.0 were mixed with 3 mol eq. (18 µL) of 7.42 mM 10 kDa PEG10-maleimide in water. The resulting reaction mixture was shaken carefully and incubated for 15 min at ambient temperature. Additional 3 mol eq. (17.9 µL) of 7.42 mM PEG-maleimide in water were added to the conjugation mixture followed by incubation for 15 min at ambient temperature. The conjugate was isolated by size exclusion chromatography (SEC) from the conjugation mixture using a GE Healthcare Superdex 200 Increase 10/300 GL (24 mL volume) column connected to an Äkta system with 10 mM HEPES, 150 mM sodium chloride, 0.05% Tween 20, pH 7.4 as mobile phase and a flow rate of 0.75 mL/min. The collected fractions were analyzed by RP-HPLC and conjugate containing fractions were pooled and concentrated using centrifugal filters to give 0.57 mL of 10 kDa PEG IL-2 mutein 8 at 0.50 mg/mL. Analysis of the isolated conjugate was performed by SEC and RP-HPLC. Depletion of impurities from the starting material could not be achieved quantitatively by the purification step, leading to their presence in the conjugate sample, as shown by RP-HPLC. An approximate purity of conjugate 8 was determined as 25% by RP-HPLC at 280 nm with excess PEG-Mal being the main impurity.

Example 9: SPR Analysis of the PEG IL-2 Mutein Conjugates

Binding kinetics of aldesleukin and biased IL-2 compounds were assessed using surface plasmon resonance (SPR) spectroscopy with a Biacore instrument (T200, GE Healthcare) with immobilized extracellular domains of the IL-2 receptor subunits. In short, carboxymethylated dextran biosensor chips (CM5, GE Healthcare) were activated with N-(3-Dimethylaminopropyl)-N'-ethylcarbodiimide (EDC) and N-hydroxysuccinimide (NHS) according to the supplier's instructions. Immobilization of a monoclonal mouse anti-human IgG (Fc) antibody was also performed according to the supplier's instructions (GE Healthcare, order number BR-1008-39).

For the determination of binding kinetics to IL-2Rα the following chip preparation was used: Human IL-2 Receptor alpha, Fc-Tag (Symansis, New Zealand) was diluted in HBS-EP running buffer (GE Healthcare, 10 mM HEPES, 150 mM NaCl, 3 mM EDTA, 0.05% Surfactant P20, pH 7.4) to approx. 0.67 µg/mL and immobilized at a flow rate of 10 µL/min for 60 s to achieve 80-100 response units (RU).

For the determination of binding kinetics to IL-2Rβ the following chip preparation was used: Human IL-2 Receptor beta, Fe-Tag (Symansis, New Zealand) was diluted in HBS-EP running buffer (GE Healthcare, 10 mM HEPES, 150 mM NaCl, 3 mM EDTA, 0.05% Surfactant P20, pH 7.4) to around 0.80 µg/mL and immobilized at a flow rate of 10 µL/min for 60 s to achieve 140-180 response units (RU).

For the determination of binding kinetics to the IL-2Rαβ complex the following chip preparation was used: Human IL-2 Receptor alpha, Fc-Tag (Symansis, New Zealand) and Human IL-2 Receptor beta, Fc-Tag (Symansis, New Zealand) were mixed and diluted in HBS-EP running buffer (GE Healthcare, 10 mM HEPES, 150 mM NaCl, 3 mM EDTA, 0.05% Surfactant P20, pH 7.4) to around 1.33 µg/mL each and were immobilized at a flow rate of 10 L/min for 60 s to achieve 360-440 response units (RU).

For kinetic measurements on all three receptor subunit setups, Aldesleukin or biased IL-2 compounds were analysed in multi-cycle kinetics and therefore injected in at least five different concentrations in HBS-EP running buffer at 25° C. (30 L/min flow rate, 120 s contact time, 600 s dissociation time). Double referenced data (subtracted data from the reference flow cell and the buffer only samples) was, if possible analysed either kinetically via a 1:1 binding model or via steady-state analysis (Biacore T200 Evaluation Software, Version 3.1) to determine $K_D$ and if possible, $k_a$ and $k_d$. Regeneration after each cycle was performed with 3 M $MgCl_2$ for 30 s at a flow rate of 30 µL/min.

The obtained data is summarized in Table 1.

TABLE 1

Summary of SPR binding data to IL-2 receptor subunits.

| Compound | $K_D$ to IL-2Rα [nM] | $K_D$ to IL-2Rβ [nM] | $K_D$ to IL-2Rαβ [nM] | $K_D$-Ratio (αβ/β) |
|---|---|---|---|---|
| Aldesleukin | 5.65 | 287 | 0.141 | 4.91E−4 |
| 6 | >1500 | 1950 | >100 | >0.05 |
| 5 | >1000 | 1640 | >100 | >0.06 |
| 4 | >1500 | 1410 | >100 | >0.07 |
| 3 | 614 | 589 | >100 | >0.17 |
| 8 | >2000 | >2000 | >100 | — |
| 7 | 1580 | 1550 | >100 | >0.07 |

Example 10: Calculation of Bias Ratio

As used herein, the term "biased IL-2" refers to a modified IL-2, in which the ratio of the $K_D$ of said biased IL-2 to IL-2Rαβ to the $K_D$ of said biased IL-2 to IL-2Rβ is larger than the ratio of the $K_D$ of aldesleukin to IL-2Rαβ to the $K_D$ of aldesleukin to IL-2Rβ. This is described by the following formula:

$$\frac{Ratio_{biased\ IL\text{-}2}}{Ratio_{aldesleukin}} > 1$$

wherein $$Ratio_{biased\ IL\text{-}2} = \frac{K_D \text{ biased } IL\text{-}2 \text{ to } IL\text{-}2R\alpha\beta}{K_D \text{ biased } IL\text{-}2 \text{ to } IL\text{-}2\beta}$$

$$Ratio_{aldesleukin} = \frac{K_D \text{ aldesleukin to } IL\text{-}2R\alpha\beta}{K_D \text{ aldesleukin to } IL\text{-}2\beta}$$

with

"$K_D$ biased IL_2 to IL-2Rαβ" being the $K_D$ of biased IL-2 to IL-2Rαβ,

"$K_D$ biased IL-2 to IL-2Rαβ" being the $K_D$ of biased IL-2 to IL-2Rβ,

"$K_D$ aldesleukin to IL-2Rαβ" being the $K_D$ of aldesleukin to IL-2Rαβ, and

"$K_D$ aldesleukin to IL-2Rβ" being the $K_D$ of aldesleukin to IL-2Rβ.

Using the above-mentioned formula, the following ratios were calculated and summarized in Table 2.

TABLE 2

Ratio biased IL-2 to Ratio aldesleukin for different IL-2 mutein conjugates.

| Compound | $Ratio_{biased\ IL\text{-}2}$/ $Ratio_{aldesleukin}$ |
|---|---|
| 6 | >100 |
| 5 | >120 |
| 4 | >140 |
| 3 | >340 |
| 8 | n.d. |
| 7 | >140 |

Example 11: Preparation of 10 kDa PEG-IL-2 Conjugate 9

Recombinant human IL-2 is buffer exchanged into 0.2 M Tris/HCl, pH 7.5 using HiTrap Desalting columns connected to an Äkta system. Afterwards, IL-2 is enzymatically PEGylated using microbial transglutaminase (MTG) based on a procedure described in Sato et al., Bioconjugate Chem 2001, 12(5), 701-710. IL-2 at a concentration of 5 μM is incubated in the presence of a 10 kDa PEG amine (10 kDa Methoxy-PEG-$(CH_2)_2$—$NH_2$) at a concentration of 1.25 mM and MTG at a concentration of 0.2 units/mL in 0.2 M Tris/HCl, pH 7.5 at 25° C. for 12 h. 10 kDa PEG IL-2 conjugate (9) is purified from the reaction mixture by size exclusion chromatography using a GE Healthcare Superdex 200 Increase 10/300 GL column connected to an Äkta system with 10 mM HEPES, 150 mM sodium chloride, 0.05% Tween 20, pH 7.4 as mobile phase and a flow rate of 0.75 mL/min.

Example 12: Preparation of 10 kDa PEG-IL-2 Conjugate 10

Recombinant human IL-2 (2.7 mg/mL in 50 mM acetic acid, pH 3.0) is mixed with one volume equivalent of 140 mM HEPES, 300 mM NaCl, 6 mM sodium EDTA, 0.1% Tween 20, pH 8.2 resulting in 1.35 mg/mL IL-2 in 70 mM HEPES, 150 mM NaCl, 3 mM sodium EDTA, 0.05% Tween 20, 25 mm AcOH, pH 7.4. IL-2 is enzymatically PEGylated using microbial transglutaminase (MTG). For this purpose, IL-2 at a concentration of 0.1 mg/mL is incubated in 70 mM HEPES, 150 mM NaCl, 3 mM sodium EDTA, 0.05% Tween 20, 25 mm AcOH, pH 7.4 in the presence of 1 mM 10 kDa PEG amine (10 kDa Methoxy-PEG-$(CH_2)_2$—$NH_2$) and 1 U/mL MTG at 37° C. for 4 h. Afterwards, MTG blocker is added to a final concentration of 0.5 mM and the reaction mixture is incubated for additional 30 min. 10 kDa PEG IL-2 conjugate (10) is purified from the reaction mixture by size exclusion chromatography using a GE Healthcare Superdex 200 Increase 10/300 GL column connected to an Äkta system with 10 mM HEPES, 150 mM sodium chloride, 0.05% Tween 20, pH 7.4 as mobile phase and a flow rate of 0.75 mL/min.

Example 13: Preparation of Biased IL-2 Mutein Polymer Prodrug 11

PEG IL-2 mutein is buffer exchanged to 100 mM sodium borate pH 9 and concentrated to a concentration of approx. 2.5 mg/mL IL-2 eq. A five-fold molar excess of 40 kDa mPEG-linker reagent (as described in patent WO 2016079114 example 2) relative to the amount of IL-2 mutein is dissolved in an equal volume of water compared to the protein solution to be used for the conjugation reaction. Protein solution (2.5 mg/mL IL-2 eq.) and 40 kDa mPEG-Linker solution (32 g/L) are mixed and incubated for 2 hours at 14-16° C. Biased IL-2 mutein polymer prodrug 11 is isolated via CIEX and analyzed via SEC.

Example 14: Preparation of Novel Conjugate 12

40 kDa mPEG-linker reagent (as described in patent WO 2016079114 example 2) is dissolved in water to yield a 32 g/L solution. 10 kDa Mal-PEG-$NH_2$ is dissolved in 0.1 M sodium phosphate, 6 mM sodium EDTA, pH 7.4 to a final concentration of 1 mM. Both solutions are mixed in a volumetric ratio of 1 to 1 and incubated for 2 h at ambient temperature. Afterwards, 0.5 volume equivalents (with respect to the volume of the reaction mixture of 40 kDa mPEG-linker reagent and 10 kDa Mal-PEG-$NH_2$) of an IL-2 mutein 1a solution at a concentration of 2 mg/mL in 50 mM sodium phosphate, 3 mM sodium EDTA, pH 7.4 is added to the reaction mixture and incubated for 1 h at ambient temperature. 40+10 kDa PEG IL-2 mutein conjugate 12 is isolated from the reaction mixture by cation exchange chromatography and analyzed by size exclusion chromatography.

Abbreviations

A280 Absorption at a wavelength of 280 nm

AcOH Acetic Acid

CIEX Cation exchange

*E. coli Escherichia coli*

EDC N-(3-Dimethylaminopropyl)-N'-ethylcarbodiimide Hydrochloride

EDTA Ethylenediaminetetraacetic Acid eq. equivalents

HBS-EP 10 mM HEPES, 150 mM NaCl, 3 mM EDTA, 0.05% Surfactant P20, pH 7.4

HEPES 4-(2-hydroxyethyl)-1-piperazineethanesulfonic acid

IL-2 Interleukin-2

IL-2R Interleukin-2 receptor

Mal Maleimide mol.eq. molecular equivalents mPEG Methoxy PEG

MS mass spectrometry

MTG Microbial transglutaminase

NaCl Sodium chloride

NHS N-Hydroxysuccinimide

PEG Poly(ethylene glycol)

PTFE Polytetrafluoroethylene

PyBOP Benzotriazol-1-yl-oxytripyrrolidinophosphonium Hexafluorophosphate

RP-HPLC Reversed Phase High-Performance Liquid Chromatography

SEC Size-exclusion chromatography

SPR surface plasmon resonance

Tween 20 Polyethylene Glycol Sorbitan Monolaurate

The invention claimed is:

1. An IL-2 conjugate or a pharmaceutically acceptable salt thereof of formula (Ia) or (Ib)

$$Z-(L^2-L^1-D)_x \quad \text{(Ia)}$$

$$D-(L^1-L^2-Z)_y, \quad \text{(Ib)}$$

wherein

-D is a biased IL-2 moiety, which biased IL-2 moiety comprises an IL-2 moiety and for which biased IL-2 moiety the ratio of the $K_D$ of said biased IL-2 to IL-2Rαβ to the $K_D$ of said biased IL-2 to IL-2Rβ is larger than the ratio of the $K_D$ of aldesleukin to IL-2Rαβ to the $K_D$ of aldesleukin to IL-2Rβ; wherein -D comprises a stable attachment of a modifying moiety $M_{mod}$, at a single position, which is a cysteine residue replacing an amino acid of the IL-2 moiety selected from the group consisting of K34, R37, M38, T40, F41, K42, F43, Y44, E61, and L71 with positions numbered based on SEQ ID NO: 2;

-$L^1$- is a linker moiety covalently and reversibly attached to -D;

-$L^2$- is a chemical bond or is a spacer moiety;

—Z is a polymeric moiety or a substituted fatty acid moiety;

x is an integer selected from the group consisting of 1, 2, 3, 4, 5, 6, 7, 8, 9, 10, 11, 12, 13, 14, 15 or 16; and y is an integer selected from the group consisting of 2, 3, 4 and 5.

2. The IL-2 conjugate or the pharmaceutically acceptable salt thereof of claim 1, wherein the IL-2 moiety comprises the sequence of SEQ ID NO:2 with an R37C mutation.

3. The IL-2 conjugate or the pharmaceutically acceptable salt thereof of claim 1, wherein the IL-2 moiety comprises the sequence of SEQ ID NO:2 with an R37C mutation and wherein a moiety $M_{mod}$ is conjugated to the sulfur of the cysteine at position R37C of SEQ ID NO:2.

4. The IL-2 conjugate or the pharmaceutically acceptable salt thereof of claim 1, wherein the IL-2 conjugate is of formula (Ia) with x being 1.

5. The IL-2 conjugate or the pharmaceutically acceptable salt thereof of claim 1, wherein $M_{mod}$ is a polymeric moiety.

6. The IL-2 conjugate or the pharmaceutically acceptable salt thereof of claim 1, wherein $M_{mod}$ is of formula (A-1)

$$POL—SP—FG—|—, \quad \text{(A-1)}$$

wherein

-FG- is a linkage;

-SP- is a spacer moiety; and

-POL is a polymer.

7. The IL-2 conjugate or the pharmaceutically acceptable salt thereof of claim 1, wherein $M_{mod}$ is of formula (A-1a)

(A-1a)

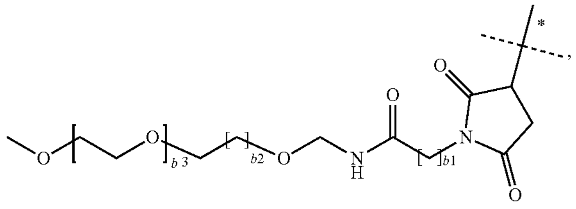

wherein the dashed line marked with the asterisk indicates attachment to the sulfur of a side chain of an amino acid residue of the IL-2 moiety;

b1 is an integer selected from the group consisting of 1, 2, 3, 4, 5, 6, 7, 8, 9, 10, 11, 12, 13, 14, 15, 16, 17, 18, 19 and 20;

b2 is an integer selected from the group consisting of 1, 2, 3, 4, 5, 6, 7, 8, 9, 10, 11, 12, 13, 14, 15, 16, 17, 18, 19 and 20; and b3 is an integer ranging from 12 to 22700.

8. The IL-2 conjugate or the pharmaceutically acceptable salt thereof of claim 1, wherein —Z is a polymeric moiety.

9. The IL-2 conjugate or the pharmaceutically acceptable salt thereof of claim 1, wherein —Z comprises a moiety of formula (A)

(A)

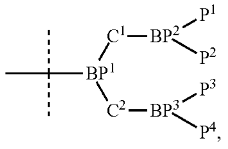

wherein

—$BP^1$<, —$BP^2$<, —$BP^3$< are independently of each other selected from the group consisting of —N< and —$C(R^8)$<;

$R^8$ is selected from the group consisting of H, $C_{1-6}$ alkyl, $C_{2-6}$ alkenyl and $C_{2-6}$ alkynyl;

—$P^1$, —$P^2$, —$P^3$, —$P^4$ are independently of each other a PEG-based chain comprising at least 40% PEG and having a molecular weight ranging from 3 to 40 kDa;

—$C^1$—, —$C^2$— are independently of each other selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $R^9$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —$C(O)N(R^{10})$—, —$S(O)_2N(R^{10})$—, —$S(O)N(R^{10})$—, —$S(O)_2$—, —S(O)—, —$N(R^{10})S(O)_2N(R^{10a})$—, —S—, —$N(R^{10})$—, —$OC(OR^{10})(R^{10a})$—, —$N(R^{10})C(O)N(R^{10a})$—, and —$OC(O)N(R^{10})$—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

wherein each T is independently optionally substituted with one or more $R^9$, which are the same or different;

each $R^9$ is independently selected from the group consisting of halogen, —CN, oxo (═O), —$COOR^{11}$, —$OR^{11}$, —$C(O)R^{11}$, —$C(O)N(R^{11}R^{11a})$, —$S(O)_2N(R^{11}R^{11a})$, —$S(O)N(R^{11}R^{11a})$, —$S(O)_2R^{11}$, —$S(O)R^{11}$, —$N(R^{11})S(O)_2N(R^{11a}R^{11b})$, —$SR^{11}$, —$N(R^{11}R^{11a})$, —$NO^2$, —$OC(O)R^{11}$, —$N(R^{11})C(O)R^{11a}$, —$N(R^{11})S(O)_2R^{11a}$, —$N(R^{11})S(O)R^{11a}$, —$N(R^{11})C(O)OR^{11a}$, —$N(R^{11})C(O)N(R^{11a}R^{11b})$, —$OC(O)N(R^{11}R^{11a})$, and $C_{1-6}$ alkyl; wherein $C_{1-6}$ alkyl is optionally substituted with one or more halogen, which are the same or different; and each $R^{10}$, $R^{10a}$, $R^{11}$, $R^{11a}$ and $R^{11b}$ is independently selected from the group consisting of —H, and $C_{1-6}$ alkyl, wherein $C_{1-6}$ alkyl is optionally substituted with one or more halogen, which are the same or different.

10. The IL-2 conjugate or the pharmaceutically acceptable salt thereof of claim 9, wherein $C^1$ and $C^2$ of formula (A) are of formula (A-a)

(A-a)

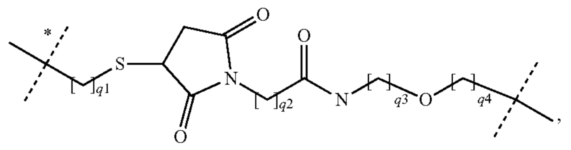

wherein the dashed line marked with the asterisk indicates attachment to $BP^1$;

the unmarked dashed line indicates attachment to $BP^2$ or $BP^3$, respectively;

q1 is selected from the group consisting of 1, 2, 3, 4, 5, 6, 7 and 8;

q2 is selected from the group consisting of 1, 2, 3, 4, and 5;

q3 is selected from the group consisting of 1, 2, 3, 4, 5, 6, 7 and 8; and q4 is selected from the group consisting of 1, 2 and 3.

11. The IL-2 conjugate or the pharmaceutically acceptable salt thereof of claim 9, wherein $P^1$, $P^2$, $P^3$ and $P^4$ of formula (A) are independently of each other of formula (A-b)

(A-b)

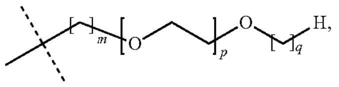

wherein the dashed line indicates attachment to the remainder of —Z;

m is 0 or 1;

p is an integer ranging from 70 to 900; and q is selected from the group consisting of 1, 2, 3, 4, 5, and 6.

12. The IL-2 conjugate or the pharmaceutically acceptable salt thereof of claim 9, wherein $BP^1$ of formula (A) is —N<.

13. The IL-2 conjugate or the pharmaceutically acceptable salt thereof of claim 9, wherein $BP^2$ and $BP^3$ of formula (A) are both —CH<.

14. The IL-2 conjugate or the pharmaceutically acceptable salt thereof of claim 1, wherein —Z comprises a moiety of formula (A-c):

(A-c)

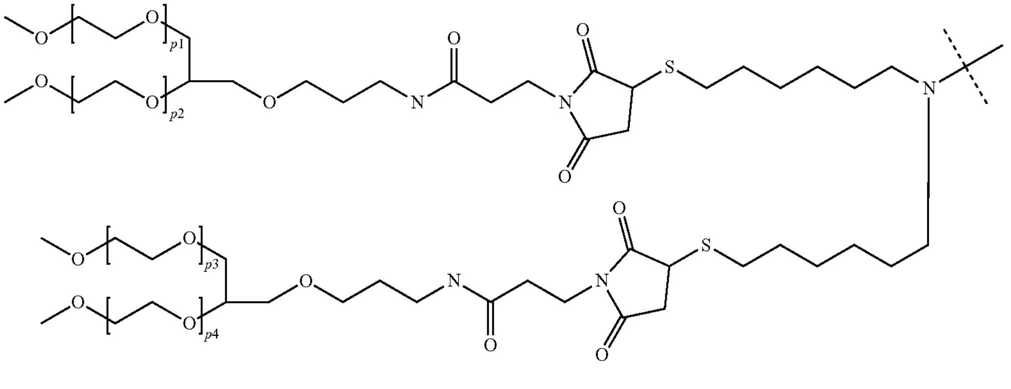;

wherein p1, p2, p3, p4 are independently of each other an integer ranging from 70 to 900.

15. The IL-2 conjugate or the pharmaceutically acceptable salt thereof of claim 1, wherein $-L^1-$ is attached to an amino acid residue of the IL-2 moiety.

16. The IL-2 conjugate or the pharmaceutically acceptable salt thereof of claim 1, wherein $-L^1-$ is of formula (IX-a):

(IX-a)

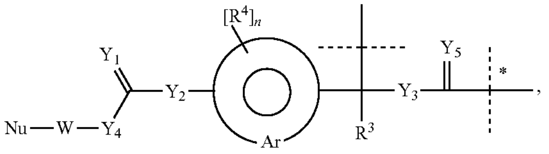

wherein the dashed line marked with the asterisk indicates attachment to a nitrogen of -D and the unmarked dashed line indicates attachment to $-L^2-Z$;

n is 0, 1, 2, 3, or 4;

$=Y_1$ is selected from the group consisting of =O and =S;

$—Y_2—$ is selected from the group consisting of —O— and —S—;

$—Y_3—$, $—Y_5—$ are independently of each other selected from the group consisting of —O— and —S—;

$—Y_4—$ is selected from the group consisting of —O—, $—NR^5—$ and $—C(R^6R^{6a})—$;

$—R^3$, $—R^5$, $—R^6$, $—R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

$—R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

—W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, $—C(O)N(R^7)—$, —O—, —S— and $—N(R^7)—$;

-Nu is a nucleophile selected from the group consisting of $—N(R^7R^{7a})$, $—N(R^7OH)$, $—N(R^7)—N(R^{7a}R^{7b})$, $—S(R^7)$, —COOH,

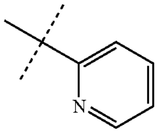, 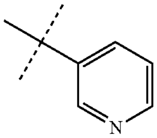, 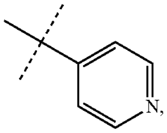

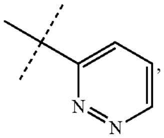, 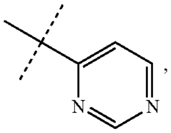, 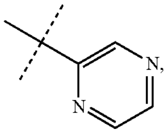

-continued

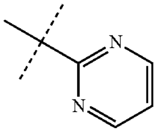, 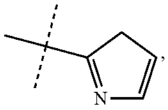, 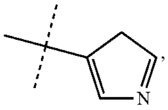

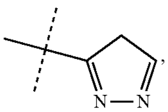, 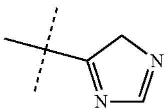 and

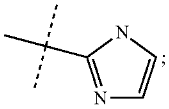;

—Ar— is selected from the group consisting of

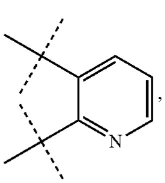, 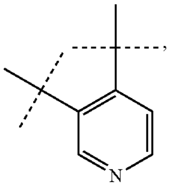,

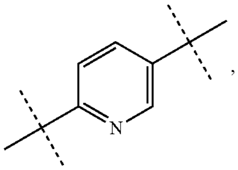, 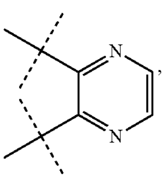,

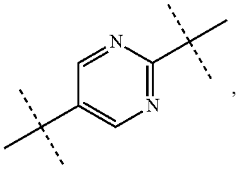, 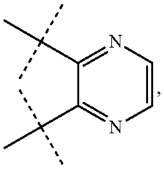,

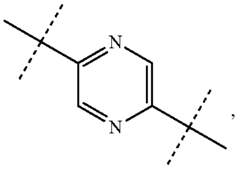, 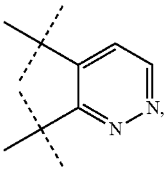

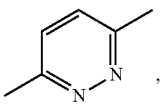, 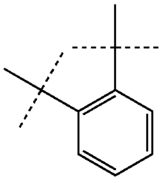, 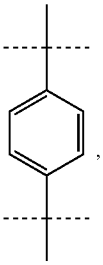,

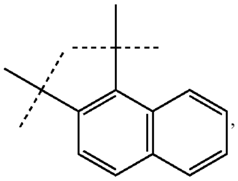, 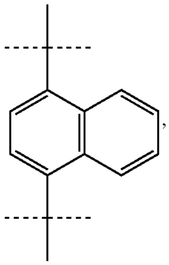,

-continued

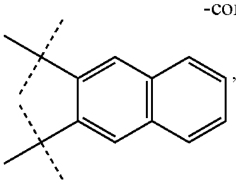,
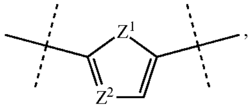,
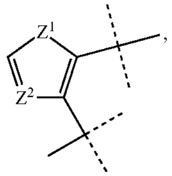,
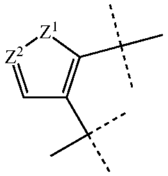
and
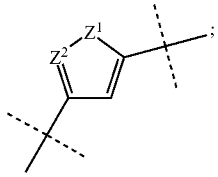;

wherein dashed lines indicate attachment to the remainder of $-L^1-$, $—Z^1—$ is selected from the group consisting of —O—, —S— and $—N(R^7)—$, and $—Z^2—$ is $—N(R^7)—$; and $—R^7$, $—R^{7a}$, $—R^{7b}$ are independently of each other selected from the group consisting of —H, $C_{1-6}$ alkyl, $C_{2-6}$ alkenyl and $C_{2-6}$ alkynyl;

wherein $-L^1-$ is optionally further substituted.

17. The IL-2 conjugate or the pharmaceutically acceptable salt thereof of claim 1, wherein $-L^1-$ is of formula (IX-c)

(IX-c)

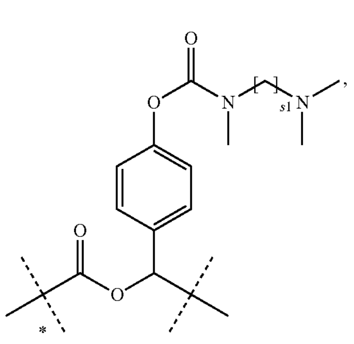

wherein the dashed line marked with the asterisk indicates attachment to a nitrogen of -D;

the unmarked dashed line indicates attachment to $-L^2-Z$; and s1 is an integer selected from the group consisting of 1, 2, 3, 4, 5, 6, 7, 8, 9 and 10.

18. The IL-2 conjugate or the pharmaceutically acceptable salt thereof of claim 1, wherein $-L^2-$ is selected from the group consisting of -T-, C(O)O—, —O—, —C(O)—, $—C(O)N(R^{y1})—$, $—S(O)_2N(R^{y1})—$, $—S(O)N(R^{y1})—$, $—S(O)_2—$, —S(O)—, $—N(R^{y1})S(O)_2N(R^{y1a})—$, —S—, $—N(R^{y1})—$, $—OC(OR^{y1})(R^{y1a})—$, $—N(R^{y1})C(O)N(R^{y1a})—$, $—OC(O)N(R^{y1})—$, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3}a)—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, —T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $—R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y4})—$, $—S(O)_2N(R^{y4})—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^{y4})(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

each $—R^{y2}$ is independently selected from the group consisting of halogen, —CN, oxo (=O), $—COOR^{y5}$, $—OR^{y5}$, $—C(O)R^{y5}$, $—C(O)N(R^{y5}R^{y5a})$, $—S(O)_2N(R^{y5}R^{y5a})$, $—S(O)N(R^{y5}R^{y5a})$, $—S(O)_2R^{y5}$, $—S(O)R^{y5}$, $—N(R^{y5})S(O)_2N(R^{y5a}R^{y5b})$, $—SR^{y5}$, $—N(R^{y5}R^{y5a})$, $—NO^2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5a}R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^{y3}$, $—R^{y3}a$, $—R^{y4}$, $—R^{y4}a$, $—R^{y5}$, $—R^{y5a}$ and $—R^{y5b}$ is independently selected from the group consisting of —H, and $C_{1-6}$ alkyl, wherein $C_{1-6}$ alkyl is optionally substituted with one or more halogen, which are the same or different.

19. The IL-2 conjugate or the pharmaceutically acceptable salt thereof of claim 1, wherein $-L^2-$ is a $C_{1-20}$ alkyl chain, which is optionally interrupted by one or more groups independently selected from —O—, -T- and $—C(O)N(R^{y1})—$; and which $C_{1-20}$ alkyl chain is optionally substituted with one or more groups independently selected from —OH, -T and $—C(O)N(R^{y6}R^{y6a})$; wherein $—R^{y1}$, $—R^{y6}$, $—R^{y6a}$ are independently selected from the group consisting of H and $C_{1-4}$ alkyl and wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

20. The IL-2 conjugate or the pharmaceutically acceptable salt thereof of claim 1, wherein $-L^2-$ is of formula (IX-e)

(IX-e)

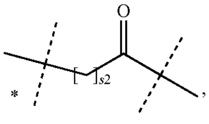, wherein the dashed line marked with the asterisk indicates attachment to $-L^1-$;

the unmarked dashed line indicates attachment to —Z; and s2 is an integer selected from the group consisting of 0, 1, 2, 3, 4, 5, 6, 7, 8, 9, 10, 11, 12, 13, 14, 15, 16, 17, 18, 19 and 20.

21. A pharmaceutical composition comprising at least one IL-2 conjugate or the pharmaceutically acceptable salt thereof of claim 1 and at least one excipient.

22. A method of treating, controlling, or delaying in a human patient in need of the treatment of one or more diseases which can be treated with IL-2, comprising the step of administering to said patient in need thereof a therapeutically effective amount of the IL-2 conjugate or a pharmaceutically acceptable salt thereof of claim 1.

23. The method of claim 22, wherein the disease is selected from the group consisting of sarcoma, chordoma, colon cancer, rectal cancer, colorectal cancer, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, gastric cancer, non-small cell lung cancer, small cell lung cancer, bladder cancer, renal cell carcinoma, urothelial cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, non-Hodgkin's lymphoma, cutaneous T-cell lymphoma, acute myeloid leukemia and leukemias.

* * * * *

SEQUENCE LISTING

```
<160> NUMBER OF SEQ ID NOS: 6

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 2
<211> LENGTH: 132
<212> TYPE: PRT
<213> ORGANISM: Artificial Sequence
<220> FEATURE:
<223> OTHER INFORMATION: aldesleukin

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 3
<211> LENGTH: 132
<212> TYPE: PRT
<213> ORGANISM: Artificial Sequence
```

```
<220> FEATURE:
<223> OTHER INFORMATION: aldesleukin mutein

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Cys Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 4
<211> LENGTH: 132
<212> TYPE: PRT
<213> ORGANISM: Artificial Sequence
<220> FEATURE:
<223> OTHER INFORMATION: aldesleukin mutein

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Cys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 5
<211> LENGTH: 132
<212> TYPE: PRT
<213> ORGANISM: Artificial Sequence
<220> FEATURE:
<223> OTHER INFORMATION: aldesleukin mutein

<400> SEQUENCE: 5
```

-continued

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Cys Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 6
<211> LENGTH: 132
<212> TYPE: PRT
<213> ORGANISM: Artificial Sequence
<220> FEATURE:
<223> OTHER INFORMATION: aldesleukin mutein

<400> SEQUENCE: 6

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Cys Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```